United States Patent
Claypool et al.

(10) Patent No.: US 10,010,330 B2
(45) Date of Patent: *Jul. 3, 2018

(54) CUT GUIDE ATTACHMENT FOR USE IN TIBIAL PROSTHESIS SYSTEMS

(71) Applicant: Zimmer, Inc., Warsaw, IN (US)

(72) Inventors: Jody L. Claypool, Warsaw, IN (US);
Steven E. Stump, Goshen, IN (US);
Wayne Paprosky, Winfield, IL (US);
David Lewallen, Rochester, MN (US);
Stephen E. White, Fort Wayne, IN (US)

(73) Assignee: Zimmer, Inc., Warsaw, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/435,620

(22) Filed: Feb. 17, 2017

(65) Prior Publication Data

US 2017/0156736 A1    Jun. 8, 2017

Related U.S. Application Data

(63) Continuation of application No. 14/304,009, filed on Jun. 13, 2014, now Pat. No. 9,597,090, and a
(Continued)

(51) Int. Cl.
| | | |
|---|---|---|
| *A61B 17/15* | (2006.01) | |
| *A61F 2/38* | (2006.01) | |
| *A61F 2/46* | (2006.01) | |

(52) U.S. Cl.
CPC ............ *A61B 17/157* (2013.01); *A61F 2/389* (2013.01); *A61F 2/4657* (2013.01); *A61F 2/4684* (2013.01)

(58) Field of Classification Search
CPC ............................ A61B 17/157; A61B 17/151
See application file for complete search history.

(56) References Cited

U.S. PATENT DOCUMENTS

| | | |
|---|---|---|
| 4,501,266 A | 2/1985 | McDaniel |
| 4,944,757 A | 7/1990 | Martinez et al. |
| (Continued) | | |

FOREIGN PATENT DOCUMENTS

| | | |
|---|---|---|
| AU | 2011343440 B2 | 4/2014 |
| CN | 1174498 A | 2/1998 |
| (Continued) | | |

OTHER PUBLICATIONS

"U.S. Appl. No. 14/833,385, Restriction Requirement dated Mar. 17, 2017", 6 pgs.
(Continued)

*Primary Examiner* — Andrew Yang
(74) *Attorney, Agent, or Firm* — Schwegman Lundberg & Woessner, P.A.

(57) ABSTRACT

Tibial prosthesis systems for implantation or use in a knee joint are disclosed. A tibial prosthesis system for implantation on a resected tibia can include a bearing component, a base component, and a shim component. The insertion of the shim component can provide spacing adjustment between the bearing and base components. The shim component can have a generally uniform height or thickness, or a variable height. A cut guide attachment, removably attachable to the prosthesis system, can be used to facilitate further resection of the tibia and create one or more additional resection surfaces on the tibia at an angle relative to the first resection surface. Multiple cut guide attachments can be available to the user to provide various resection angles. The cut guide attachment can include a modular design. The cut guide attachment can be configured to adjust the angle of the subsequent resection in at least one direction.

19 Claims, 30 Drawing Sheets

Related U.S. Application Data continuation-in-part of application No. 14/063,032, filed on Oct. 25, 2013, now Pat. No. 9,011,459, which is a continuation of application No. 13/087,610, filed on Apr. 15, 2011, now Pat. No. 8,603,101, said application No. 14/304,009 is a continuation-in-part of application No. 13/836,665, filed on Mar. 15, 2013, now Pat. No. 9,149,206.

(60) Provisional application No. 61/895,825, filed on Oct. 25, 2013, provisional application No. 61/424,222, filed on Dec. 17, 2010, provisional application No. 61/618,376, filed on Mar. 30, 2012, provisional application No. 61/740,268, filed on Dec. 20, 2012.

(56) References Cited

U.S. PATENT DOCUMENTS

| | | |
|---|---|---|
| 5,197,488 A | 3/1993 | Kovacevic |
| 5,275,603 A * | 1/1994 | Ferrante ............... A61B 17/157 606/86 R |
| 5,344,461 A | 9/1994 | Phlipot |
| 5,360,016 A | 11/1994 | Kovacevic |
| 5,364,402 A | 11/1994 | Mumme et al. |
| 5,387,239 A | 2/1995 | Bianco et al. |
| 5,395,401 A | 3/1995 | Bahler |
| 5,425,775 A | 6/1995 | Kovacevic et al. |
| 5,458,637 A | 10/1995 | Hayes |
| 5,470,354 A | 11/1995 | Hershberger et al. |
| 5,489,311 A | 2/1996 | Cipolletti |
| 5,571,194 A | 11/1996 | Gabriel |
| 5,609,645 A | 3/1997 | Vinciuerra |
| 5,656,785 A | 8/1997 | Trainor et al. |
| 5,658,341 A | 8/1997 | Delfosse |
| 5,702,464 A | 12/1997 | Lackey et al. |
| 5,733,292 A | 3/1998 | Gustilo et al. |
| 5,776,200 A | 7/1998 | Johnson et al. |
| 5,782,925 A | 7/1998 | Collazo et al. |
| 5,824,103 A | 10/1998 | Williams et al. |
| 5,871,541 A | 2/1999 | Gerber |
| 5,911,723 A | 6/1999 | Ashby et al. |
| 5,976,147 A | 11/1999 | LaSalle et al. |
| 6,126,692 A | 10/2000 | Robie et al. |
| 6,607,559 B2 | 8/2003 | Ralph et al. |
| 6,632,225 B2 | 10/2003 | Sanford et al. |
| 6,702,821 B2 | 3/2004 | Bonutti |
| 6,743,258 B1 | 6/2004 | Keller |
| 6,770,078 B2 | 8/2004 | Bonutti |
| 6,942,670 B2 | 9/2005 | Heldreth et al. |
| 6,974,481 B1 | 12/2005 | Carson |
| 7,309,363 B2 | 12/2007 | Dietz |
| 7,364,581 B2 | 4/2008 | Michalowicz |
| 7,412,897 B2 | 8/2008 | Crottet et al. |
| 7,442,196 B2 | 10/2008 | Fisher et al. |
| 7,488,330 B2 | 2/2009 | Stad |
| 7,547,327 B2 | 6/2009 | Collazo |
| 7,575,602 B2 | 8/2009 | Amirouche et al. |
| 7,578,821 B2 | 8/2009 | Fisher et al. |
| 7,587,945 B2 | 9/2009 | Crottet et al. |
| 7,591,854 B2 | 9/2009 | Wasielewski |
| 7,632,283 B2 | 12/2009 | Heldreth |
| 7,632,314 B2 | 12/2009 | Dietz |
| 7,695,520 B2 | 4/2010 | Metzger et al. |
| 7,837,691 B2 | 11/2010 | Cordes et al. |
| 7,850,698 B2 | 12/2010 | Straszheim-Morley et al. |
| 8,065,927 B2 | 11/2011 | Crottet et al. |
| 8,141,437 B2 | 3/2012 | Amirouche et al. |
| 8,197,549 B2 | 6/2012 | Amirouche et al. |
| 8,211,041 B2 | 7/2012 | Fisher et al. |
| 8,245,583 B2 | 8/2012 | Stein |
| 8,491,589 B2 | 7/2013 | Fisher et al. |
| 8,506,571 B2 | 8/2013 | Chana et al. |
| 8,603,101 B2 | 12/2013 | Claypool et al. |
| 8,932,298 B2 | 1/2015 | Colquhoun et al. |
| 8,979,847 B2 * | 3/2015 | Belcher ............... A61B 17/155 606/79 |
| 9,011,459 B2 | 4/2015 | Claypool et al. |
| 9,149,206 B2 | 10/2015 | Claypool et al. |
| 9,427,337 B2 | 8/2016 | Claypool et al. |
| 9,492,290 B2 | 11/2016 | Claypool et al. |
| 9,539,116 B2 | 1/2017 | Claypool |
| 9,597,090 B2 | 3/2017 | Claypool et al. |
| 9,763,807 B2 | 9/2017 | Claypool et al. |
| 2002/0058997 A1 | 5/2002 | O'connor et al. |
| 2002/0072802 A1 | 6/2002 | O'Neil et al. |
| 2004/0019382 A1 | 1/2004 | Amirouche et al. |
| 2004/0059340 A1 | 3/2004 | Serra et al. |
| 2004/0064191 A1 | 4/2004 | Wasielewski |
| 2004/0122441 A1 | 6/2004 | Muratsu |
| 2004/0167537 A1 | 8/2004 | Errico et al. |
| 2004/0225368 A1 | 11/2004 | Plumet et al. |
| 2004/0236429 A1 | 11/2004 | Ensign et al. |
| 2005/0055102 A1 | 3/2005 | Tornier et al. |
| 2005/0177170 A1 | 8/2005 | Fisher et al. |
| 2005/0267485 A1 | 12/2005 | Cordes et al. |
| 2006/0020343 A1 | 1/2006 | Ek |
| 2006/0052782 A1 | 3/2006 | Morgan et al. |
| 2006/0069436 A1 | 3/2006 | Sutton et al. |
| 2006/0089653 A1 | 4/2006 | Auger et al. |
| 2006/0184176 A1 | 8/2006 | Straszheim-Morley et al. |
| 2006/0189864 A1 | 8/2006 | Paradis et al. |
| 2006/0190087 A1 | 8/2006 | O'Connor |
| 2006/0111726 A1 | 10/2006 | Felt et al. |
| 2007/0123992 A1 | 5/2007 | Sanford |
| 2007/0234819 A1 | 10/2007 | Amirouche et al. |
| 2007/0239165 A1 | 10/2007 | Amirouche |
| 2008/0051908 A1 | 2/2008 | Angibaud et al. |
| 2008/0091273 A1 | 4/2008 | Hazebrouck |
| 2008/0103603 A1 | 5/2008 | Hintermann |
| 2009/0005708 A1 | 1/2009 | Johanson et al. |
| 2009/0125114 A1 | 5/2009 | May et al. |
| 2009/0204222 A1 | 8/2009 | Burstein et al. |
| 2009/0259314 A1 | 10/2009 | Linder-ganz et al. |
| 2009/0264894 A1 | 10/2009 | Wasielewski |
| 2009/0287310 A1 | 11/2009 | Fisher et al. |
| 2009/0306787 A1 | 12/2009 | Crabtree et al. |
| 2009/0319048 A1 | 12/2009 | Shah et al. |
| 2010/0010494 A1 | 1/2010 | Quirno |
| 2010/0063595 A1 | 3/2010 | Dietz |
| 2010/0076563 A1 | 3/2010 | Otto et al. |
| 2010/0082111 A1 | 4/2010 | Thomas |
| 2010/0100011 A1 | 4/2010 | Roche |
| 2010/0198275 A1 | 8/2010 | Chana et al. |
| 2010/0249660 A1 | 9/2010 | Sherman et al. |
| 2010/0249789 A1 | 9/2010 | Rock et al. |
| 2011/0100011 A1 | 5/2011 | Staffend |
| 2012/0095563 A1 | 4/2012 | Sanford et al. |
| 2012/0158152 A1 | 6/2012 | Claypool et al. |
| 2012/0179069 A1 | 7/2012 | Amirouche |
| 2012/0232429 A1 | 9/2012 | Fischer et al. |
| 2012/0290088 A1 | 11/2012 | Amirouche et al. |
| 2012/0310246 A1 | 12/2012 | Belcher et al. |
| 2013/0013076 A1 | 1/2013 | Fisher et al. |
| 2013/0079671 A1 | 3/2013 | Stein et al. |
| 2013/0096567 A1 | 4/2013 | Fisher et al. |
| 2013/0102929 A1 | 4/2013 | Haight et al. |
| 2013/0103038 A1 | 4/2013 | Fischer et al. |
| 2013/0253378 A1 | 9/2013 | Claypool et al. |
| 2013/0261504 A1 | 10/2013 | Claypool et al. |
| 2013/0261757 A1 | 10/2013 | Claypool et al. |
| 2013/0261758 A1 | 10/2013 | Claypool et al. |
| 2014/0052269 A1 | 2/2014 | Claypool et al. |
| 2014/0296859 A1 | 10/2014 | Claypool et al. |
| 2015/0088140 A1 | 3/2015 | Toler et al. |
| 2015/0190243 A1 | 7/2015 | Claypool et al. |
| 2015/0359642 A1 | 12/2015 | Claypool et al. |
| 2016/0324647 A1 | 11/2016 | Claypool et al. |
| 2018/0000612 A1 | 1/2018 | Claypool et al. |

FOREIGN PATENT DOCUMENTS

| | | |
|---|---|---|
| CN | 1440262 A | 9/2003 |
| CN | 101522136 A | 9/2009 |

(56) References Cited

FOREIGN PATENT DOCUMENTS

| CN | 101646392 A | 2/2010 |
|---|---|---|
| CN | 101711701 A | 5/2010 |
| CN | 101835441 A | 9/2010 |
| CN | 102018584 A | 4/2011 |
| CN | 103370025 A | 10/2013 |
| CN | 103379880 A | 10/2013 |
| CN | 104379094 A | 2/2015 |
| CN | 104736105 A | 6/2015 |
| CN | 105055052 A | 11/2015 |
| CN | 103370025 B | 11/2016 |
| EP | 0903125 A1 | 3/1999 |
| EP | 1132063 A2 | 9/2009 |
| EP | 2237177 A1 | 10/2010 |
| EP | 2830543 A1 | 2/2015 |
| EP | 2830544 A1 | 2/2015 |
| EP | 2830544 B1 | 9/2016 |
| EP | 2918235 B1 | 1/2017 |
| FR | 2824260 A1 | 11/2002 |
| JP | 61247449 A | 11/1986 |
| JP | 09289998 A | 11/1997 |
| JP | 2007054488 A | 3/2007 |
| JP | 2009245619 A | 10/2009 |
| JP | 2010240406 A | 10/2010 |
| JP | 2012500667 A | 1/2012 |
| JP | 2015512307 A | 4/2013 |
| JP | 2014505517 A | 3/2014 |
| JP | 2014508554 A | 4/2014 |
| JP | 2014239900 A | 12/2014 |
| JP | 2015513966 A | 5/2015 |
| WO | WO-2010022272 A1 | 2/2010 |
| WO | WO-2010023062 A2 | 3/2010 |
| WO | WO-2011063123 A2 | 5/2011 |
| WO | WO-2012004580 A1 | 1/2012 |
| WO | WO-2012020460 A1 | 2/2012 |
| WO | WO-2012082628 A1 | 6/2012 |
| WO | WO-2012083280 A1 | 6/2012 |
| WO | WO-2013013094 A1 | 1/2013 |
| WO | WO-2013148954 A1 | 10/2013 |
| WO | WO-2013148960 A1 | 10/2013 |

OTHER PUBLICATIONS

"Japanese Application Serial No. 2015-503563, Response Filed Mar. 13, 2017 to Office Action dated Dec. 20, 2016", (W/ English Translation), 9 pgs.
"U.S. Appl. No. 13/087,610, Non Final Office Action dated Feb. 26, 2013", 7 pgs.
"U.S. Appl. No. 13/087,610, Notice of Allowance dated Jun. 28, 2013", 6 pgs.
"U.S. Appl. No. 13/087,610, Notice of Allowance dated Oct. 8, 2013", 7 pgs.
"U.S. Appl. No. 13/087,610, Response filed May 24, 2013 to Non Final Office Action dated Feb. 26, 2013", 15 pgs.
"U.S. Appl. No. 13/819,116, Advisory Action dated Jan. 5, 2016", 3 pgs.
"U.S. Appl. No. 13/819,116, Corrected Notice of Allowance dated Oct. 21, 2016", 2 pgs.
"U.S. Appl. No. 13/819,116, Examiner Interview Summary dated Apr. 18, 2016", 11 pgs.
"U.S. Appl. No. 13/819,116, Final Office Action dated Jul. 26, 2016", 6 pgs.
"U.S. Appl. No. 13/819,116, Final Office Action dated Oct. 21, 2015", 15 pgs.
"U.S. Appl. No. 13/819,116, Non Final Office Action dated Feb. 17, 2016", 15 pgs.
"U.S. Appl. No. 13/819,116, Non Final Office Action dated Jun. 2, 2015", 14 pgs.
"U.S. Appl. No. 13/819,116, Notice of Allowance dated Sep. 29, 2016", 5 pgs.
"U.S. Appl. No. 13/819,116, Preliminary Amendment filed Feb. 26, 2013", 8 pgs.
"U.S. Appl. No. 13/819,116, Response filed Mar. 27, 2015 to Restriction Requirement dated Feb. 12, 2015", 11 pgs.
"U.S. Appl. No. 13/819,116, Response filed Apr. 29, 2016 to Non Final Office Action dated Feb. 17, 2016", 17 pgs.
"U.S. Appl. No. 13/819,116, Response filed Jul. 16, 2015 to Non Final Office Action dated Jun. 2, 2015", 22 pgs.
"U.S. Appl. No. 13/819,116, Response filed Sep. 14, 2016 Final Office Action dated Jul. 26, 2016", 10 pgs.
"U.S. Appl. No. 13/819,116, Response filed Dec. 15, 2015 to Final Office Action dated Oct. 21, 2015", 16 pgs.
"U.S. Appl. No. 13/819,116, Restriction Requirement dated Feb. 12, 2015", 7 pgs.
"U.S. Appl. No. 13/836,586, Express Abandonment filed May 30, 2014", 1 pg.
"U.S. Appl. No. 13/836,665, Examiner Interview Summary dated Jul. 17, 2014", 4 pgs.
"U.S. Appl. No. 13/836,665, Final Office Action dated Jul. 25, 2014", 25 pgs.
"U.S. Appl. No. 13/836,665, Non Final Office Action dated Jan. 30, 2014", 21 pgs.
"U.S. Appl. No. 13/836,665, Notice of Allowance dated Jun. 9, 2015", 10 pgs.
"U.S. Appl. No. 13/836,665, Response filed Jan. 23, 2015 to Final Office Action dated Jul. 25, 2014", 25 pgs.
"U.S. Appl. No. 13/836,665, Response filed May 30, 2014 to Non-Final Office Action dated Jan. 30, 2014", 21 pgs.
"U.S. Appl. No. 13/837,294, Final Office Action dated Apr. 25, 2016", 7 pgs.
"U.S. Appl. No. 13/837,294, Final Office Action dated Jun. 2, 2016", 7 pgs.
"U.S. Appl. No. 13/837,294, Non Final Office Action dated Dec. 10, 2015", 8 pgs.
"U.S. Appl. No. 13/837,294, Notice of Allowance dated Aug. 25, 2016", 5 pgs.
"U.S. Appl. No. 13/837,294, Response filed Mar. 4, 2016 to Non Final Office Action dated Dec. 10, 2015", 16 pgs.
"U.S. Appl. No. 13/837,294, Response filed Aug. 3, 2016 to Final Office Action dated Jun. 2, 2016", 7 pgs.
"U.S. Appl. No. 13/837,294, Response filed Oct. 12, 2015 to Restriction Requirement dated Aug. 24, 2015", 9 pgs.
"U.S. Appl. No. 13/837,294, Restriction Requirement dated Aug. 24, 2015", 6 pgs.
"U.S. Appl. No. 13/837,774, Examiner Interview Summary dated Jul. 22, 2014", 4 pgs.
"U.S. Appl. No. 13/837,774, Final Office Action dated Mar. 17, 2016", 14 pgs.
"U.S. Appl. No. 13/837,774, Final Office Action dated Jul. 28, 2014", 17 pgs.
"U.S. Appl. No. 13/837,774, Non Final Office Action dated Feb. 10, 2014", 33 pgs.
"U.S. Appl. No. 13/837,774, Non Final Office Action dated Sep. 18, 2015", 16 pgs.
"U.S. Appl. No. 13/837,774, Response filed Jan. 28, 2015 to Final Office Action dated Jul. 28, 2014", 16 pgs.
"U.S. Appl. No. 13/837,774, Response filed Jun. 10, 2014 to Non-Final Office Action dated Feb. 20, 2014", 29 pgs.
"U.S. Appl. No. 13/837,774, Response filed Jul. 7, 2015 to Restriction Requirement dated May 20, 2015", 10 pgs.
"U.S. Appl. No. 13/837,774, Response filed Dec. 16, 2015 to Non Final Office Action dated Sep. 18, 2015", 17 pgs.
"U.S. Appl. No. 13/837,774, Restriction Requirement dated May 20, 2015", 6 pgs.
"U.S. Appl. No. 14/034,076, Appeal Brief Filed Apr. 18, 2016", 21 pgs.
"U.S. Appl. No. 14/034,076, Final Office Action dated Dec. 21, 2015", 11 pgs.
"U.S. Appl. No. 14/034,076, Non Final Office Action dated Jun. 24, 2015", 11 pgs.
"U.S. Appl. No. 14/034,076, Notice of Allowance dated Oct. 28, 2016", 7 pgs.
"U.S. Appl. No. 14/034,076, Response filed Nov. 16, 2015 to Non Final Office Action dated Jun. 24, 2015", 13 pgs.

(56) References Cited

OTHER PUBLICATIONS

"U.S. Appl. No. 14/063,032, Non Final Office Action dated Jun. 20, 2014", 6 pgs.
"U.S. Appl. No. 14/063,032, Notice of Allowance dated Dec. 19, 2014", 6 pgs.
"U.S. Appl. No. 14/063,032, Preliminary Amendment filed Oct. 25, 2013", 3 pgs.
"U.S. Appl. No. 14/063,032, Response filed Oct. 20, 2014 to Non-Final Office Action dated Jun. 20, 2014", 9 pgs.
"U.S. Appl. No. 14/304,009, Notice of Allowance dated Nov. 16, 2016", 7 pgs.
"U.S. Appl. No. 14/304,009, Preliminary Amendment Filed Jul. 31, 2014", 7 pgs.
"U.S. Appl. No. 14/660,217, Corrected Notice of Allowance dated May 26, 2016", 3 pgs.
"U.S. Appl. No. 14/660,217, Non Final Office Action dated Dec. 17, 2015", 8 pgs.
"U.S. Appl. No. 14/660,217, Notice of Allowance dated Apr. 26, 2016", 5 pgs.
"U.S. Appl. No. 14/660,217, Preliminary Amendment filed Mar. 18, 2015", 9 pgs.
"U.S. Appl. No. 14/660,217, Response filed Mar. 23, 2016 to Non Final Office Action dated Dec. 17, 2015", 14 pgs.
"U.S. Appl. No. 14/833,385, Preliminary Amendment filed Aug. 25, 2015", 6 pgs.
"U.S. Appl. No. 15/211,812, Non Final Office Action dated Jan. 27, 2017", 5 pgs.
"U.S. Appl. No. 15/211,812, Preliminary Amendment filed Sep. 8, 2016", 8 pgs.
"Australian Application Serial No. 2011343440, First Examiner Report dated Feb. 17, 2014", 3 pgs.
"Australian Application Serial No. 2011343440, Response filed Mar. 21, 2014 to Office Action dated Feb. 17, 2014", 1 pg.
"Australian Application Serial No. 2013238046, First Examiner Report dated Nov. 26, 2015", 2 pgs.
"Australian Application Serial No. 2013238046, Response filed Feb. 2, 2016 to First Examiner Report dated Nov. 26, 2015", 1 pg.
"Australian Application Serial No. 2013238054, First Examiner Report dated Oct. 17, 2016", 4 pgs.
"Australian Application Serial No. 2013238054, Response filed Jan. 18, 2017 to First Examiner Report dated Oct. 17, 2016", 9 pgs.
"Canadian Application Serial No. 2,821,927, Voluntary Amendment dated Jun. 14, 2013", 7 pgs.
"Canadian Application Serial No. 2,824,527, Office Action dated Mar. 17, 2014", 2 pgs.
"Canadian Application Serial No. 2,824,527, Response filed Sep. 17, 2014 to Office Action dated Mar. 17, 2014", 14 pgs.
"Chinese Application Serial No. 201180067430.X, Office Action dated Aug. 28, 2014", (W/ English Translation), 8 pgs.
"Chinese Application Serial No. 201180067430.X, Response filed Jan. 4, 2015 to Office Action dated Sep. 26, 2014", (W/ English Translation), 14 pgs.
"Chinese Application Serial No. 201180067757.7, Office Action dated Mar. 2, 2015", (W/ English Translation), 18 pgs.
"Chinese Application Serial No. 201180067757.7, Office Action dated Jun. 1, 2016", (W/ English Translation), 10 pgs.
"Chinese Application Serial No. 201180067757.7, Office Action dated Nov. 16, 2015", (W/ English Translation), 17 pgs.
"Chinese Application Serial No. 201180067757.7, Response filed Jan. 27, 2016 to Office Action dated Nov. 16, 2015", (W/ English Translation of Claims), 12 pgs.
"Chinese Application Serial No. 201180067757.7, Response filed Jul. 10, 2015 to Office Action dated Mar. 2, 2015", (W/ English Translation), 13 pgs.
"Chinese Application Serial No. 201180067757.7, Response filed Aug. 11, 2016 to Office Action dated Jun. 1, 2016", W/ English Translation of Claims, 9 pgs.
"Chinese Application Serial No. 201180067757.7, Voluntary Amendment dated Feb. 14, 2014", (W/ English Translation of Claims), 8 pgs.
"Chinese Application Serial No. 201380028572.4, Office Action dated Aug. 13, 2015", (W/ English Translation), 16 pgs.
"Chinese Application Serial No. 201380028683.5, Office Action dated Jun. 27, 2016", (W/ English Translation), 8 pgs.
"Chinese Application Serial No. 201380028683.5, Office Action dated Nov. 4, 2015", (W/ English Translation), 16 pgs.
"Chinese Application Serial No. 201380028683.5, Office Action dated Dec. 30, 2016", W/ English Translation, 4 pgs.
"Chinese Application Serial No. 201380028683.5, Response filed Feb. 8, 2017 to Office Action dated Dec. 30, 2016", 13 pgs.
"Chinese Application Serial No. 201380028683.5, Response filed Mar. 18, 2016 to Office Action dated Nov. 4, 2015", (W/ English Translation of Claims), 11 pgs.
"Chinese Application Serial No. 201380028683.5, Response filed Sep. 6, 2016 to Office Action dated Jun. 27, 2016", English Translation of Claims, 11 pgs.
"Chinese Application Serial No. 201510394094.X, Office Action dated Aug. 30, 2016", (With English Translation), 14 pgs.
"Chinese Application Serial No. 201510394094.X, Response filed Jan. 16, 2017 to Office Action dated Aug. 30, 2016", With English Translation of Claims, 11 pgs.
"European Application Serial No. 11808493.8, Response filed Feb. 26, 2014 to Communication pursuant to Rules 161(1) and 162 EPC dated Aug. 16, 2013", 14 pgs.
"European Application Serial No. 11808493.8, Response filed Apr. 18, 2016 to Communication Pursuant to Article 94(3) EPC dated Dec. 7, 2015", 15 pgs.
"European Application Serial No. 11808493.8, Response filed Jul. 2, 2015 to Examination Notification Art. 94(3) dated Feb. 20, 2015", 13 pgs.
"European Application Serial No. 11808493.8, Communication Pursuant to Article 94(3) EPC dated Dec. 7, 2015", 4 pgs.
"European Application Serial No. 11808493.8, Examination Notification Art. 94(3) dated Feb. 20, 2015", 6 pgs.
"European Application Serial No. 13716636.9, Communication Pursuant to Article 94(3) EPC dated Nov. 16, 2015", 4 pgs.
"European Application Serial No. 13716636.9, Communication Pursuant to Article 94(3) EPC dated Nov. 17, 2016", 4 pgs.
"European Application Serial No. 13716636.9, Communication Pursuant to Article 94(3) EPC dated Jun. 6, 2016", 5 pgs.
"European Application Serial No. 13716636.9, Communication pursuant to Rules 161(1) and 162 EPC dated Dec. 12, 2014", 2 pgs.
"European Application Serial No. 13716636.9, Response filed Mar. 24, 2016 to Communication Pursuant to Article 94(3) EPC dated Nov. 16, 2015", 18 pgs.
"European Application Serial No. 13716636.9, Response filed Jun. 22, 2015 to Communication pursuant to Rules 161(1) and 162 EPC dated Dec. 12, 2014", 10 pgs.
"European Application Serial No. 13716636.9, Response filed Oct. 17, 2016 to Communication Pursuant to Article 94(3) EPC dated Jun. 6, 2016", 5 pgs.
"European Application Serial No. 14190180.1, Extended European Search Report dated Sep. 24, 2015", 8 pgs.
"International Application Serial No. PCT/US2011/064435, International Preliminary Report on Patentability dated Jun. 27, 2013", 9 pgs.
"International Application Serial No. PCT/US2011/064435, Search Report dated Jun. 21, 2012", 5 pgs.
"International Application Serial No. PCT/US2011/064435, Written Opinion dated Jun. 21, 2012", 7 pgs.
"International Application Serial No. PCT/US2011/065683, International Preliminary Report on Patentability dated Jun. 27, 2013", 11 pgs.
"International Application Serial No. PCT/US2011/065683, International Search Report dated Apr. 24, 2012", 12 pgs.
"International Application Serial No. PCT/US2011/065683, Written Opinion dated Apr. 24, 2012", 10 pgs.
"International Application Serial No. PCT/US2013/034286, International Preliminary Report on Patentability dated Oct. 9, 2014", 8 pgs.
"International Application Serial No. PCT/US2013/034286, International Search Report dated Jun. 25, 2013", 6 pgs.

(56) References Cited

OTHER PUBLICATIONS

"International Application Serial No. PCT/US2013/034286, Written Opinion dated Jun. 25, 2013", 6 pgs.
"International Application Serial No. PCT/US2013/034293, International Preliminary Report on Patentability dated Oct. 9, 2014", 9 pgs.
"International Application Serial No. PCT/US2013/034293, International Search Report dated Jun. 25, 2013", 6 pgs.
"International Application Serial No. PCT/US2013/034293, Written Opinion dated Jun. 25, 2013", 7 pgs.
"Japanese Application Serial No. 2013-544655, Office Action dated Mar. 8, 2016", (W/ English Translation), 8 pgs.
"Japanese Application Serial No. 2013-544655, Office Action dated Sep. 29, 2015", (W/ English Translation), 7 pgs.
"Japanese Application Serial No. 2013-544655, Response filed Jan. 4, 2016 to Office Action dated Sep. 29, 2015", (English Translation of Claims), 14 pgs.
"Japanese Application Serial No. 2013-544655, Response filed Jul. 14, 2016 to Office Action dated Mar. 8, 2016", (w/ English Translation of Claims), 13 pgs.
"Japanese Application Serial No. 2013-544858, Request for Examination filed Feb. 4, 2014", (With English Translation), 14 pgs.
"Japanese Application Serial No. 2014-121515, Notice of Reasons for Rejection dated Jan. 5, 2016", (W/ English Translation), 9 pgs.
"Japanese Application Serial No. 2014-121515, Office Action dated Jun. 2, 2015", (W/ English Translation), 10 pgs.
"Japanese Application Serial No. 2014-121515, Response filed May 11, 2016 to Notice of Reasons for Rejection dated Jan. 5, 2016", W/ English Translation of Claims, 11 pgs.
"Japanese Application Serial No. 2014-121515, Response filed Aug. 20, 2015 to Office Action dated Jun. 2, 2015", W/ English Translation of Claims, 6 pgs.
"Japanese Application Serial No. 2015-503563, Office Action dated Dec. 20, 2016", 10 pgs.
"Zimmer NexGen Trabecular Metal Tibial Tray", Surgical Technique, Zimmer, Inc., (2007, 2009), 16 pgs.
"Zimmer Patient Specific Instruments", Surgical Techniques for NexGen Complete Knee Solution Zimmer, Inc., (2010), 16 pgs.
"U.S. Appl. No. 14/833,385, Non Final Office Action dated Jun. 19, 2017", 10 pgs.
"U.S. Appl. No. 14/833,385, Response filed May 12, 2017 to Restriction Requirement dated Mar. 17, 2017", 8 pgs.
"U.S. Appl. No. 14/833,385, Response filed Sep. 18, 2017 to Non Final Office Action dated Jun. 19, 2017", 14 pgs.
"U.S. Appl. No. 15/211,812, Notice of Allowance dated May 31, 2017", 5 pgs.
"U.S. Appl. No. 15/211,812, Response filed Apr. 19, 2017 to Non Final Office Action dated Jan. 27, 2017", 9 pgs.
"U.S. Appl. No. 15/703,698, Preliminary Amendment filed Sep. 28, 2017", 8 pgs.
"Chinese Application Serial No. 201510394094.X, Office Action dated May 24, 2017", (W/ English Translation), 11 pgs.
"Chinese Application Serial No. 201510394094.X, Response filed Jul. 10, 2017 to Office Action dated May 24, 2017", (W/ English Translation), 10 pgs.
"European Application Serial No. 13716636.9, Response filed Mar. 27, 2017 to Communication Pursuant to Article 94(3) EPC dated Nov. 17, 2016", 15 pgs.
"European Application Serial No. 16183635.8, Extended European Search Report dated Jun. 30, 2017", 9 pgs.
"U.S. Appl. No. 14/833,385, Examiner Interview Summary dated Dec. 27, 2017", 3 pgs.
"U.S. Appl. No. 14/833,385, Final Office Action dated Nov. 13, 2017", 9 pgs.
"Chinese Application Serial No. 201510394094.X, Office Action dated Nov. 3, 2017", W/English Translation, 10 pgs.
"Chinese Application Serial No. 201510394094.X, Response filed Jan. 18, 2018 to Office Action dated Nov. 3, 2017", w/English Claims, 10 pgs.
"European Application Serial No. 11802835.6, Communication Pursuant to Article 94(3) EPC dated Dec. 11, 2017", 4 pgs.

* cited by examiner

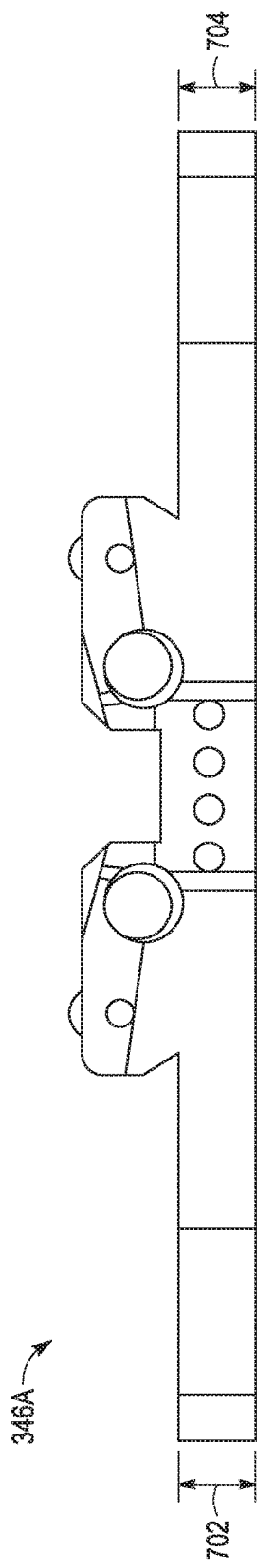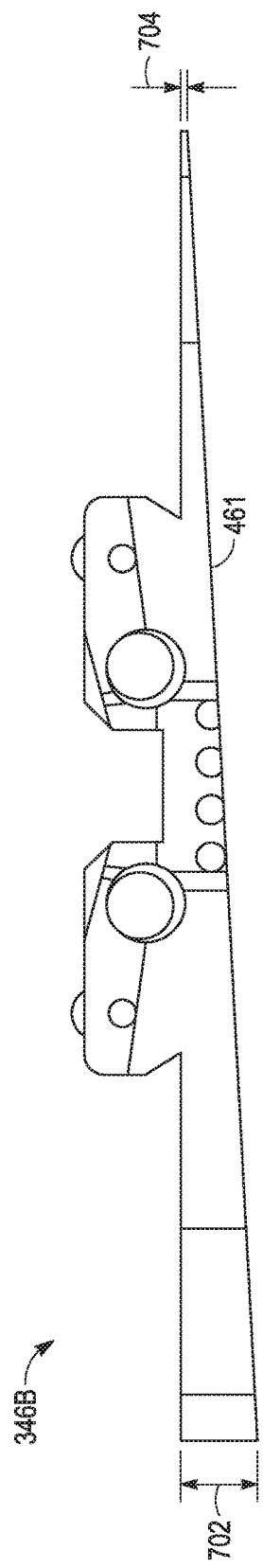

CUT GUIDE ATTACHMENT FOR USE IN TIBIAL PROSTHESIS SYSTEMS

CLAIM OF PRIORITY

This application is a continuation of U.S. patent application Ser. No. 14/304,009, filed on Jun. 13, 2014, which claims the benefit of priority under 35 U.S.C. § 119(e) of U.S. Provisional Patent Application Ser. No. 61/895,825, entitled "CUT GUIDE ATTACHMENT FOR USE IN TIBIAL PROSTHESIS SYSTEMS," filed on Oct. 25, 2013, which is herein incorporated by reference in its entirety. This application is a continuation-in-part of U.S. patent application Ser. No. 14/063,032, entitled "PROVISIONAL TIBIAL PROSTHESIS SYSTEM," filed on Oct. 25, 2013, now issued as U.S. Pat. No. 9,011,459, which is a continuation of U.S. patent application Ser. No. 13/087,610, entitled "PROVISIONAL TIBIAL PROSTHESIS SYSTEM," filed on Apr. 15, 2011, now issued as U.S. Pat. No. 8,603,101, which claims the benefit of priority under 35 U.S.C. § 119(e) of U.S. Provisional Patent Application Ser. No. 61/424,222, entitled "USER INTERFACE RELATED TO A SURGICAL PROVISIONAL," filed on Dec. 17, 2010, each of which is herein incorporated by reference in its entirety. This application is a continuation-in-part of U.S. patent application Ser. No. 13/836,665, entitled "TIBIAL PROSTHESIS SYSTEMS, KITS, AND METHODS," filed on Mar. 15, 2013, now issued as U.S. Pat. No. 9,149,206, which claims the benefit of priority under 35 U.S.C. § 119(e) of U.S. Provisional Patent Application Ser. No. 61/618,376, entitled "TIBIAL PROSTHESIS SYSTEMS, KITS, AND METHODS," filed on Mar. 30, 2012, and also claims the benefit of priority under 35 U.S.C. § 119(e) of U.S. Provisional Patent Application Ser. No. 61/740,268, entitled "TIBIAL PROSTHESIS SYSTEMS, KITS, AND METHODS," filed on Dec. 20, 2012, each of which is herein incorporated by reference in its entirety.

TECHNICAL FIELD

This patent document pertains generally to tibial prosthesis systems, kits, and methods.

BACKGROUND

Provisional knee prosthesis systems, including a plurality of provisional components, can be positioned on a distal end of a femur or a proximal end of a tibia to allow a surgeon to test and appropriately fit a permanent knee prosthesis system within a patient. During surgery, the surgeon can remove and replace a provisional component having a first uniform thickness with a provisional component having a second uniform thickness to arrive at an appropriate configuration of the permanent knee prosthesis system. During surgery, the surgeon can make one or more additional resections on the tibia.

Overview

This patent document pertains generally to provisional tibial prosthesis systems, kits, and methods, including one or more provisional tibial components that can collectively be used to replicate permanent (or final) tibial components or mimic bone cuts believed to be necessary during a surgical procedure. It is believed that the provisional tibial components can also be designed for, or find use as, permanent tibial components. Thus, while this disclosure relates to provisional uses of the present tibial prosthesis systems, kits, and methods, it should be appreciated that such subject matter can also find use in permanent applications. When used provisionally, the tibial prosthesis systems, kits, and methods disclosed herein can assist in determining a proper bone cut angle to be made (e.g., to a tibia or a femur) or a size, shape, or other configuration of a permanent tibial prosthesis system that is designed to replace all or a portion of a knee joint. The present tibial prosthesis systems, kits, and methods can be used in conjunction with one or both of a permanent tibial prosthesis system, as disclosed in U.S. Provisional Patent Application Ser. No. 61/381,800, filed on Sep. 10, 2010 and entitled "TIBIAL PROSTHESIS FACILITATING ROTATIONAL ALIGNMENT," or a shim handling instrument and user-interface, as disclosed in U.S. Provisional Patent Application Ser. No. 61/424,222, filed on Dec. 17, 2010 and entitled "USER INTERFACE RELATED TO A SURGICAL PROVISIONAL," the entire disclosures of each of which are hereby expressly incorporated by reference herein.

The present inventors recognize, among other things, that existing provisional systems, kits, and methods fail to provide a surgeon with insight of knee joint kinematics if an angled bone cut (e.g., a bone cut that is not parallel to a joint line of the knee) is made to a proximal end of the tibia or a distal end of the femur. The present inventors further recognize that existing provisional systems, kits, and methods require the stacking of a high number of provisional components to arrive at an appropriate configuration of the permanent tibial prosthesis system or fail to provide sensed force or pressure data providing a real-time indication of provisional knee joint balance.

The present shim components, which can include one or both of a medial edge having a different height than a lateral edge or an anterior edge having a different height than a posterior edge, advantageously provide a surgeon with knee joint kinematic insight regarding an angled bone cut before the cut is made and can reduce the number of provisional components needed for permanent system sizing. The present shim components can provide the surgeon with the ability to appropriately configure the tibia, the femur, and/or the permanent tibial prosthesis system to counterbalance a deficiency (e.g., varus, valgus, anterior/posterior, or posterior/anterior sloping) of the knee joint before making certain angled bone cuts and using a reduced number of provisional components.

A tibial prosthesis system can include a provisional bearing component, a bearing support component, such as a base or plate component, and the provisional shim component. The shim component can be inserted between an inferior surface of the bearing component and a superior surface of the bearing support component. The insertion of the shim component provides spacing adjustment between the bearing and bearing support components. A sensor can be coupled to or integrated with the bearing, bearing support, or shim components for real-time knee joint balance testing.

The tibial prosthesis system can also include one or more cut guides removably attachable to the tibial prosthesis system and configured to facilitate further resection of the proximal tibia. Each of the one or more cut guides can include an elongated slot configured to receive a cutting tool for further resecting the proximal tibia at an angle relative to a first resected surface created prior to implanting the provisional component. The angle can result in a second resected surface that includes a slope in one or both of an anterior-posterior direction or a medial-lateral direction. The one or more cut guides can be removably attachable to the provisional shim component.

To further illustrate the tibial prosthesis systems disclosed herein, a non-limiting list of examples is provided here:

In Example 1, a system for performing a surgical procedure on a portion of a knee joint can comprise a provisional tibial prosthesis system implantable on a first resected surface of a proximal tibia and comprising a tibial base plate, a tibial bearing component attachable to the tibial base plate, and at least one shim slidably receivable between the tibial base plate and the tibial bearing component. The system can further comprise a cut guide removably attachable to the tibial prosthesis system and configured to facilitate further resection of the proximal tibia.

In Example 2, the system of Example 1 can optionally be configured such that the cut guide is configured to create a second resected surface of the proximal tibia that is at an angle relative to the first resected surface.

In Example 3, the system of Example 2 can optionally be configured such that the second resected surface includes one or both of a slope in an anterior-posterior direction or a slope in a medial-lateral direction, relative to the first resected surface.

In Example 4, the system of any one or any combination of Examples 1-3 can optionally be configured such that the cut guide is removably attachable to the at least one shim.

In Example 5, the system of Example 4 can optionally be configured such that the at least one shim includes one or more alignment voids on an end of the at least one shim, and the cut guide includes one or more alignment pins configured to fit into the one or more alignment voids on the at least one shim.

In Example 6, the system of any one or any combination of Examples 1-5 can optionally be configured such that the cut guide includes an elongated slot configured to receive a cutting tool for creating the second resected surface of the proximal tibia.

In Example 7, the system of Example 6 can optionally be configured such that the cut guide includes at least one adjustment mechanism for adjusting an angle of the elongated slot in at least one direction, relative to the first resected surface.

In Example 8, the system of Example 7 can optionally be configured such that the at least one adjustment mechanism includes a ball and at least one clamp, the at least one clamp adjustable and configured to releasably engage the ball, and adjustment of the at least one clamp relative to the ball adjusts an angle of the elongated slot, in at least one direction, relative to the first resected surface.

In Example 9, the system of Example 7 can optionally be configured such that the cut guide includes a slotted portion and a main body portion, the elongated slot formed in the slotted portion.

In Example 10, the system of Example 9 can optionally be configured such that the at least one adjustment mechanism includes first teeth formed on an end of the slotted portion and second teeth formed on an end of the main body portion. The first and second teeth can be configured to releasably mate with one another at different positions corresponding to different angles of the elongated slot relative to the first resected surface.

In Example 11, the system of Example 9 can optionally be configured such that the cut guide includes a connector portion having at least one feature for releasable attachment of the cut guide to the at least one shim, and the least one adjustment mechanism includes a shaft extending from the main body portion and a recess formed in the connector portion. The shaft and recess can be configured to releasably engage with one another at different positions corresponding to different angles of the elongated slot relative to the first resected surface.

In Example 12, the system of any one or any combination of Examples 1-11 can optionally be configured such that the at least one shim includes a first shim having a first shim height, and the tibial bearing component and the tibial base plate are separated by a first distance equal to the first shim height.

In Example 13, the system of Example 12 can optionally be configured such that the at least one shim includes a second shim having a second shim height, and the second shim replaces the first shim for placement between the tibial base plate and the tibial bearing component or the second shim is used in combination with the first shim.

In Example 14, a system for performing a surgical procedure on a portion of a knee joint can comprise a provisional tibial prosthesis system implantable on a first resected surface of a proximal tibia and comprising a tibial base plate, a tibial bearing component, and at least one shim positionable between the tibial base plate and the tibial bearing component. The system can further comprise a plurality of cut guides, each cut guide removably attachable to the prosthesis system and having an elongated slot configured to receive a cutting tool for further resecting the proximal tibia at an angle relative to the first resected surface.

In Example 15, the system of Example 14 can optionally be configured such that each cut guide has an elongated slot configured such that each cut guide is configured to create an angled resection, relative to the first resected surface, that is different from an angled resection created by another cut guide included in the plurality of cut guides.

In Example 16, the system of Example 15 can optionally be configured such that the angled resection includes one or both of a slope in an anterior-posterior direction or a slope in a medial-lateral direction, relative to the first resected surface.

In Example 17, the system of Example 16 can optionally be configured such that the slope in the anterior-posterior direction is between +3 degrees and −3 degrees, inclusive, relative to the first resected surface, and the slope in the medial-lateral direction is between +2 degrees and −2 degrees, inclusive, relative to the first resected surface.

In Example 18, a method of performing a surgical procedure on a portion of a knee joint can comprise resecting a proximal tibia to form a first resected proximal tibia surface, and implanting a provisional tibial prosthesis system on the resected proximal tibia surface. The prosthesis system can comprise a tibial base plate, a tibial bearing component attachable to the tibial base plate, and a first shim receivable between the tibial base plate and the tibial bearing component. The method can further comprise testing a force balance on at least a portion of the knee joint and performing a second resection of the proximal tibia to form a second resected proximal tibia surface. The second resected proximal tibia surface can be at an angle relative to the first resected proximal tibia surface, and the second resection can be performed using a cut guide removably attachable to the prosthesis system.

In Example 19, the method of Example 18 can optionally be configured such that the cut guide used in performing the second resection is removably attachable to the first shim.

In Example 20, the method of any one or any combination of Examples 18 or 19 can optionally be configured such that the cut guide used in performing the second resection is selected from a plurality of cut guides configured to create different resection angles relative to one another.

In Example 21, the method of any one or any combination of Examples 18-20 can optionally be configured such that the cut guide comprises an elongated slot configured to receive a cutting tool for performing the second resection, and at least one adjustment mechanism for adjusting an angle of the elongated slot in at least one direction, relative to the first resected proximal tibia surface.

In Example 22, the method of Example 21 can optionally be configured such that the at least one adjustment mechanism includes a ball and at least one clamp, the at least one clamp adjustable and configured to releasably engage the ball. Adjustment of the at least one clamp relative to the ball can adjust an angle of the elongated slot, in at least one direction, relative to the first resected proximal tibia surface.

In Example 23, the method of any one or any combination of Examples 18-22 can optionally be configured such that performing a second resection of the proximal tibia includes creating a second resection having one or both of a slope in an anterior-posterior direction or a slope in a medial-lateral direction, relative to the first resected proximal tibia surface.

In Example 24, the method of any one or any combination of Examples 18-23 can optionally further comprise prior to performing the second resection, when the force balance is not satisfactory, removing the first shim and inserting a second shim between the tibial base plate and the tibial bearing component. The second shim can have a height different than a height of the first shim. The method can further comprise retesting the force balance on at least a portion of the knee joint.

In Example 25, the system or method of any one or any combination of Examples 1-24 can optionally be configured such that all elements or options recited are available to use or select from.

These and other examples and features of the present systems and methods will be set forth in part in the following Detailed Description. This Overview is intended to provide non-limiting examples of the present subject matter—it is not intended to provide an exclusive or exhaustive explanation. The Detailed Description below is included to provide further information about the present tibial prosthesis systems and methods.

BRIEF DESCRIPTION OF THE DRAWINGS

In the drawings, like numerals can be used to describe similar elements throughout the several views. Like numerals having different letter suffixes can be used to represent different views or features of similar elements. The drawings illustrate generally, by way of example, but not by way of limitation, various embodiments discussed in the present application.

FIGS. 15-16 illustrate front views of a shim component of a tibial prosthesis system, as constructed in accordance with at least two embodiments.

DETAILED DESCRIPTION

The present disclosure provides a provisional tibial prosthesis system for a set of prosthetic knee joints for implantation in a natural knee, the provisional tibial prosthesis system including a bearing component and a bearing support, the spacing of the bearing component from the bearing support is adjustable to allow for representation of a variety of different sized final tibial prosthesis. The prosthesis system described herein can include one or more cut guide attachments that can be removably attachable to components of the prosthesis and can be used to create one or more additional resection surfaces on the tibia.

The provisional tibial prosthesis system of the present disclosure may be used with a final tibial prosthesis in accordance with the tibial prosthesis described in U.S. Patent Application Ser. No. 61/381,800, filed Sep. 10, 2010, entitled "Tibial Prosthesis Facilitating Rotational Alignment," the entire disclosure of which is hereby expressly incorporated herein by reference. Further, the provisional tibial prosthesis system of the present disclosure may be used with the method and apparatus described in U.S. Patent Application Ser. No. 61/424,222, filed Dec. 17, 2010, entitled "User Interface Related to a Surgical Provisional," the entire disclosure of which was previously incorporated herein by reference.

Figure 6:
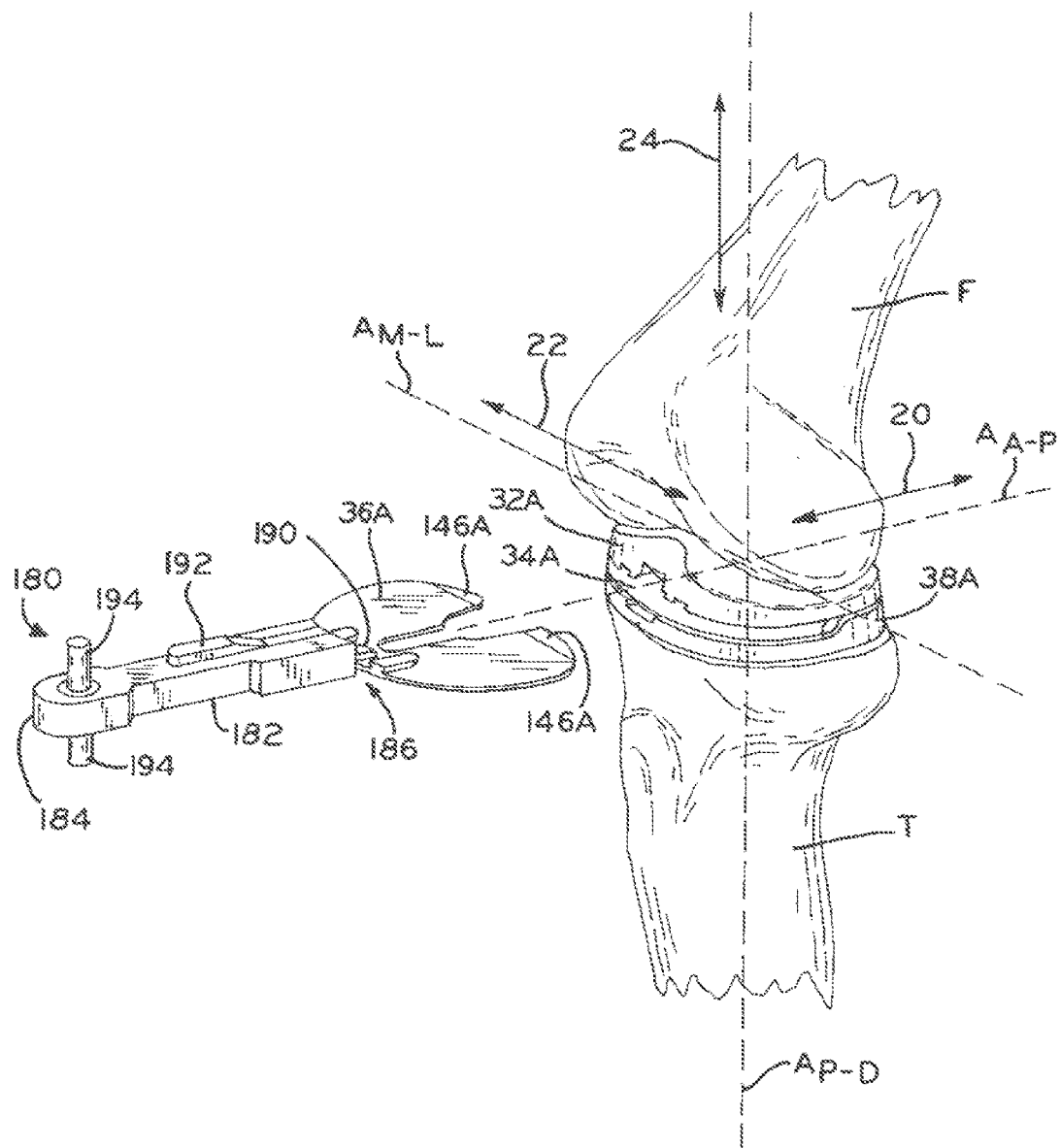
FIG. 6 is a perspective view of a knee joint and the provisional tibial prosthesis system of FIG. 1 illustrating a resected proximal tibia surface with the tibial base plate of FIG. 5 attached thereon, the base component of FIG. 3A positioned on the tibial base plate, the tibial bearing component of FIG. 2A attached to the base component, and a surgical instrument connected to the shim of FIG. 4A, and illustrating axes of the knee joint.

FIG. 6 illustrates a natural knee comprising proximal tibial T and distal femur F. FIG. 6 depicts a coordinate system of the natural knee including anterior/posterior axis $A_{A-P}$, medial/lateral axis $A_{M-L}$, and proximal/distal axis $A_{P-D}$. Anterior/posterior axis $A_{A-P}$ corresponds to anterior/posterior direction 20, medial/lateral axis $A_{M-L}$ corresponds to medial/lateral direction 22, and proximal/distal axis $A_{P-D}$ corresponds to proximal/distal direction 24. Anterior/posterior direction 20, medial/lateral direction 22, and proximal/distal direction 24 are each normal to one another. As used herein, "proximal" refers to a direction generally toward the heart of a patient, and "distal" refers to the opposite direction of proximal, i.e., away from the heart of the patient. Further, as used herein, "anterior" refers to a direction generally toward the front of a patient, and "posterior" refers to the opposite direction of anterior, i.e., toward the back of a patient. As used herein, "medial" refers to a direction generally toward the middle of a patient, and "lateral" refers to the opposite direction of medial, i.e., toward the side of a patient. For purposes of this disclosure, the above-mentioned anatomical references are used in the description of the components of the provisional tibial prosthesis system with reference to a desired operable use of the components in the body.

While the exemplary embodiments detailed herein are shown and described with regard to a left knee, it will be appreciated that the present disclosure is equally applicable to a right knee configuration.

Figure 1:
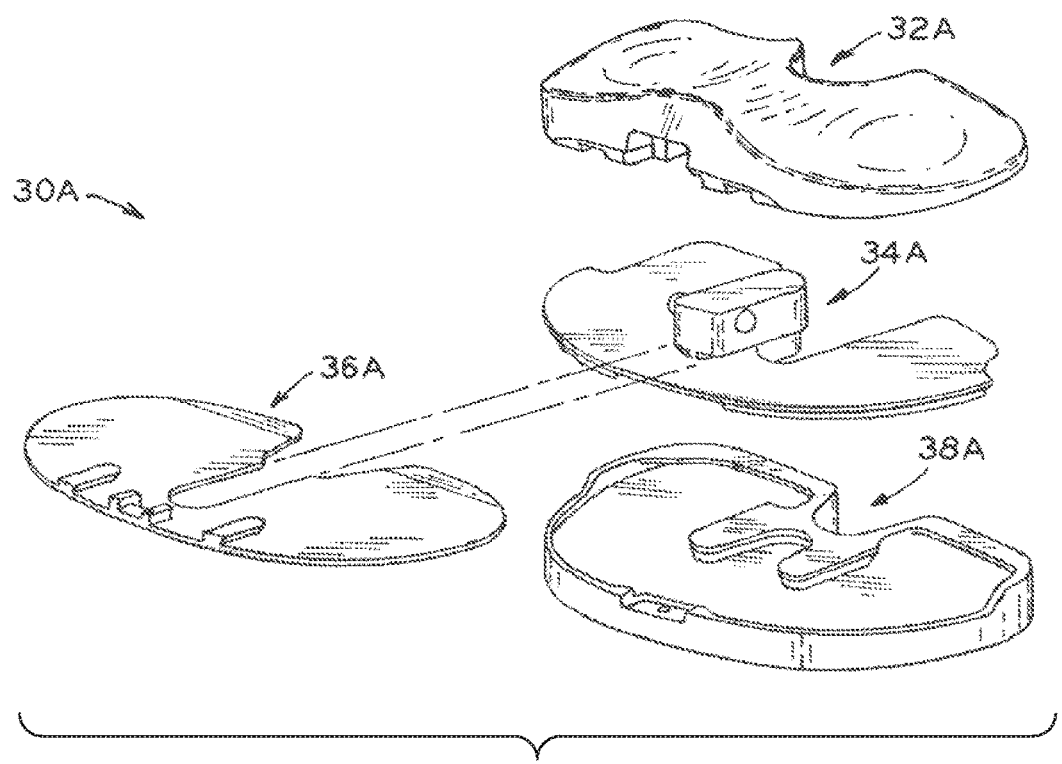
FIG. 1 is an exploded perspective view of a provisional tibial prosthesis system in accordance with an exemplary first embodiment of the present disclosure.

The disclosed embodiments of the present disclosure include a tibial bearing component and a base component. For example, as shown in FIG. 1 of an exemplary first embodiment, provisional tibial prosthesis system 30A includes tibial bearing component 32A and base component 34A. Reference numbers for the provisional tibial prosthesis system, the tibial bearing component, and the base component utilize the same numerical reference number combined with different letters to distinguish the exemplary embodiment (i.e., tibial bearing component 32A, 32B, 32C, etc. respectively correspond to the first, second, and third exemplary embodiments, etc.). For the purposes of this disclosure, a reference numeral followed by A-K corresponds to a similar feature between the exemplary first through eleventh embodiments, respectively.

Figure 2A:
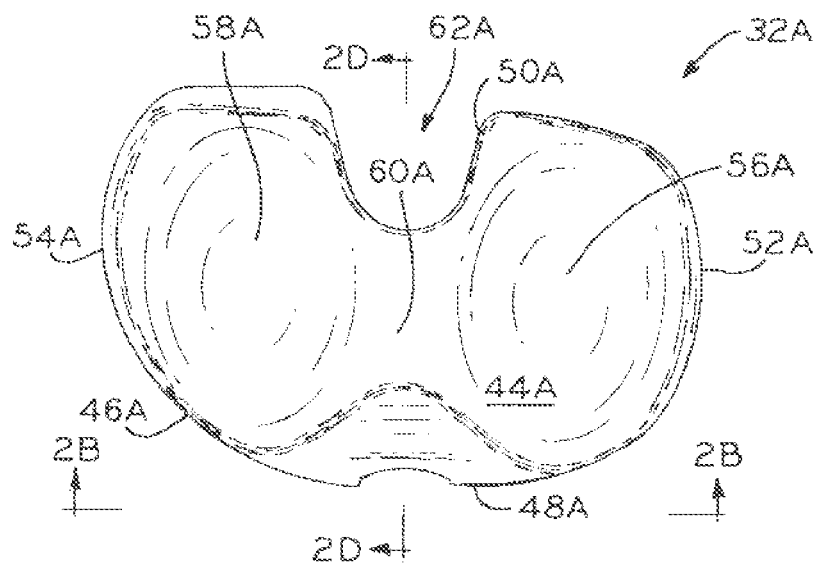
FIG. 2A is a plan view of a tibial bearing component of the provisional tibial prosthesis system of FIG. 1.

The common elements between the eleven described exemplary embodiments follow a similar reference number labeling scheme. For example, the first exemplary embodiment, as illustrated in FIGS. 2A-2D, includes tibial bearing component 32A generally including tibial bearing component inferior surface 42A, opposing tibial bearing component superior surface 44A, and tibial bearing component peripheral wall 46A extending from inferior surface 42A to superior surface 44A. Tibial bearing component 32A includes bearing anterior side 48A, bearing posterior side 50A, bearing lateral side 52A, and bearing medial side 54A. Superior surface 44A is adapted to articulate with condyles of a distal femur F (shown in FIGS. 6-8), or condyles of a femoral component (not shown) secured to a distal end of a femur. Superior surface 44A includes bearing lateral particular surface 56A in bearing lateral side 52A and bearing medial particular surface 58A in bearing medial side 54A, with central tibial eminence 60A disposed between bearing particular surfaces 56A, 58A. Referring to FIG. 2A, eminence 60A generally corresponds in shape and size with the natural tibial eminence of a proximal tibial T (shown in FIGS. 6-8) prior to resection. Tibial bearing component 32A further includes PCL cut-out 62A disposed at posterior side 50A between lateral particular surface 56A and medial particular surface 58A. PCL cut-out 62A is sized and positioned to correspond with a posterior cruciate retaining ligament of a knee joint.

In the exemplary embodiment of FIGS. 2A-2D, tibial bearing component 32A is illustrated as a cruciate retaining bearing component though it is contemplated that other tibial bearing components may be utilized in accordance with the present disclosure such as bearing components which cooperate to form a posterior stabilized prosthesis or a knee prosthesis having an intermediate level of constraint between a posterior stabilized and cruciate retaining prosthesis. Tibial bearing component 32A may also be made available in a variety of shapes and sizes to accommodate a variety of knee joints.

Figure 2B:
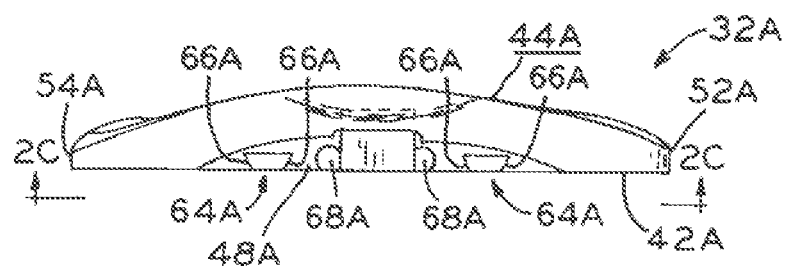
FIG. 2B is a front elevation view of the tibial bearing component of FIG. 2A.
Figure 2C:
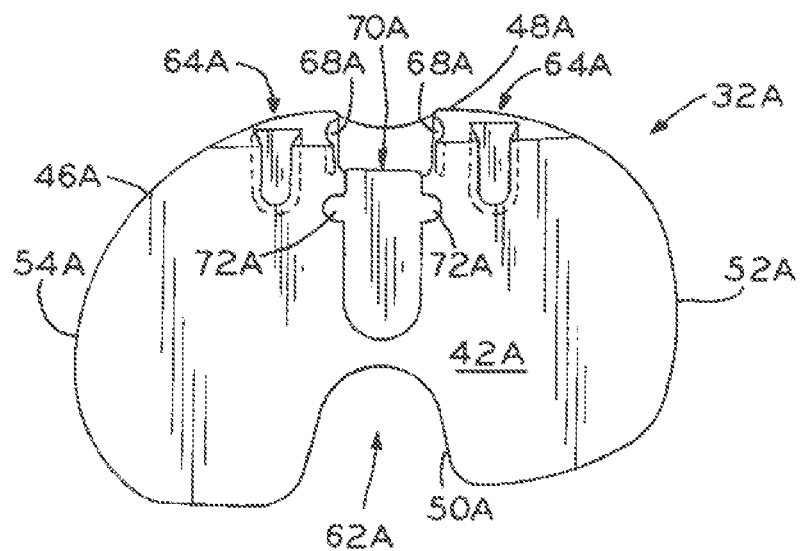
FIG. 2C is a bottom view of the tibial bearing component of FIG. 2A.
Figure 2D:
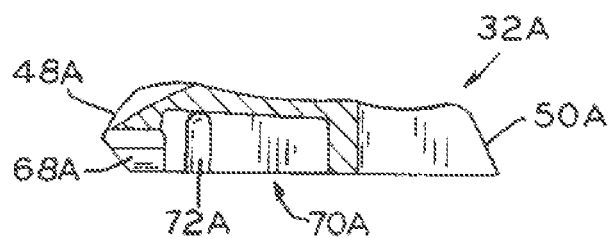
FIG. 2D is a cross-sectional view taken along line 2D-2D of FIG. 2A.

As shown in FIGS. 2A-2D, tibial bearing inferior surface 42A of tibial bearing component 32A includes slots 64A, alignment pins 68A, bearing cavity 70A, and bearing nub cavities 72A. As illustrated in FIGS. 2B and 2C, slots 64A are exposed at anterior side 48A and extend from anterior side 48A toward posterior side 50A within tibial bearing component 32A in a direction parallel to anterior/posterior axis $A_{A-P}$. As shown in FIG. 2B, in an exemplary embodiment, slots 64A have tapering walls 66A. Referring to FIGS. 2B and 2C, alignment pins 68A are located between slots 64A at anterior side 48A. Bearing cavity 70A extends from inferior surface 42A towards superior surface 44A and is sized to accept protrusion 96A (shown in FIG. 3A) of base component 34A. Further, bearing cavity 70A includes bearing nub cavities 72A which extend on opposing sides of bearing cavity 70A and are each sized to receive a nub 104A (shown in FIG. 3A) located on protrusion 96A of base component 34A.

Figure 3A:
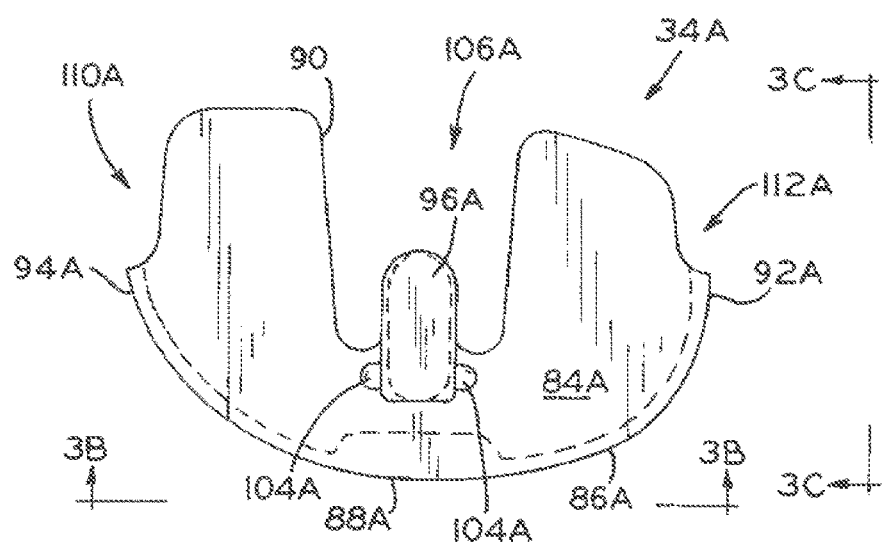
FIG. 3A is a plan view of a base component of the provisional tibial prosthesis system of FIG. 1.
Figure 3B:
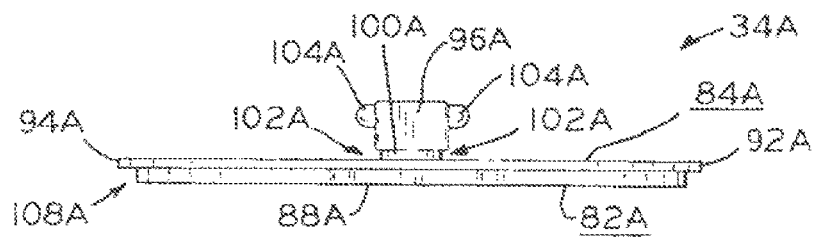
FIG. 3B is a front elevation view of the base component of FIG. 3A.
Figure 3C:
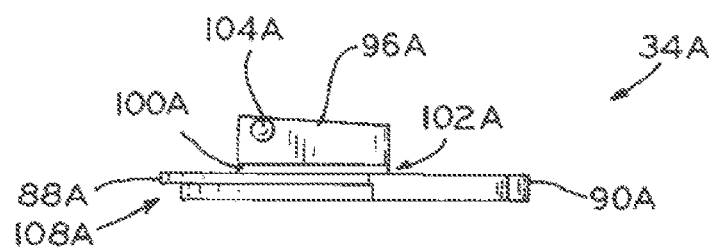
FIG. 3C is a side elevation view of the base component of FIG. 3A.

The first exemplary embodiment, as illustrated in FIGS. 3A-3C, also includes base component 34A generally including base component inferior surface 82A, opposing base component superior surface 84A, and base component peripheral wall 86A extending from inferior surface 82A to superior surface 84A. Base component 34A includes base anterior side 88A, base posterior side 90A, base lateral side 92A, and base medial side 94A.

Base component 34A includes protrusion 96A extending from superior surface 84A. Protrusion 96A includes nubs 104A which extend on opposing sides of protrusion 96A. Referring to FIG. 3B, protrusion bottom wall 100A spans the distance between protrusion 96A and superior surface 84A. Further, protrusion 96A and bottom wall 100A define bottom wall indentations 102A between protrusion 96A and superior surface 84A. Base component 34A also includes notch 106A at posterior side 90A having a generally W-shape, undercut portion 108A, medial side groove 110A, and lateral side groove 112A.

Figure 5:
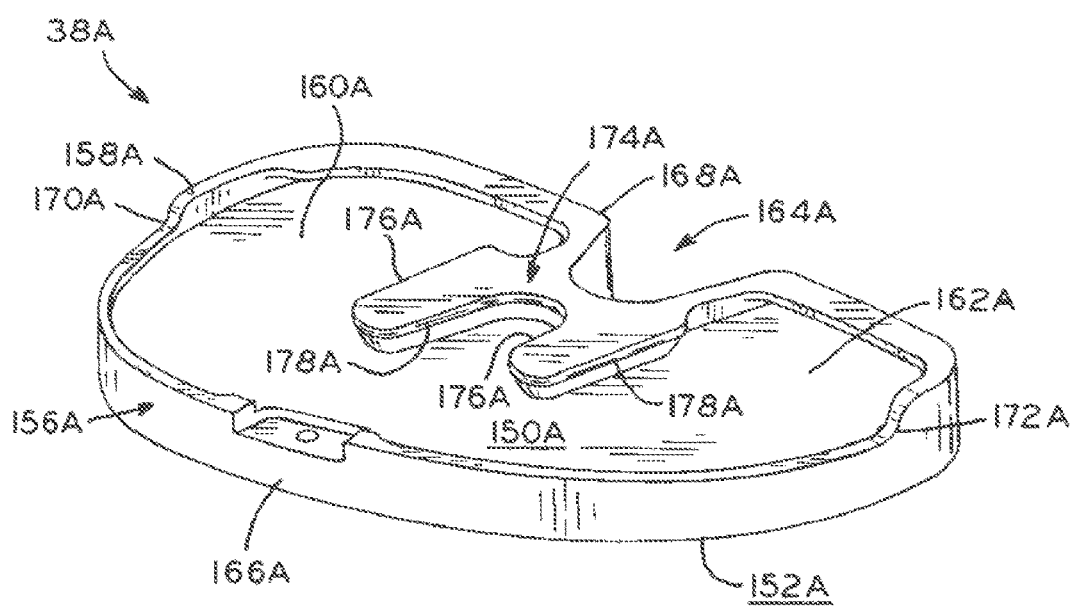
FIG. 5 is a perspective view of a tibial base plate of the provisional tibial prosthesis system of FIG. 1.

FIG. 5 illustrates tibial base plate 38A according to an exemplary embodiment of the present disclosure. Tibial base plate 38A generally includes base plate superior surface 150A and opposing base plate bone contacting surface 152A. Tibial base plate 38A closely corresponds in size and shape with the resected proximal tibia surface, and includes base plate peripheral wall 156A extending from bone contacting surface 152A to superior surface 150A. Base plate peripheral wall 156A includes raised perimeter 158A and tibial base plate 38A includes base plate anterior side 166A, base plate posterior side 168A, base plate medial side 170A, and base plate lateral side 172A. Superior surface 150A includes medial condylar portion 160A and lateral condylar portion 162A. Base plate 38A further includes PCL cut-out 164A disposed at posterior side 168A between medial condylar portion 160A and lateral condylar portion 162A to allow a posterior cruciate retaining ligament of a knee joint to pass therethrough. Further, tibial base plate 38A includes boss 174A having boss medial sides 176A and boss lateral sides 178A. Further, an interior recess is formed between inner medial side 176A and inner lateral side 178A.

The manner in which tibial base plate 38A is attached to a proximal tibia will now be discussed. The proximal portion of a patient's tibia is resected to provide a substantially flat surface for receipt of bone contacting surface 152A of tibial base plate 38A. Once the proximal tibia is resected, tibial base plate 38A is implanted and secured to the resected proximal tibia using standard surgical techniques. For example, conventional features such as a stem and fins may be located on bone contacting surface 152A to affect securement of tibial base plate 38A to a proximal tibia. While tibial base plate 38A is part of the provisional prosthesis system disclosed herein, tibial base plate 38A may also be part of a final prosthesis system, i.e., tibial base plate 38A is the final base plate implanted to a resected proximal tibia. Tibial base plate 38A may also be part of any other tibia contacting implement utilized in knee arthroplasty. For example, tibial base plate 38A could be part of a tibial sizing plate system in accordance with the tibial sizing plate described in U.S. Pat. No. 7,850,698, issued Dec. 14, 2010, entitled "Tibial Trialing Assembly and Method of Trialing a Tibial Implant," the entire disclosure of which is hereby expressly incorporated herein by reference. Tibial base plate 38A may also be part of a tibial sizing plate system in accordance with the tibial sizing plate described in two brochures published by Zimmer, Inc., namely the "Zimmer® Patient Specific Instruments, Surgical Techniques for NexGen® Complete Knee Solution" brochure, copyright 2010, and the "Zimmer® NexGen Trabecular Metal Tibial Tray, Surgical Technique" brochure, copyright 2007 and 2009, the entire disclosures of which are hereby expressly incorporated herein by reference.

Figure 7:
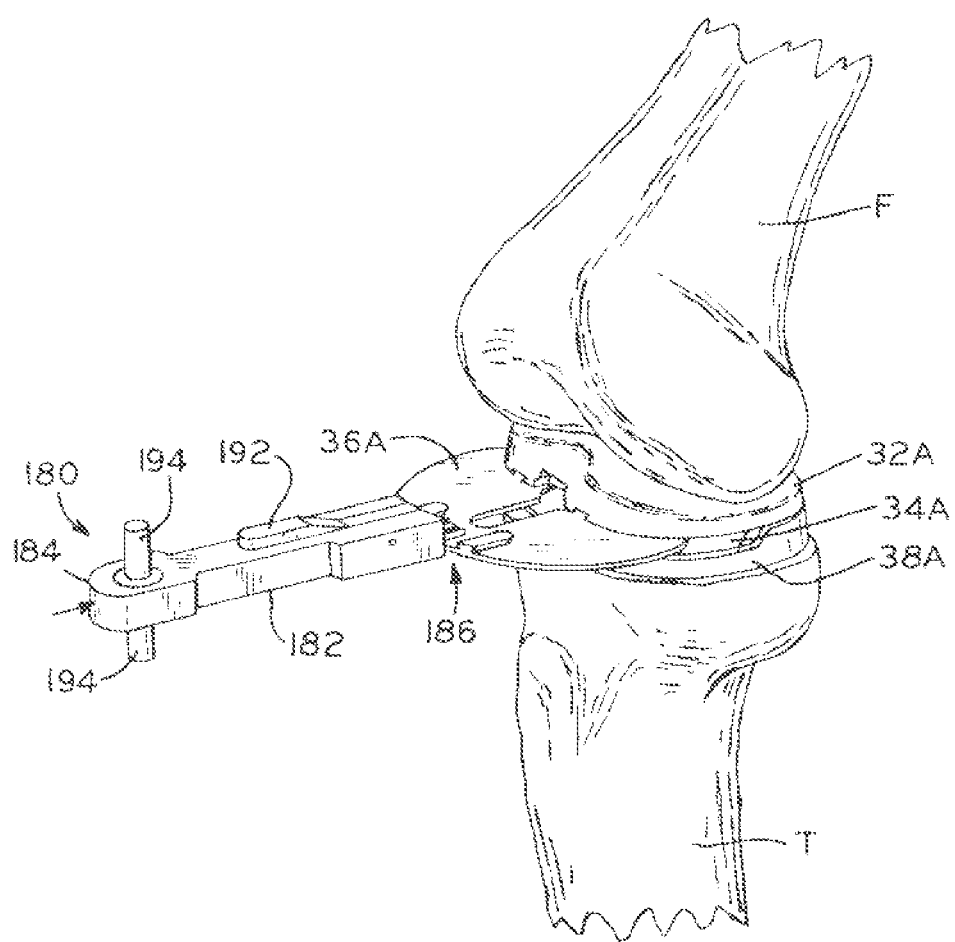
FIG. 7 is a perspective view of the provisional tibial prosthesis system of FIG. 6 illustrating using the surgical instrument of FIG. 6 to slide the shim between the base component and the tibial bearing component in an anterior/posterior direction.
Figure 8:
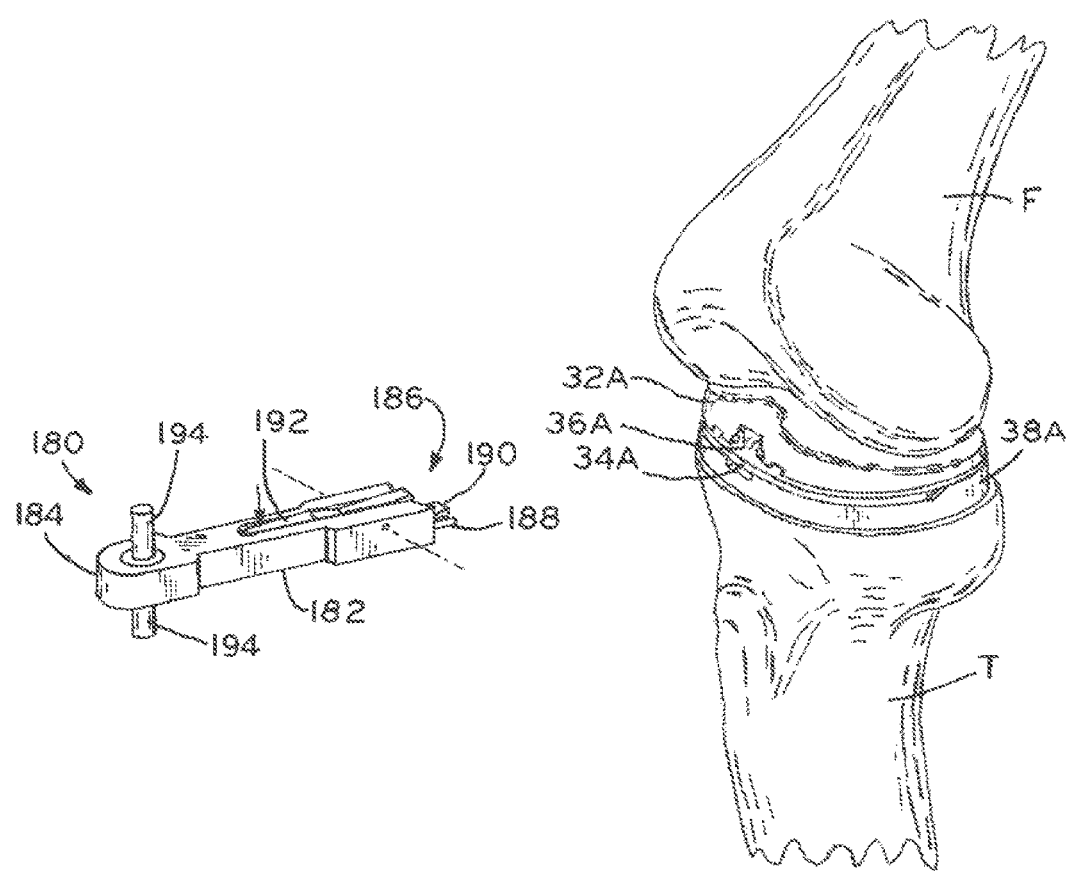
FIG. 8 is a perspective view of the provisional tibial prosthesis system of FIG. 6 illustrating the shim between the base component and the tibial bearing component.

In an exemplary embodiment, as illustrated in FIGS. 6-8, base component 34A is secured to tibial base plate 38A by positioning base component inferior surface 82A on base plate superior surface 150A. Undercut portion 108A. (shown in FIGS. 3B and 3C) of base component 34A is positioned within raised perimeter 158A (shown in FIG. 5) of base plate peripheral wall 156A. Raised perimeter 158A acts as a physical barrier to prevent base component 34A from significant relative movement relative to tibial base plate 38A in medial/lateral direction 22 and anterior/posterior direction 20. In this embodiment, base component 34A is movable relative to tibial base plate 38A in proximal/distal direction 24. In one embodiment, base component 34A is sized to have clearance with tibial base plate 38A, i.e., some movement between base component 34A and tibial base plate 38A in medial/lateral direction 22 and anterior/posterior direction 20 is allowable, but base component 34A and tibial base plate 38A are prohibited from disengagement in medial/lateral direction 22 and anterior/posterior direction 20.

In another exemplary embodiment, tibial bearing component 32A is positioned atop tibial base plate 38A. In such an embodiment, bearing inferior surface 42A (shown in FIG. 2C) of bearing component 32A is positioned within raised perimeter 158A of base plate peripheral wall 156A in a manner similar to the attachment between base component 34A and tibial base plate 38A discussed above. Raised perimeter 158A again acts as a physical barrier to prevent bearing component 32A from significant relative movement relative to tibial base plate 38A in medial/lateral direction 22 and anterior/posterior direction 20. In this embodiment, bearing component 32A is movable relative to tibial base plate 38A in proximal/distal direction 24. In one embodiment, bearing component 32A is sized to have clearance with tibial base plate 38A, i.e., some movement between bearing component 32A and tibial base plate 38A in medial/lateral direction 22 and anterior/posterior direction 20 is allowable, but bearing component 32A and tibial base plate 38A are prohibited from disengagement in medial/lateral direction 22 and anterior/posterior direction 20.

Referring to FIGS. 1-3C, the attachment of tibial bearing component 32A to base component 34A will now be described. Tibial bearing component 32A is positioned atop base component 34A by positioning protrusion 96A of base component 34A within bearing cavity 70A of tibial bearing component 32A and positioning nubs 104A of protrusion 96A respectively within bearing nub cavities 72A. In such an embodiment, base component 34A is locked to tibial bearing component 32A in medial/lateral direction 22 when protrusion 96A is received within bearing cavity 70A and base component 34A is locked to tibial bearing component 32A in anterior/posterior direction 20 when nubs 104A are respectively received within nub cavities 72A. The walls of bearing cavity 70A provide a physical barrier to prevent significant relative movement between base component 34A and tibial bearing component 32A in medial/lateral direction 22 and the walls of nub cavities 72A provide a physical barrier to prevent significant relative movement between base component 34A and tibial bearing component 32A in anterior/posterior direction 20. When tibial bearing component 32A is positioned atop base component 34A, tibial bearing component 32A is movable relative to base component 34A in proximal/distal direction 24. In this embodiment, as illustrated in FIGS. 6-8, base component 34A is secured to tibial base plate 38A and base component 34A is located between tibial bearing component 32A and tibial base plate 38A. In another embodiment, as discussed above, tibial bearing component 32A can be positioned directly atop tibial base plate 38A.

Figure 4A:
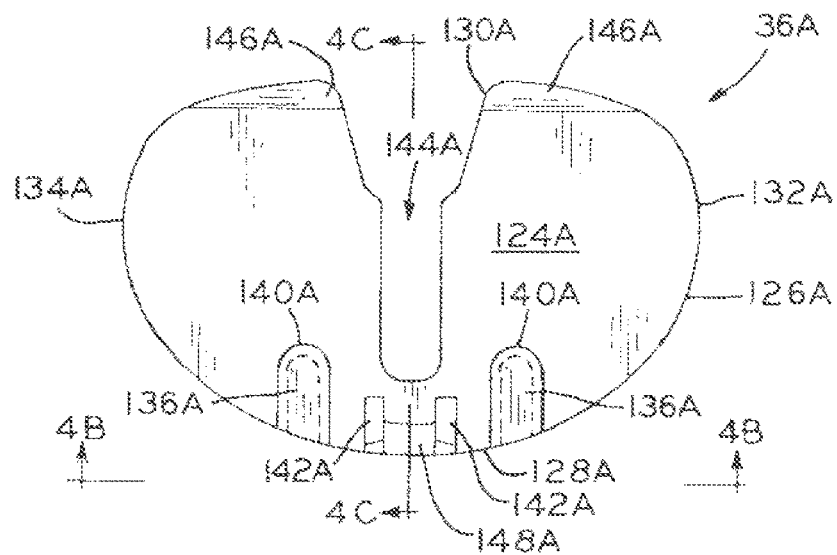
FIG. 4A is a plan view of a shim of the provisional tibial prosthesis system of FIG. 1.
Figure 4B:
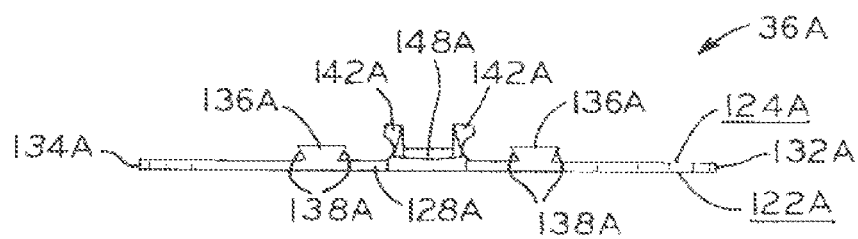
FIG. 4B is a front elevation view of the shim of FIG. 4A.
Figure 4C:
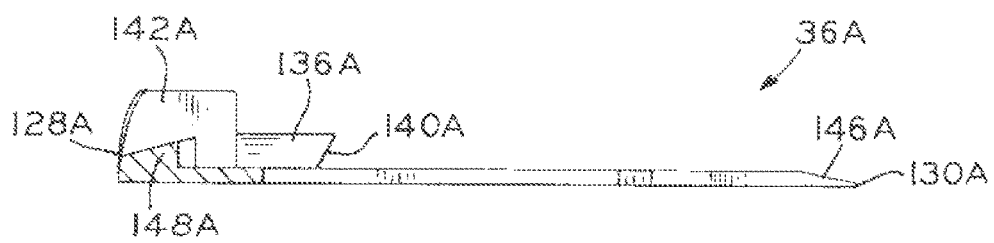
FIG. 4C is a cross-sectional view taken along line 4C-4C of FIG. 4A.

FIGS. 4A-4C illustrate shim 36A according to an exemplary embodiment of the present disclosure. Shim 36A generally includes shim inferior surface 122A, opposing shim superior surface 124A, and shim peripheral wall 126A extending from inferior surface 122A to superior surface 124A. Shim peripheral wall 126A defines a shim exterior profile. In one embodiment, the shim exterior profile substantially matches the tibial base plate exterior profile. Shim 36A also includes shim anterior side 128A, shim posterior side 130A, shim lateral side 132A, and shim medial side 134A. As shown in FIGS. 4A-4C, shim superior surface 124A includes rails 136A and handle alignment rails 142A. As illustrated in FIGS. 4A and 4B, rails 136A extend from anterior side 128A toward posterior side 130A parallel to anterior/posterior axis $A_{A-P}$ (shown in FIG. 6). In an exemplary embodiment, rails 136A have lead-in edges 140A and tapered walls 138A. Handle alignment rails 142A are located between rails 136A at anterior side 128A. Further, between handle alignment rails 142A is shim ramp 148A. Shim 36A also includes shim notch 144A and lead-in walls 146A, i.e., tapering posterior walls, at posterior side 130A for aligning shim 36A and guiding insertion of shim 36A in anterior/posterior direction 20, as will be further described below.

In an exemplary embodiment, a set of a plurality of shims 36A can be provided to allow for varying levels of adjustment of provisional tibial prosthesis system 30A, i.e., increasing the distance between tibial bearing component 32A and base component 34A by the shim height of a particular shim 36A inserted therebetween. For example, if four different sizes were to be used in the set of shims, the height of the shims could be 1 mm, 2 mm, 3 mm, and 4 mm. In another embodiment, a set of shims could include a plurality of shims having equal sizes for stacking shims. The stacking shims embodiment can also include a plurality of shims having varying heights. It is envisioned that the set of a plurality of different sized shims 36A could include any desired number of different sized shims having any number of shim heights.

During insertion of shim 36A, as best shown in FIGS. 6 and 7, lead-in walls 146A of shim 36A are placed between bearing component 32A and base component 34A and are used to affect separation of bearing component 32A from base component 34A by a distance along proximal/distal axis Atm) equal to a height of shim 36A. In this manner, lead-in walls 146A act as a ramp to separate bearing component 32A from base component 34A. Advantageously, the provisional tibial prosthesis system of the present disclosure can be adjusted in a manner requiring the knee joint to only be distracted by a distance equal to the height of shim 36A. In another embodiment, to further help separation of bearing component 32A from base component 34A, bearing component inferior surface 42A (shown in FIG. 2C) at bearing anterior side 48A (shown in FIGS. 2A-2C) can include a beveled edge corresponding to lead-in walls 146A of shim 36A.

As illustrated in FIGS. 6-8, in one exemplary embodiment, shim 36A is slidably receivable between tibial bearing component 32A and base component 34A in anterior/posterior direction 20. The insertion of shim 36A between tibial bearing component 32A and base component 34A in anterior/posterior direction 20 allows tibial bearing component 32A to only be separated from base component 34A by a distance along proximal/distal axis $A_{P,D}$ equal to the height of shim 36A. Also, tibial bearing component 32A and base component 34A of provisional tibial prosthesis system 30A do not have to be removed from the knee joint to insert and remove shims 36A.

In an alternative embodiment, base component 34A is not utilized and shim 36A is positioned between bearing component 32A and base plate 38A. In this embodiment, tibial bearing component 32A is positioned atop tibial base plate 38A such that bearing inferior surface 42A (shown in FIG. 2C) of bearing component 32A is positioned within raised perimeter 158A of base plate peripheral wall 156A. Referring to FIG. 5, in such an embodiment, the anterior rail of base plate 38A will be missing to allow shim 36A to be slidably receivable between tibial bearing component 32A and tibial base plate 38A in anterior/posterior direction 20 using lead-in walls 146A of shim 36A to separate tibial bearing component 32A from tibial base plate 38A by a distance along proximal/distal axis $A_{P,D}$ equal to a height of shim 36A. In this embodiment, shim 36A will have a perimeter configured to allow shim 36A to be positioned to the securement features of base plate 38A. For example, shim 36A will have a perimeter similar to the perimeter of base component 34A (shown in FIG. 3A).

As previously discussed, when tibial bearing component 32A is positioned atop base component 34A, tibial bearing component 32A is movable relative to base component 34A in proximal/distal direction 24. In the exemplary first embodiment, shim 36A takes away this last degree of freedom between tibial bearing component 32A and base component 34A, i.e., when shim 36A is received between base component 34A and tibial bearing component 32A, shim 36A locks tibial bearing component 32A to base component 34A in proximal/distal direction 24, i.e., significant relative movement between tibial bearing component 32A and base component 34A in proximal/distal direction 24 is prevented.

The manner in which shim 36A locks tibial bearing component 32A to base component 34A in proximal/distal direction 24 will now be discussed. Referring to FIGS. 6-8, shim 36A is inserted between tibial bearing component 32A and base component 34A in anterior/posterior direction 20. Referring to FIGS. 2A-2D and 4A-4C, and 6, shim rails 136A are aligned with respective tibial bearing component slots 64A. Referring to FIG. 4A, rails 136A each include lead-in edge 140A to guide insertion of rails 136A in slots 64A. The rail/slot connection between shim 36A and tibial bearing component 32A is important because it prevents lift-off of tibial bearing component 32A from shim 36A, i.e., prevents significant relative movement between tibial bearing component 32A and shim 36A in proximal/distal direction 24. In one exemplary embodiment, as shown in FIGS. 2A-2D and 4A-4C, slots 64A of tibial bearing component 32A and rails 136A of shim 36A each have a dovetail cross-sectional shape. Slots 64A including tapering walls 66A of bearing component 32A cooperate with rails 136A having tapering walls 138A of shim 36A to act as a physical barrier to prevent lift-off of the tibial bearing component 32A from shim 36A. In an alternate embodiment, slots 64A of tibial bearing component 32A and rails 136A of shim 36A can each have a T-shaped cross-sectional shape or other various shapes that would provide a physical barrier that would prevent lift-off, i.e., prevent significant relative movement between tibial bearing component 32A and base component 34A in proximal/distal direction 24, or any movement of tibial bearing component 32A in any direction that is perpendicular to base component 34A.

Referring to FIGS. 3A-4C, as shim 36A is inserted in anterior/posterior direction 20 between tibial bearing component 32A and base component 34A using lead-in walls 146A as discussed above, shim 36A also locks to base component 34A by shim notch 144A formed in shim posterior side 130A attaching to base component 34A by sliding notch 144A in indentations 102A between protrusion 96A and base component superior surface 84A. This shim connection between shim 36A and base component 34A and the rail/slot connection between shim 36A and tibial bearing component 32A allows shim 36A to lock tibial bearing component 32A to base component 34A in proximal/distal direction 24.

Referring to FIGS. 6-8, an illustrative procedure in accordance with the present disclosure to determine the size of a final tibial prosthesis for a prosthetic knee joint for implantation in a natural knee will now be described. In one embodiment, a surgeon selects a provisional tibial prosthesis system, such as provisional tibial prosthesis system 30A, having tibial base plate 38A (shown in FIG. 5) having bone contacting surface 152A and opposing base plate superior surface 150A, tibial bearing component 32A having a tibial bearing component height, tibial bearing component 32A attachable to tibial base plate 38A, and shim 36A having a shim height, shim 36A slidably receivable between tibial base plate 38A and tibial bearing component 32A in anterior/posterior direction 20 when tibial base plate 38A and tibial bearing component 32A are separated by a distance along proximal/distal axis $A_{P,D}$ equal to the shim height.

Next, the proximal portion of a patient's tibia is resected using standard surgical techniques to provide a substantially flat surface for receipt of bone contacting surface 152A of tibial base plate 38A. Once the proximal tibia is resected, tibial base plate 38A is implanted and secured to the resected proximal tibia. Subsequently, tibial bearing component 32A corresponding to the constraint level chosen by the surgeon is positioned atop tibial base plate 38A such that bearing inferior surface 42A (shown in FIG. 2C) of bearing component 32A is positioned within raised perimeter 158A (shown in FIG. 5) of base plate peripheral wall 156A. If base component 34A is utilized, base component 34A is positioned atop tibial base plate 38A between bearing component 32A and base plate 38A.

The surgeon can then perform range of motion testing of the knee joint to verify proper sizing of the provisional tibial prosthesis system. If a surgeon determines that a provisional tibial prosthesis system is properly sized with tibial bearing component 32A positioned atop tibial base plate 38A, a first final tibial prosthesis can be selected which corresponds to the height of tibial bearing component 32A. If the provisional tibial prosthesis system is determined to not be properly sized, tibial bearing component 32A can be spaced from tibial base plate 38A by sliding shim 36A having a first shim height, e.g., 1 mm, between tibial base plate 38A and tibial bearing component 32A in anterior/posterior direction 20.

The surgeon can then perform range of motion testing of the knee joint to verify proper sizing of the provisional tibial prosthesis system with shim 36A having a first shim height inserted between tibial bearing component 32A and tibial base plate 38A. If the provisional tibial prosthesis system is determined by the surgeon to be properly sized with shim 36A having first shim height between bearing component 32A and tibial base plate 38A, the surgeon can select a second final tibial prosthesis represented by the first shim height and the tibial bearing component height.

In one embodiment, if the provisional tibial prosthesis system is not properly sized after insertion of shim 36A having the first shim height, e.g., 1 mm, the 1 mm shim 36A can be removed in anterior/posterior direction 20, another shim 36A may be selected having a second height, e.g., 2 mm, and tibial bearing component 32A can then be spaced from tibial base plate 38A by sliding shim 36A having the second shim height between tibial base plate 38A and tibial bearing component 32A in anterior/posterior direction 20. If the provisional tibial prosthesis system is determined by the surgeon to be properly sized with shim 36A having second shim height, e.g., 2 mm, the surgeon can select a third final tibial prosthesis represented by the second shim height and the tibial bearing component height.

In an alternate embodiment, after inserting shim 36A having a first shim height, e.g., 1 mm, if a surgeon determines that the provisional tibial prosthesis system with shim 36A having the first shim height is not properly sized, shim 36A having a height of 1 mm can be left between tibial base plate 38A and tibial bearing component 32A, and a second shim 36A having a second shim height, e.g., 1 mm, can be inserted in anterior/posterior direction 20 between tibial base plate 38A and tibial bearing component 32A to separate tibial bearing component 32A from tibial base plate 38A by a distance along proximal/distal axis $A_{P,D}$ equal to the first shim height and the second shim height. In this embodiment, shim 36A may not include either the securement features discussed above that lock shim 36A to tibial bearing component 32A or the securement features discussed above that lock shim 36A to base component 34A. For example, referring to FIGS. 4A and 4B, shim 36A may not include rails 136A so that tibial bearing component 32A can move relative to shim 36A in proximal/distal direction 24 (shown in FIG. 6) when shim 36A is inserted between base plate 38A and bearing component 32A. In this manner, a second shim can be inserted in anterior/posterior direction 20 between base plate 38A and bearing component 32A with a first shim already positioned between base plate 38A and bearing component 32A.

If the provisional prosthesis system is determined by the surgeon to be properly sized with both shims 36A inserted, the surgeon can select a third final tibial prosthesis represented by the first shim height, the second shim height, and the tibial bearing component height. This stacking of the shims can be repeated using a variety of different sized shims and a variety of different numbered shims for a surgeon to determine the proper thickness of a provisional tibial prosthesis system. In an alternative embodiment, several shims all having the same height can be used in series to adjust the spacing of bearing component 32A from base plate 38A.

Referring to FIGS. 6-8, the use of surgical instrument 180 to insert shim 36A will now be described. FIGS. 6-8 illustrate surgical instrument 180 for insertion or removal of shim 36A. Surgical instrument 180 generally includes handle body 182, handle end 184, opposing attachment end 186, alignment pins 188, tooth 190, button 192, and handle pegs 194. Surgical instrument 180 has one alignment pin 188 on each side of tooth 190. Alignment pins 188 fit in respective exterior circular recesses in rails 142A (shown in FIG. 4B) of shim 36A to properly align surgical instrument 180 to shim 36A. Once properly aligned, tooth 190 of surgical instrument 180 slides along shim ramp 148A (shown in FIGS. 4A and 4B) and, when tooth 190 slides past shim ramp 148A, a biasing force on tooth 190 causes tooth 190 to travel downward and engage the backside of shim ramp 148A to lock surgical instrument 180 to shim 36A. In one embodiment, a biasing force is exerted on tooth 190 by a tension spring. When surgical instrument 180 is properly locked to shim 36A, a surgeon holding handle end 184 of surgical instrument 180 can insert shim 36A in anterior/posterior direction 20 between tibial bearing component 32A and tibial base plate 38A to space tibial bearing component 32A from tibial base plate 38A along proximal/distal axis $A_{P,D}$ a distance equal to the shim height. Once shim 36A is properly inserted between tibial bearing component 32A and tibial base plate 38A, release button 192 of surgical instrument 180 can be depressed to overcome the biasing force of the spring to release and disengage tooth 190 from the backside of shim ramp 148A. Thereafter, surgical instrument 180 can be removed. In another embodiment, surgical instrument 180 can be used in the manner described above to insert shim 36A in anterior/posterior direction 20 between tibial bearing component 32A and base component 34A. Also, surgical instrument 180 may be used to remove shim 36A from between tibial bearing component 32A and base component 34A.

Once the proximal portion of a patient's tibia is resected and the tibial prosthesis components of the present disclosure are secured to the resected proximal tibia, soft tissue balancing of the knee can be performed. Subsequently, a sizing guide can be attached to the tibial prosthesis components. Similar to the attachment of surgical instrument 180 to shim 36A, the sizing guide can include alignment pins that fit in respective exterior circular recesses in rails 142A (shown in FIG. 4B) of shim 36A to properly align the sizing guide to shim 36A. Once properly aligned, a locking component of the sizing guide can slide along shim ramp 148A (shown in FIGS. 4A and 4B) and, when the locking component slides past shim ramp 148A, a biasing force on the locking component can cause the locking component to travel downward and engage the backside of shim ramp 148A to lock the sizing guide to shim 36A. Similarly, a cut guide such as a femoral finishing cut guide can be attached to shim 36A.

Figure 9:
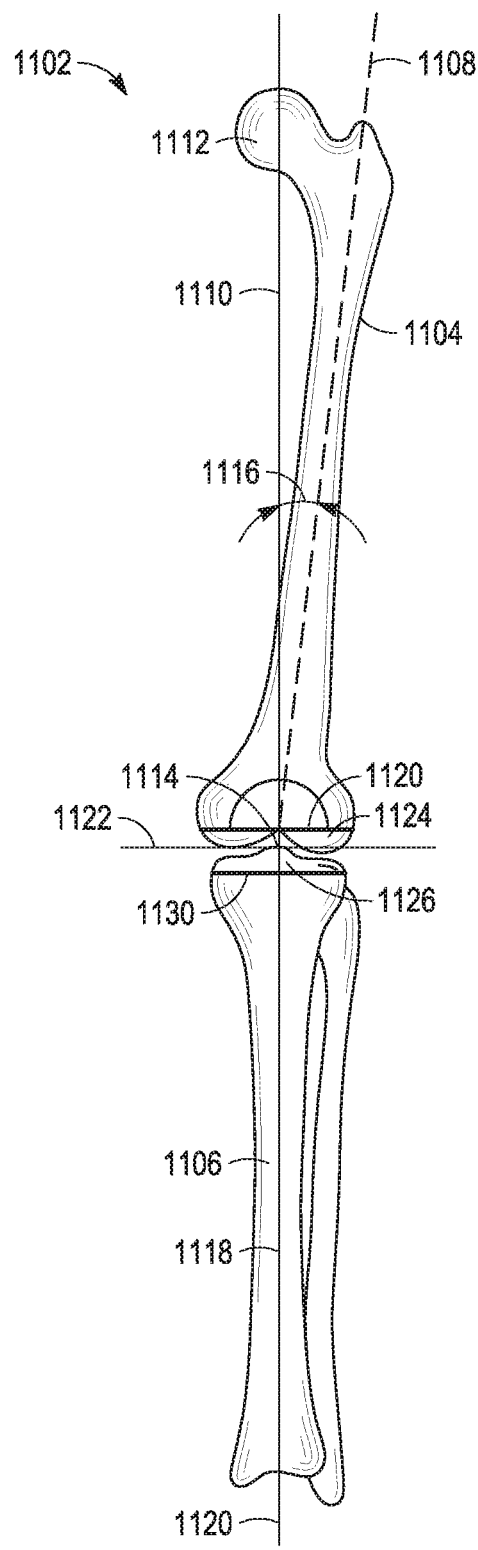
FIGS. 9-10 illustrate knee joint structures providing suitable environments in which a tibial prosthesis system, as constructed in accordance with at least one embodiment, can be used.
Figure 10:
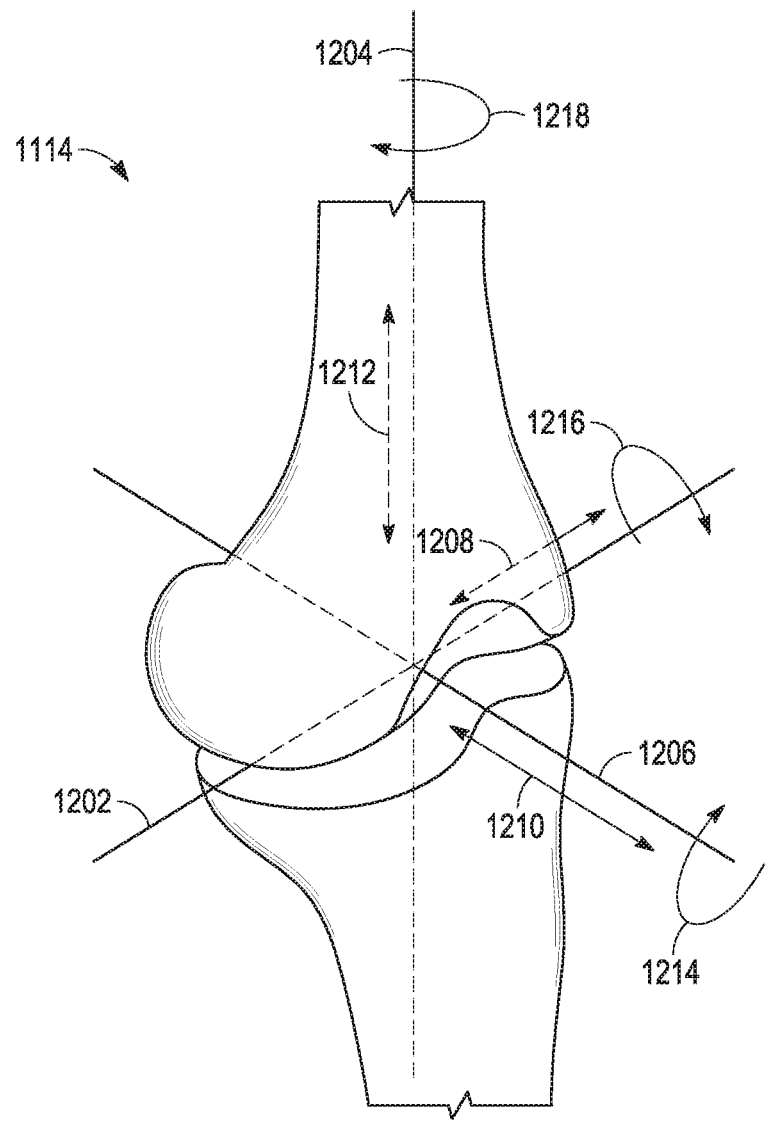

To better understand knee joint replacement procedures, it can be helpful to understand the relationship of bones and bone cuts that can be made to orient various provisional and permanent prosthesis components within a knee joint. FIGS. 9 and 10 illustrate several features of knee joint structures and orientations. In FIG. 9, a frontal view of a lower limb 1102, including a femur 1104 and a tibia 1106, is shown to illustrate various lower limb axes. The femur 1104 has an anatomic axis 1108 that coincides generally with its intramedullary canal. The femur 1104 also has a mechanical axis 1110, or load axis, running from the center of a femoral head 1112 to the center of a knee joint 1114. The angle 1116 extending between these two axes varies among the patient population, but is generally on the order of between 5-7 degrees, inclusive. Like the femur 1104, the tibia 1106 also has an anatomic axis coinciding generally with its intramedullary canal. The mechanical axis 1118 of the tibia 1106 runs from the center of the knee joint 1114 to the center of an ankle region 1120 and is generally collinear with its anatomic axis.

A joint line 1122, about which the knee joint 1114 flexes, is approximately parallel to a line through medial and lateral femoral condyles 1124 and to a tibial plateau 1126. Although illustrated as perpendicular in FIG. 9, the joint line 1122 can extend at a varus or valgus angle relative to the mechanical axes 1110 and 1118 of the femur 1104 and tibia 1106, respectively. Normally, during a partial or total knee replacement procedure, portions of a distal end of the femur 1104 or a proximal end of the tibia 1106 are resected to be parallel or approximately parallel to the joint line 1122, and thus perpendicular to the mechanical axes 1110 and 1118, as indicated at 1128 and 1130, respectively.

FIG. 10 illustrates a closer view of the knee joint 1114 and its coordinate system, in which a medial/lateral axis 1202 corresponds approximately to the joint line 1122 (FIG. 9), a proximal/distal axis 204 corresponds approximately to the mechanical axes 1110 and 1118 (FIG. 9), and an anterior/posterior axis 1206 is approximately normal to the other two axes. Position along each of these axes can be depicted by arrows, which can represent the medial/lateral 1208, anterior/posterior 1210, and proximal/distal 1212 positioning of inserted prosthesis components. Rotation about each of these axes can also be depicted by arrows. Rotation about the proximal/distal axis 1204 can correspond anatomically to external rotation of a femoral component, while rotation about the anterior/posterior axis 1206 and medial/lateral axis 1202 can correspond to extension plane slope and varus/valgus angle of a component, respectively. Depending on a position of the proximal tibial cut 1130 (FIG. 9) made, a varus/valgus angle 1214, extension plane angle 1216, external rotation 1218, or joint extension gap can be affected. Similarly, a position of the distal femoral cut 1128 (FIG. 9) can affect the location of the joint line 1122, the extension gap, the varus/valgus angle 1214, or the extension plane angle 1216.

Figure 11:
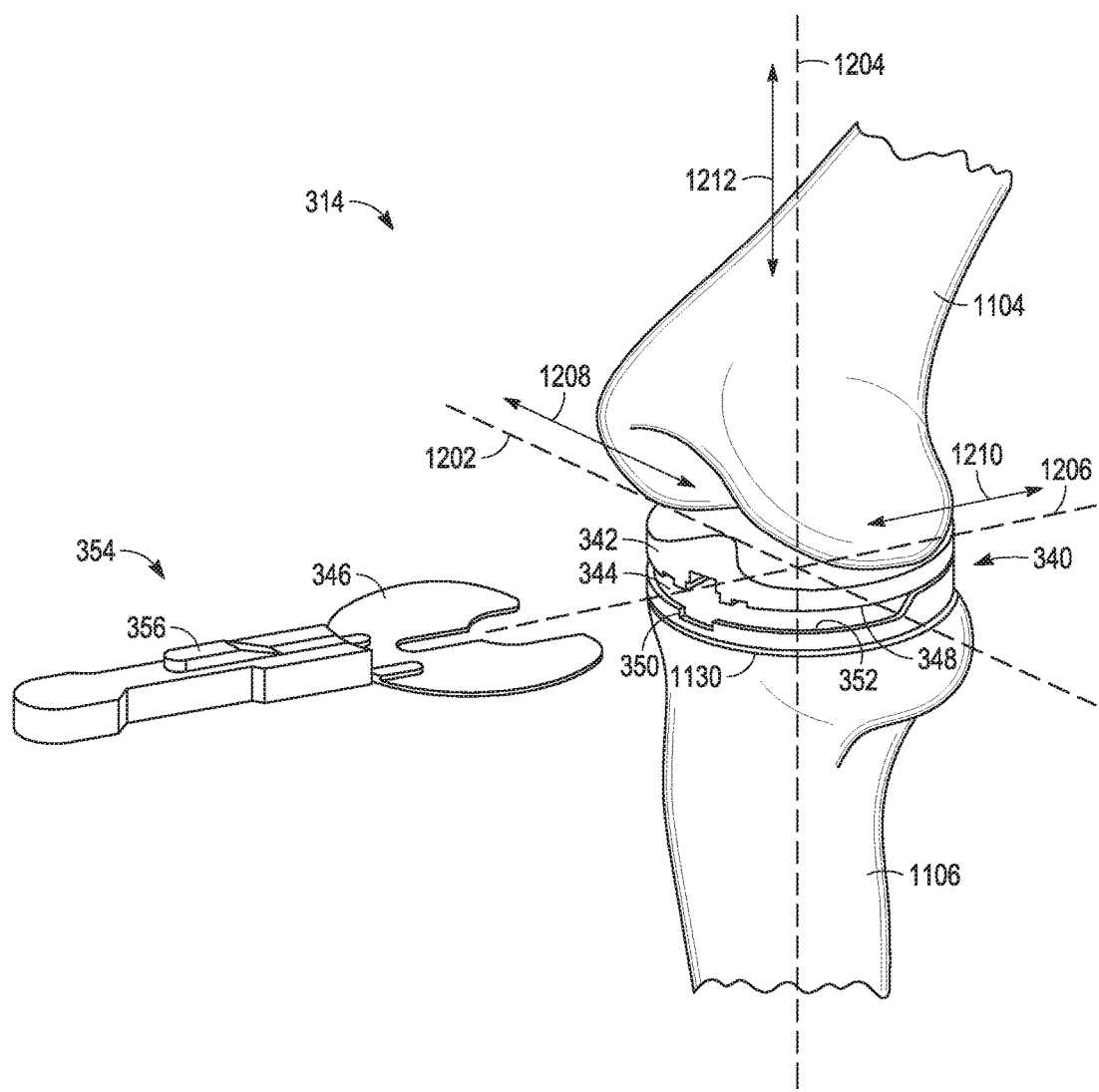
FIG. 11 illustrates a partially resected knee joint structure and a tibial prosthesis system, as constructed in accordance with at least one embodiment.

FIG. 11 illustrates a partially resected knee joint 314 structure, including a proximal tibial cut 130, and a provisional tibial prosthesis system 340. The provisional tibial prosthesis system 340 can include a bearing component 342, a base component 344, a plate component 350, and a shim component 346 insertable between an inferior surface 348 of the bearing component 342 and a superior surface 352 of the base component 344. The shim component 346 can include one or both of a medial edge having a different height than a lateral edge or an anterior edge having a different height than a posterior edge and can be used as a height varying spacer block between the bearing component 342 and the base component 344. The spacing of the bearing component 342 from the base component 344, for example, is adjustable to allow for representation of a variety of different sized angled bone cuts that can be made to a femur 1104 or a tibia 1106 or permanent tibial prosthesis systems. The shim component 346 can be inserted between the inferior surface 348 of the bearing component 342 and the superior surface 352 of the base component 344 using a shim handling instrument 354. The shim handling instrument 354 can include a release means 356 to disengage the shim component 346 after its insertion between the bearing 342 and base 344 components.

Figure 12A:
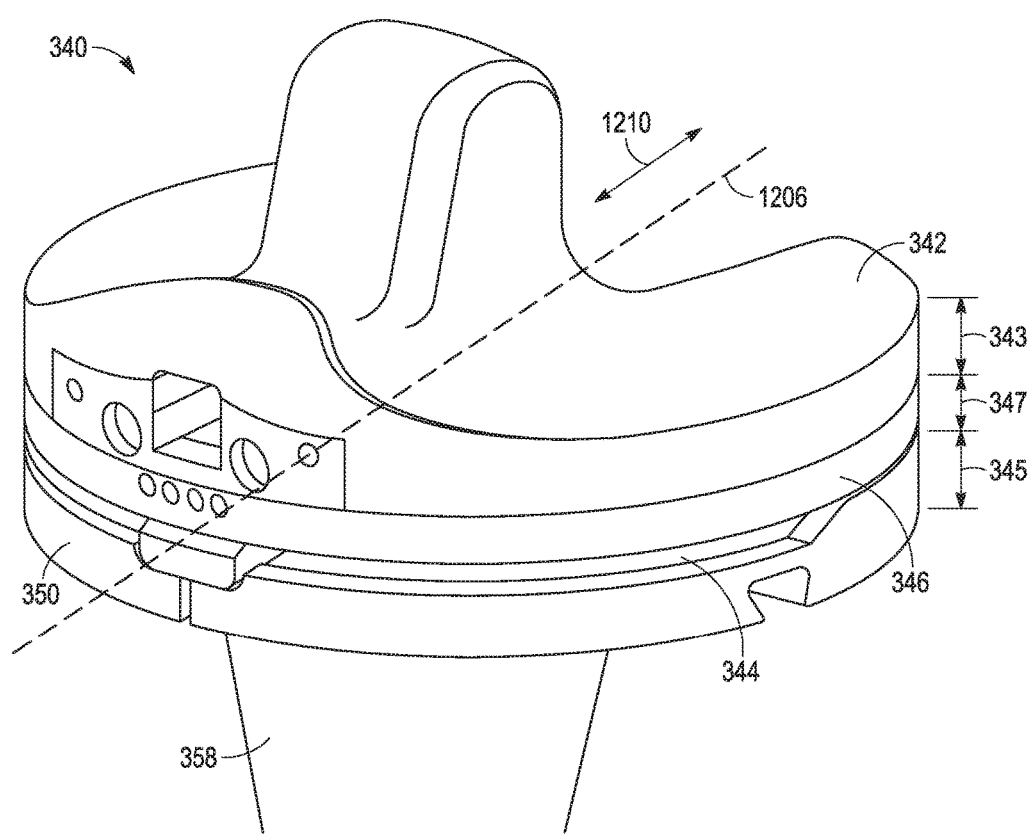
FIGS. 12A-12B respectively illustrate assembled and component views of a tibial prosthesis system, as constructed in accordance with at least one embodiment.
Figure 12B:
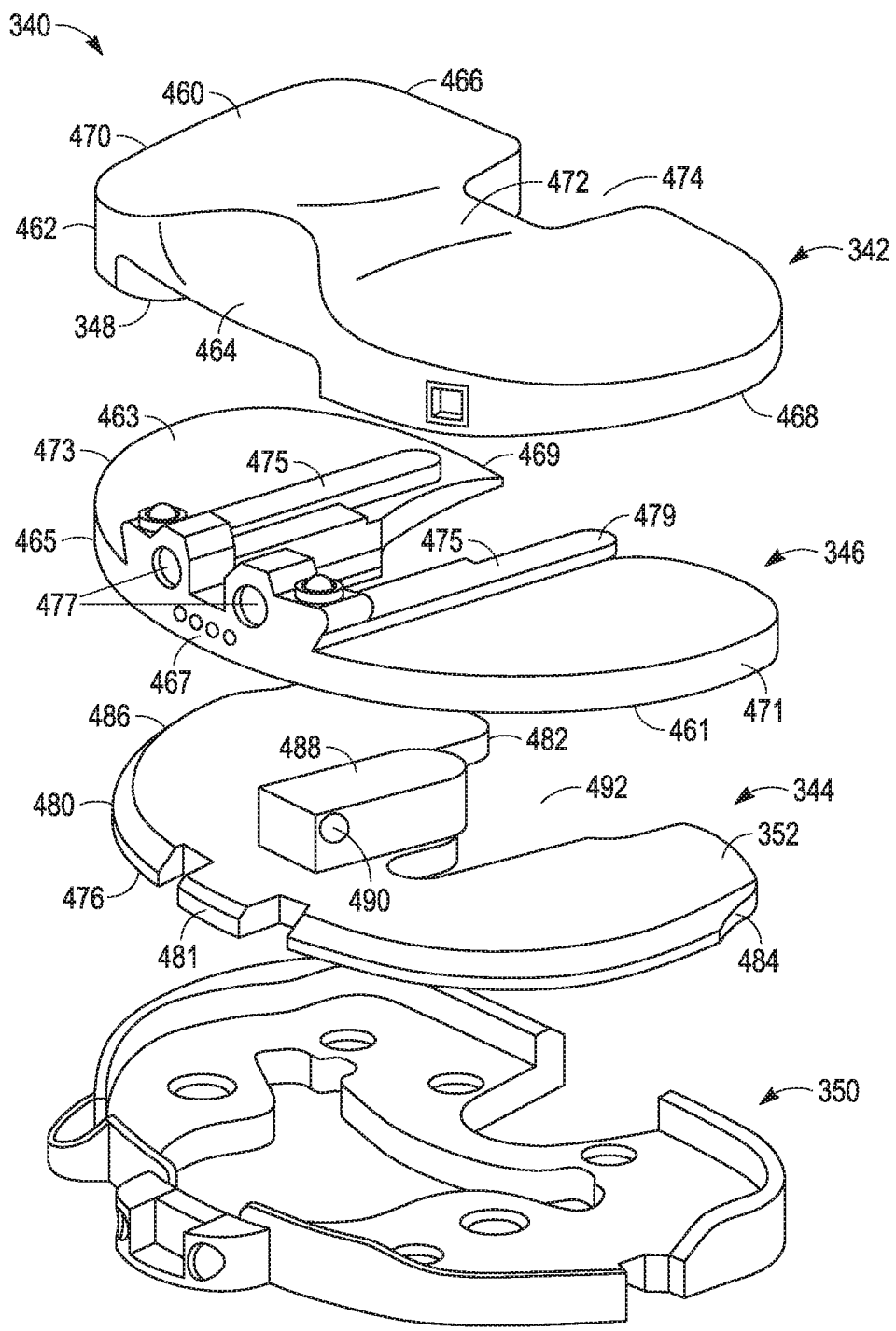

FIGS. 12A and 12B respectively illustrate assembled and component views of a provisional tibial prosthesis system 340. The provisional tibial prosthesis system 340, or components thereof, can be used to mimic geometry of one or both of an angle bone cut to be made or a permanent tibial prosthesis system. For example, the assembled tibial prosthesis system 340 of FIG. 12A, illustrates a bearing component 342, a shim component 346, a base component 344, and a plate component 350. A stem component 358 can be attached to the plate component 350 and used to secure the plate component 350 to a resected tibia 106 (FIG. 11).

Each component of the provisional tibial prosthesis system 340 includes an associated height. A shim component height 347 can be combined with a bearing component height 343 and a base component height 345, for example, to represent a desired height of a permanent tibial prosthesis system. A plurality of different or varying sized shims 346 can be slidably inserted between the bearing component 342 and a bearing support component, such as the base component 344, in an anterior/posterior 210 direction. Advantageously, the different or varying sized shims 346 can be inserted and removed without removing the bearing component 342 or the bearing support component from within a knee joint 314 (FIG. 11). Instead, all that is needed is a distraction of the knee joint 314 in an amount equal or approximately equal to the height profile of a particular shim component 346. In one example, the shim handling instrument 354 can be used to engage one or more handling alignment voids of a shim component 346 to assist in inserting and removing the shim component 346 between the bearing component 342 and the bearing support component 344. The one or more handling alignment voids of the shim component 346 can be consistent over the broad range of different sized shim components for universal compatibility with the shim handling instrument 354.

Each component of the provisional tibial prosthesis system 340 can include a structure defined by various surfaces, voids, or cavities. As shown in FIG. 12B, the bearing component 342, for example, can include an inferior surface 348, an opposing superior surface 460, and a peripheral wall 462 extending from the inferior surface 348 to the superior surface 460. The bearing component 342 can further include an anterior side 464, a posterior side 466, a lateral side 468, and a medial side 470. The superior surface 460 can be configured to articulate with natural or prosthetic condyles of a distal femur and can include a bearing lateral particular surface portion and a bearing medial particular surface portion, with a central tibial eminence 472 disposed between the particular surface portions. The inferior surface 348 can include a bearing cavity and one or more bearing nub cavities. The bearing cavity can extend from the inferior surface 348 toward the superior surface 460 and can be sized and shaped to accept a projection of the base component 344. The bearing nub cavities can extend on opposing sides of the bearing cavity and can each be sized and shaped to receive a nub located on the projection of the base component 344.

A posterior cruciate ligament (PCL) cutout 474 can be disposed at the posterior side 466 between the particular surfaces. The PCL cutout 474 can be sized and positioned to correspond with a PCL of the knee joint 314. In the example of FIG. 12B, the bearing component 342 is illustrated as a cruciate retaining bearing component, although it is contemplated that other tibial bearing components can be used. Bearing components that cooperate to form a posterior stabilized prosthesis, as shown in the example of FIG. 12A, or a knee prosthesis having an intermediate level of constraint between a posterior stabilized and cruciate retaining prosthesis are within the scope of the present disclosure. The bearing component 342 can also be made available in a variety of shapes and sizes to accommodate a variety of patient knee joints.

The base component 344 can include an inferior surface 476, an opposing superior surface 352, and a peripheral wall 480 extending from the inferior surface 476 to the superior surface 352. The base component 344 can further include an anterior side 481, a posterior side 482, a lateral side 484, and a medial side 486. A projection 488, including one or more nubs 490, can extend from the superior surface 352. The projection 488 and nubs 490 can be configured to be received within, and couple to, the bearing and bearing nub cavities of the bearing component 342. The base component 344 can include one or more of a W-shaped notch 492 at the posterior side 482, an undercut portion to mate with a raised perimeter of the plate component 350, a medial side groove, and a lateral side groove.

The bearing component 342 and the base component 344 can be coupled to or engaged with each other. In an example, the bearing component 342 can be positioned atop of the base component 344 and the projection 488, including the one or more nubs 490, of the base component 344 can be positioned within the bearing and bearing nub cavities of the bearing component 342. The base component 344 can be secured to the bearing component 342 in a medial/lateral direction 1208 (FIG. 10) when the projection 488 is received with the bearing cavity and can be secured in an anterior/posterior direction 1210 (FIG. 10) when the one or more nubs 490 are received with respective nub cavities. The walls of the bearing cavity can provide a physical barrier to inhibit significant relative movement between the base component 344 and the bearing component 342 in the medial/lateral direction 208. Similarly, the walls of the bearing nub cavities can provide a physical barrier to inhibit significant relative movement between the base component 344 and the bearing component 342 in the anterior/posterior direction 1210. When the bearing component 342 is positioned atop the base component 344, and before insertion of the shim component 346, the bearing component can 342 be movable relative to the base component 344 in a proximal/distal direction 1212 (FIG. 10).

The base component 344 can be secured to the base plate 350, such that the base component 344 is located between the bearing component 342 and the base plate 350.

Turning again to FIG. 12B, the shim component 346 can include an inferior surface 461, an opposing superior surface 463, and a peripheral wall 465 extending from the inferior surface 461 to the superior surface 463. The peripheral wall 465 can define an exterior profile of the shim component 346. In an example, the exterior profile of the shim component 346 can substantially match an exterior profile of the base component 344 or the plate component 350. The shim component 346 can further include an anterior side 467, a posterior side 469, a lateral side 471, and a medial side 473.

The superior surface 463 can include one or more rails 475 and one or more handling alignment voids 477. The one or more rails 475 can be configured to slidably engage one or more slots on the inferior surface 348 of the bearing component 342. The rails 475 can extend from the anterior side 467 toward the posterior side 469, such in an orientation parallel to the anterior/posterior direction 210. The rails 475 can include lead-in edges 479 to facilitate alignment and engagement with the slots of the bearing component 342. The rail 475/slot engagement between the shim component 346 and the bearing component 342 can inhibit lift-off the bearing component 342 from the shim component 346. The one or more handling alignment voids 477 can be configured to engage with an interface of a shim handling instrument, such as is shown in FIG. 12A.

A set of different sized shim components 346 can be provided in a kit or system to allow for varying levels of adjustment of the provisional tibial prosthesis system 340 and insight into knee joint kinematics if certain bone cuts are made to a tibia 1106 (FIG. 9) or a femur 1104 (FIG. 9). Particularly, the distance between the bearing component 342 and the base component 344 can be increased or decreased by inserting and removing different sized shim components 346. At least one of the shim components 346 can include one or both of a medial edge having a different height than a lateral edge or an anterior edge having a different height than a posterior edge. The medial edge height and the lateral edge height can be sized such that the inferior surface 461 of the shim component 346 includes a medial to lateral angle of between +3 degrees and −3 degrees, inclusive. The anterior edge height and the posterior edge height can be sized such that the inferior surface 461 of the shim component 346 includes an anterior to posterior angle of between +3 degrees and −3 degrees, inclusive. Two or more shim components 346 from the set can, in an example, be stacked to achieve desirable knee joint kinematics. It is believed that the set of different sized shim components 346 can include any desired number of shims having a constant or differing height.

Figure 13:
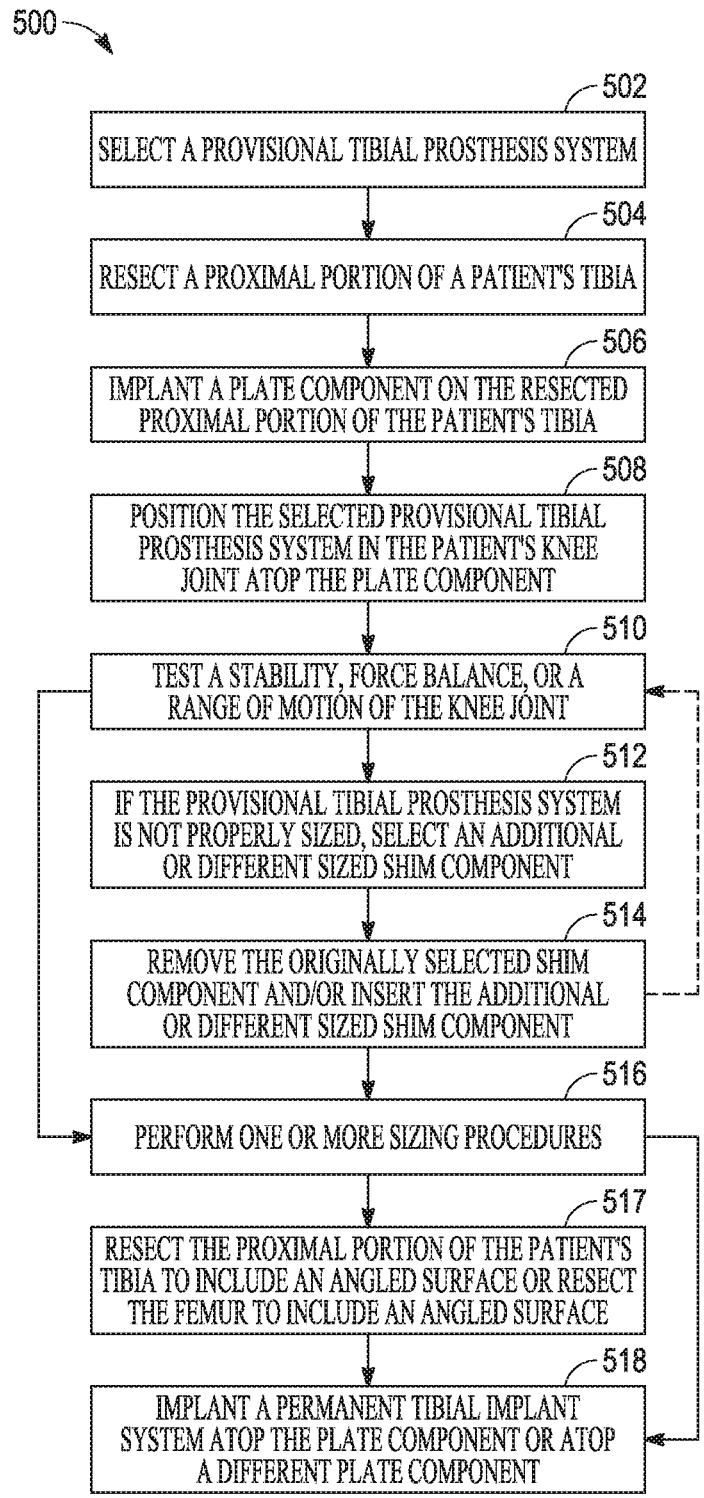
FIG. 13 illustrates a method of using a tibial prosthesis system, as constructed in accordance with at least one embodiment.

FIG. 13 illustrates a method 500 of using a provisional tibial prosthesis system to determine a proper angle of a bone cut to be made, if any, and an appropriate size (e.g., height) for a permanent tibial prosthesis system in a knee joint. At 502, a surgeon or other caregiver selects a particular size of the provisional tibial prosthesis system believed to be suitable for a patient. The provisional tibial prosthesis system can include a bearing member, a bearing support component, comprising one or both of a base component or a plate component, and a shim component. The plate component can include an inferior surface configured to contact a resected portion of a tibia and an opposing superior surface. The base component can include a base component height and be attachable to the plate component. The bearing component can include a bearing component height, and the shim component can include a shim component height. The shim component can be configured to be slidably received between the bearing component and the bearing support component in an anterior/posterior direction.

At 504, a proximal end portion of the patient's tibia is resected to be parallel or approximately parallel to a joint line of a knee. The tibia can be resected using standard surgical techniques to provide a substantially flat surface for receipt of the inferior, bone contacting surface of the plate component. Once the proximal end portion of the tibia is resected, the plate component can be implanted and secured to the resected tibia, at 506.

At 508, one or more of the selected bearing, shim, and base components can be positioned atop the plate component. In an example, the selected bearing and base components can initially be positioned atop the plate component, and subsequently, the selected shim component can be inserted between the bearing and base components in the anterior/posterior direction. The inserted shim component can include one or both of a medial edge having a different height than a lateral edge or an anterior edge having a different height than a posterior edge to counterbalance a deficiency (e.g., varus, valgus, anterior/posterior, or posterior/anterior sloping) of the knee joint.

At 510, the surgeon can perform one or more of a stability, a force balance, or a range of motion test of the knee joint to determine whether proper joint kinematics are present. The testing can include sensing at least one of a pressure, force, or position of the knee joint using a sensor coupled to or integrated with a provisional component. If the surgeon determines that proper knee joint kinematics is present, sizing procedures can begin, at 516. The sizing procedures can include determining whether an angled bone cut to the tibia and/or femur (e.g., a bone cut that is not parallel to the joint line of the knee) is needed, at 517, such as to counterbalance the knee joint deficiency, or determine the height of the provisional tibial prosthesis system. The angled bone cut to the tibia and/or femur can correspond to a height profile of the selected shim. The sizing procedures can use a sizing guide including alignment pins that fit in respective exterior voids in one or more provisional components to properly align the sizing guide to the components. Once properly aligned, a locking component of the sizing guide can slide along a shim ramp, for example, and, when the locking component slides past the shim ramp, a biasing force on the locking component can cause the locking component to travel downward and engage a backside of shim ramp to lock the sizing guide to the shim component.

At 512, if the provisional tibial prosthesis system is determined to not be properly sized due to improper joint kinematics being present, an additional or different sized shim component can be selected. At 514, the originally selected shim component can be removed from between the bearing component and the bearing support component and/or the newly selected shim component can be inserted between the bearing component and the bearing support component. The newly selected shim component can include at least one of a medial edge, a lateral edge, an anterior edge, or a posterior edge having a different height than the originally selected shim component. Insertion and removal of the shim components can be achieved in the anterior/posterior direction using a shim handling instrument. The bearing and bearing support components can be configured and coupled to each other in such a way that removal or insertion of shim components does not disturb the coupling arrangement.

With the newly selected shim component in place, the surgeon can again perform one or more of a stability, a force balance, or a range of motion test of the knee joint, at 510, to determine whether proper joint kinematics are present. Shim component replacement or stacking can be repeated, using a variety of different or similarly sized shims and a variety of different numbers of shims, until the surgeon determines that proper joint kinematics are present.

Finally, at 518, a permanent tibial prosthesis system can be selected and implanted. The permanent tibial prosthesis system can include a height that corresponds to the height of one or more provisional tibial prosthesis system components.

Figure 14A:
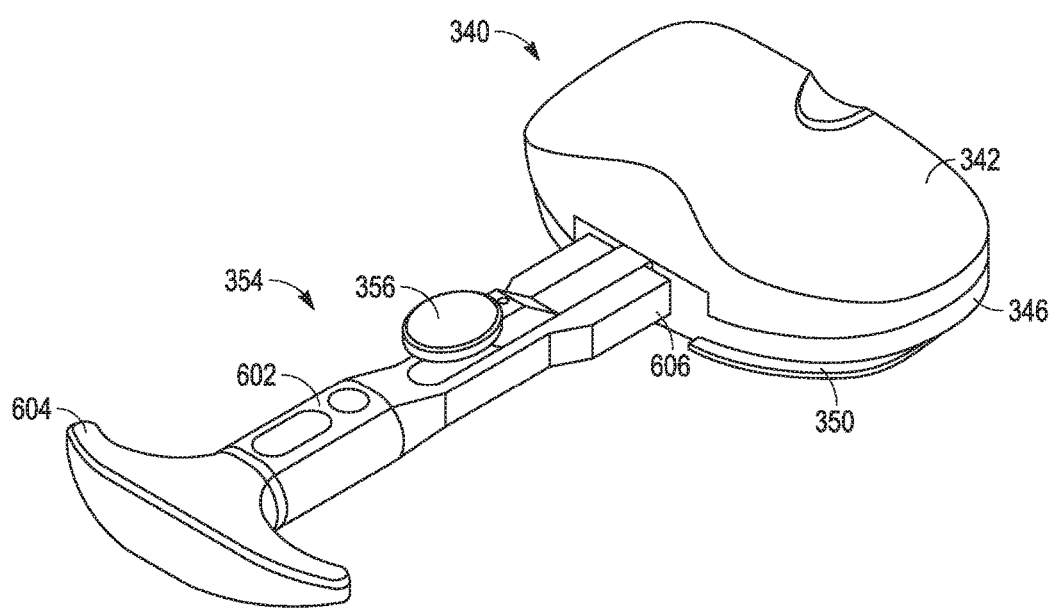
FIG. 14A-14B respectively illustrate assembled and component views of a tibial prosthesis system and a shim handling instrument, as constructed in accordance with at least one embodiment.
Figure 14B:
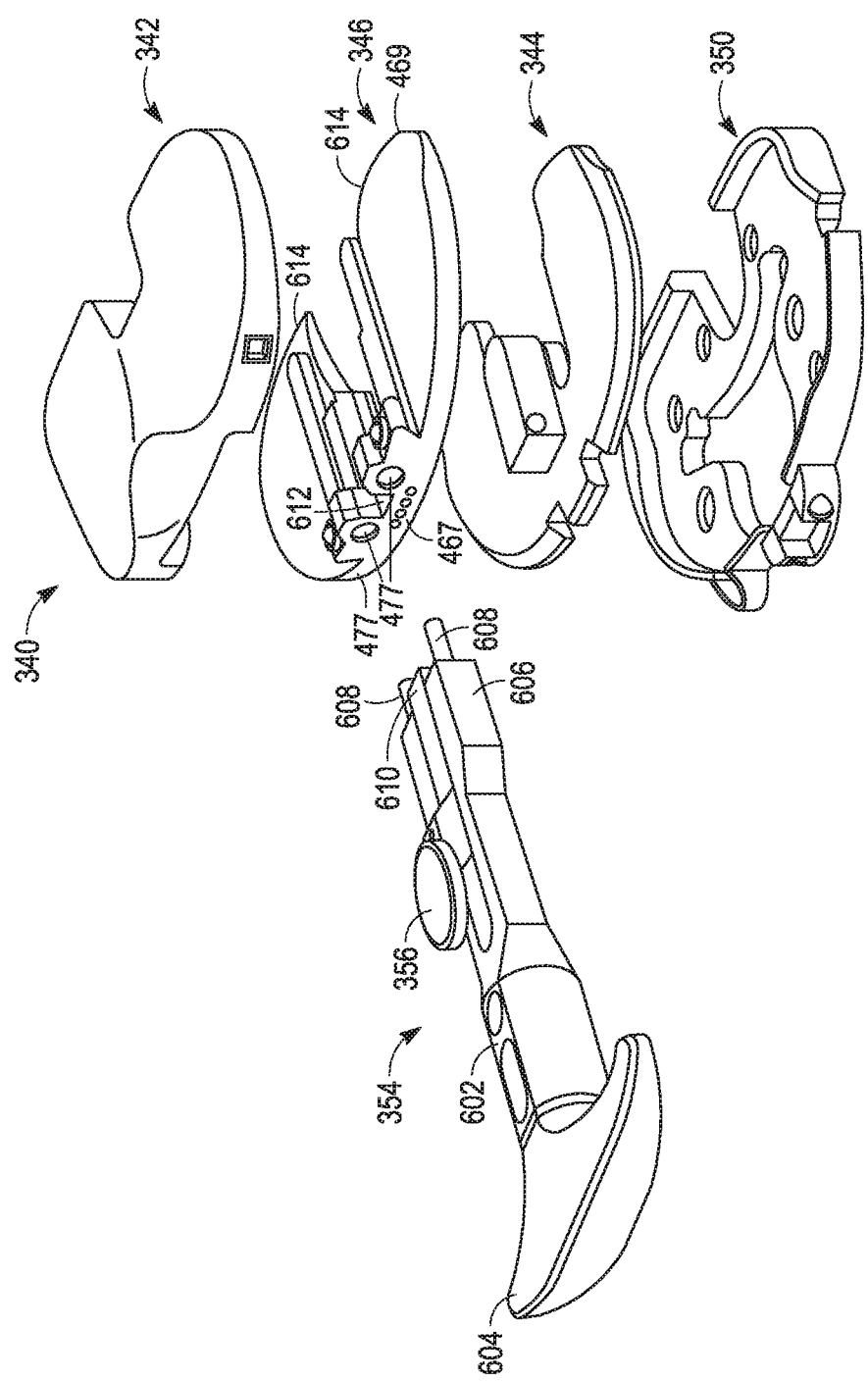

FIGS. 14A and 14B respectively illustrate assembled and component views of a provisional tibial prosthesis system 340 and a shim handling instrument 354 attachable to a shim component 346 of the system. As discussed with respect to FIG. 13, above, the shim handling instrument 354 can be used for insertion or removal of different sized shim components 346. The shim handling instrument 354 can include, among other things, a handle body 602, a user-engageable end 604, an opposing attachment end 606, one or more alignment pins 608, release means 356 (e.g., a release button), and an engageable tooth 610. The one or more alignment pins 608 can be positioned on each side of the engageable tooth 610. The alignment pins 608 can be configured to fit into respective handling alignment voids 477 positioned near an anterior side 467 of the shim component 346.

When the shim handling instrument 354 and the shim component 346 are properly aligned, the engageable tooth 610 can be configured to slide along a shim ramp 612. When the engageable tooth 610 slides along the shim ramp 612, a biasing force on the engageable tooth 610 can cause the tooth to travel downward and engage a backside of the shim ramp 612, thereby locking the shim handling instrument 354 to the shim component 346. The biasing force can be exerted on the engageable tooth 610 by a tension spring.

When the shim handling instrument 354 is locked to the shim component 346, a surgeon holding the user-engageable end 604 of the shim handling instrument 354 can insert the shim component 346 between a bearing component 342 and a bearing support component, such as one or both of a base component 344 or a plate component 350, in an anterior/posterior direction 1210 (FIG. 10). The insertion of the shim component 346 can space the bearing component 342 from the bearing support component a distance equal to the shim component height 347 (FIG. 12A) along a proximal/distal axis 1204 (FIG. 10). During insertion of the shim component 346, an entry ramp 614 on a posterior side 469 of the shim component 346 can be used to urge, in a ramp-like manner, separation of the bearing component 342 and the bearing support component. Once the shim component 346 is fully inserted between the bearing component 342 and the bearing support component, the release means 356 can be depressed to overcome the downward biasing force on the engageable tooth 610. In this way, the engageable tooth 610 can be disengaged from the backside of the shim ramp 612 and the shim handling instrument 354 can be disengaged from the shim component 346. In a similar manner, the shim handling instrument 354 can be used to remove the shim component 346 from between the bearing component 342 and the bearing support component.

Figure 18:
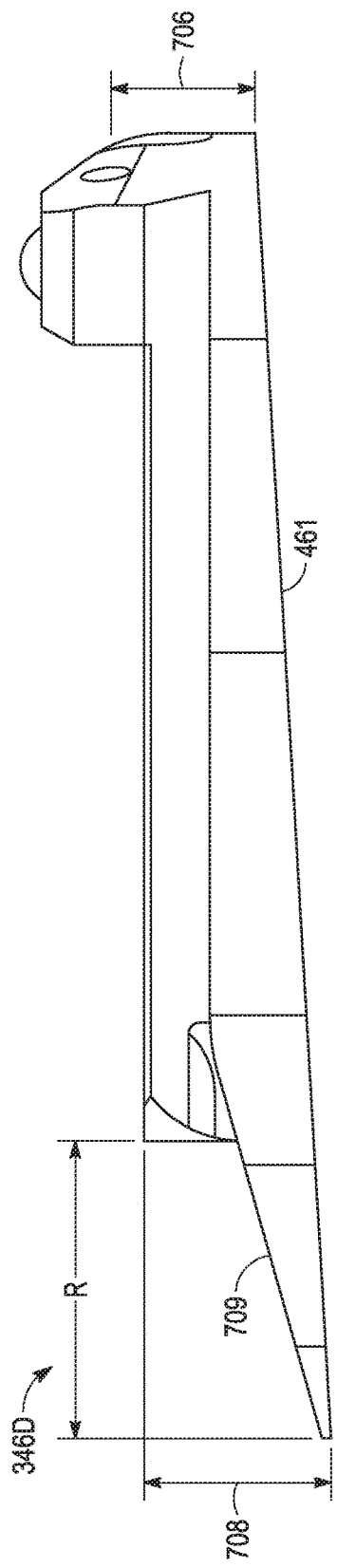

Advantageously, the present provisional tibial prosthesis system 340 can be adjusted in a manner requiring a knee joint 1114 (FIG. 10) to only be distracted by a distance equal to a height profile of the shim component 346. The shim components 346, as shown in FIGS. 16 and 18, can include one or both of a medial edge having a different height than a lateral edge or an anterior edge having a different height than a posterior edge. Differing height shim components 346 can advantageously provide a surgeon with joint kinematic insight regarding an angled bone cut before the cut is made, and can reduce the number of provisional components needed during surgery sizing by offering tailored separation between knee joint components. Also, the bearing component 342 and the bearing support component, such as the base component 344, do not have to be removed from the knee joint 114 to insert and remove shim components 346.

FIGS. 15 and 16 illustrate front views of at least two versions of a shim component of a provisional tibial prosthesis system. The shim component 346A of FIG. 15 includes a medial edge height 702 that is the same or substantially the same as a lateral edge height 704. In contrast, the shim component 346B of FIG. 16 includes a medial edge height 702 that is different than a lateral edge height 704. In the example shown, the medial edge height 702 is greater than the lateral edge height 704 and can be used by a surgeon to analyze possible bone cuts for a patient experiencing a varus (or bow-legged) knee joint. Alternatively, the medial edge height 702 can be less than the lateral edge height 704 and can be used by a surgeon to analyze possible bone cuts for a patient experiencing a valgus (for knock-kneed) joint. Due to a height difference between the medial and lateral edges, an inferior surface 461 of the shim component can include a medial to lateral angle of between +3 degrees and −3 degrees, inclusive. The wedge-like shape of the shim component 346B can be used by the surgeon to assess kinematics of a knee joint if a particular bone cut is made. In this way, the wedge-like shape can be used as a feedback mechanism.

In some examples, the medial edge height 702 or the lateral edge height 704 can provide between 10 mm and 20 mm, inclusive, of spacing adjustment between a bearing component 342 (FIG. 12A) and a bearing support component, such as a base component 344 (FIG. 12A) or a plate component 350 (FIG. 12A). In some examples, the medial edge height 702 or the lateral edge height 704 can provide between 10 mm and 14 mm, inclusive, of spacing adjustment and an additional 0 mm to 6 mm of spacing adjustment can be provided by different sizes of the bearing support component.

Figure 17:
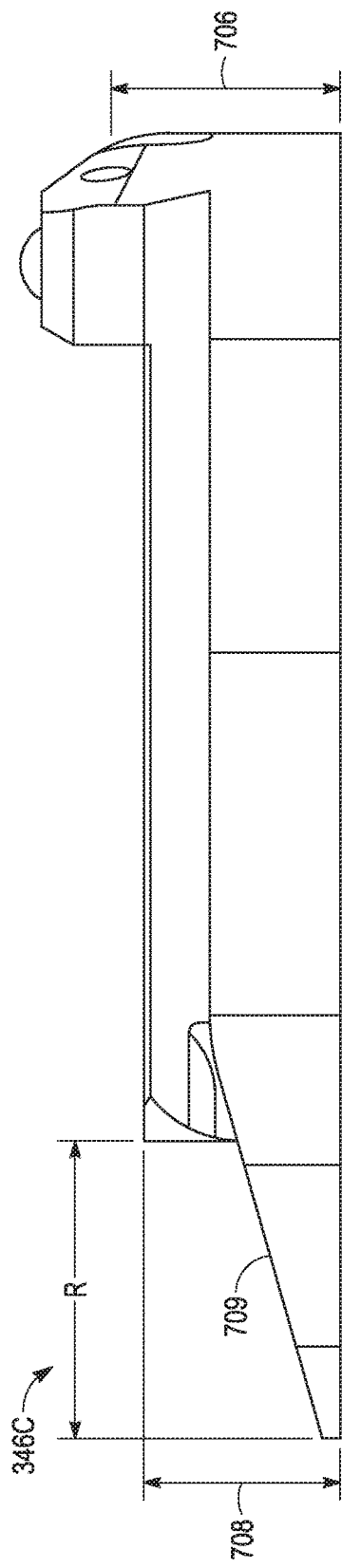
FIGS. 17-18 illustrate side views of a shim component of a tibial prosthesis system, as constructed in accordance with at least two embodiments.

FIGS. 17 and 18 illustrate side views of at least two versions of a shim component of a tibial prosthesis system. The shim component 346C of FIG. 17 includes an anterior edge height 706 that is the same or substantially the same as a posterior edge height 708. In contrast, the shim component 346D of FIG. 18 includes an anterior edge height 706 that is different than a posterior edge height 708. In the example shown, the anterior edge height 706 is less than the posterior edge height 708 and can be used by a surgeon to analyze possible bone cuts for a patient experiencing an anterior to posterior sloped knee joint. Alternatively, the anterior edge height 706 can be greater than the posterior edge height 708 and can be used by a surgeon to analyze possible bone cuts for a patient experiencing a poster to anterior sloped knee joint. Due to a height difference between the anterior and posterior edges, an inferior surface 461 of the shim component can include an anterior to posterior angle of between +3 degrees and −3 degrees, inclusive. The wedge-like shape of the shim component 346D can be used by the surgeon to assess kinematics of a knee joint if a particular bone cut is made. In this way, the wedge-like shape can be used as a feedback mechanism.

In some examples, the anterior edge height 706 or the posterior edge height 708 can provide between 10 mm and 20 mm, inclusive, of spacing adjustment between a bearing component 342 (FIG. 12A) and a bearing support component, such as a base component 344 (FIG. 12A) or a plate component 350 (FIG. 12A). In some examples, the anterior edge height 706 or the posterior edge height 708 can provide between 10 mm and 14 mm, inclusive, of spacing adjustment and an additional 0 mm to 6 mm of spacing adjustment can be provided by different sizes of the bearing support component.

In some examples, the shim components 346C and 346D can include an entry ramp 709, which can be similar to the entry ramp 614 described above and shown in FIG. 14B. A ratio R from a start of the ramp 709 to a beginning of a dovetail of each of the shim components 346C and 346D can be used to maintain engagement of the dovetails during a shim insertion procedure.

Figure 19:
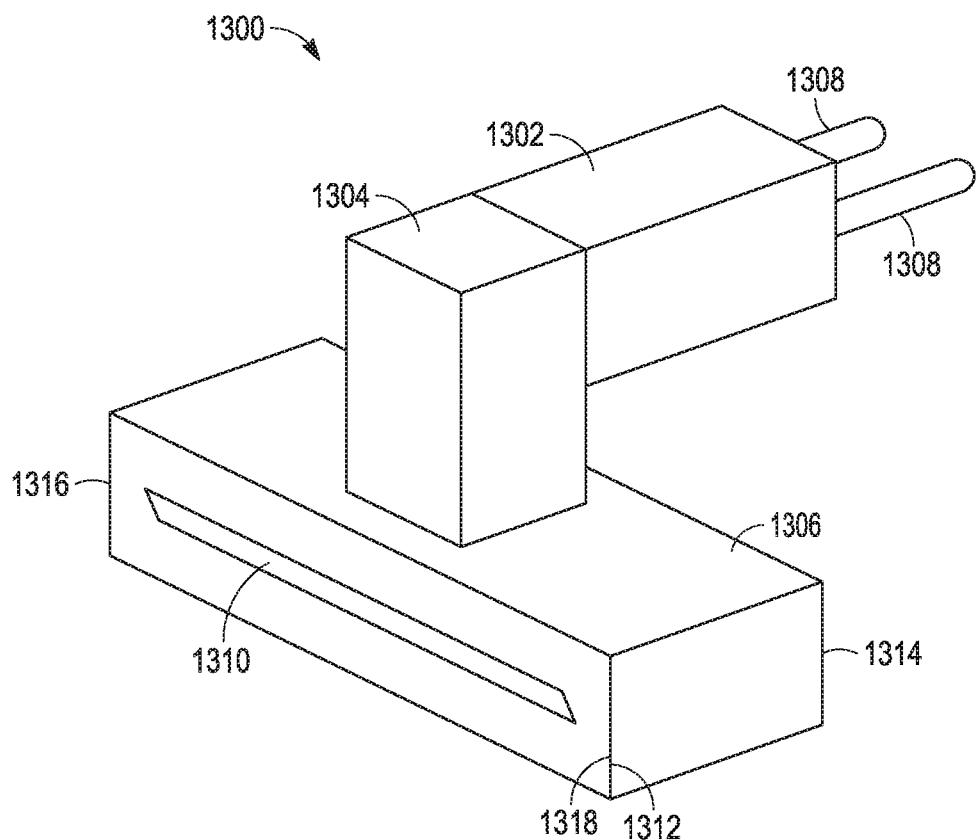
FIG. 19 is a perspective view of an example of a cut guide attachment, as constructed in accordance with at least one embodiment.

FIG. 19 illustrates an example of a cut guide attachment 1300 for use with a provisional tibial prosthesis system. In an example, the cut guide attachment 1300 can include a first body portion 1302, a second body portion 1304, and a slotted portion 1306. The first body portion 1302 or connector portion can include one or more alignment pins 1308. The second body portion 1304 can also be referred to as a main body portion. The slotted portion 1306 can include an elongated groove or slot 1310 extending through a first side 1312 to a second side 1314 of the slotted portion 1306. The elongated groove or slot 1310 can be configured to receive a cutting tool that can extend through the slot 1310. As described further below, the cut guide attachment 1300 can be used for further resecting the tibia after a provisional tibial prosthesis system has been implanted on the resected tibia. The cut guide attachment 1300 can be used to create one or more additional resection surfaces on the tibia and the additional resection surface(s) can be at an angle relative to the original resection surface.

The slot 1310 can be configured for receiving a cutting tool to further resect the tibia. In an example, the cutting tool can be an oscillating saw blade that is received through the slot 1310. In other examples, the cutting tool can be any known device used for resecting bone. A length of the slot 1310 from a first end 1316 to a second end 1318 of the slotted portion 1306 can vary and can be based, in part, on a size of the cutting tool and/or a size of the tibia that is being further resected.

In an example, the slot 1310 can have a downward slope (moving from the first side 1312 to the second side 1314). In another example, the elongated slot can have an upward slope. The slot 1310 can be configured such that the cutting tool can create a resection having an anterior/posterior slope. In an example, the slope of the slot 1310 can be between +2 degrees and −2 degrees, inclusive. In an example, the slope of the slot 1310 can be between +3 degrees and −3 degrees, inclusive. In other examples, the slope can be between +10 degrees and −10 degrees, inclusive. Different slotted portions 1306 and/or different cut guide attachments 1300 can be configured to have varying slopes within any given range. In an example, multiple cut guide attachments 1300 can be available in 1 degree increments, ranging between +2 degrees and −2 degrees.

As further described below, the cut guide attachment 1300 can be designed to be modular such that one or more components of the cut guide attachment 1300 can be replaced with another component. In an example, the cut guide attachment 1300 and/or the slotted portion 1306 can be configured such that it can be rotated 180 degrees to reverse the slope created by the slot 1310 such that a downward slope can be reversed to create an upward slope. In an example, the cut guide attachment 1300 can include alignment pins 1308 on both sides of the attachment 1300 to accommodate flipping the attachment around 180 degrees. In an example, the slotted portion 1306 can be detachable from the second body portion 1304, rotated 180 degrees and then reattached to the body portion 1304 to reverse the slope.

Figure 20:
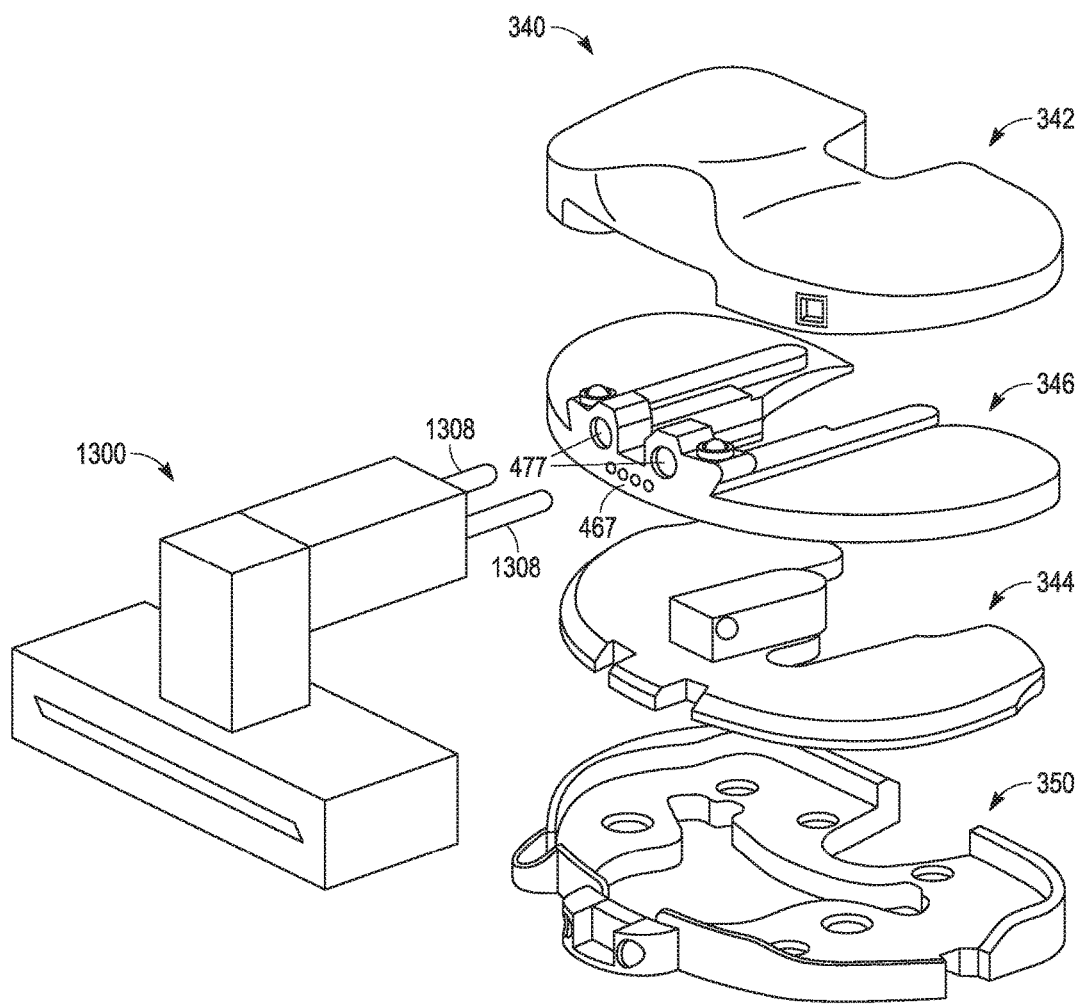
FIG. 20 is a perspective view of the cut guide attachment of FIG. 19 and a tibial prosthesis system, as constructed in accordance with at least one embodiment.

FIG. 20 shows the cut guide attachment 1300 of FIG. 19 and an exploded view of the provisional tibial prosthesis system 340 of FIGS. 11, 12A and 12B. The provisional tibial prosthesis system 340 can include the bearing component 342, the shim component 346, the base component 344, and the plate component 350. The cut guide attachment 1300 can be attached to the provisional tibial prosthesis system 340 after the system 340 has been implanted on a resected surface of the tibia. In an example, the cut guide attachment 1300 can be attached to the shim component 346. Similar to the attachment of the shim handling instrument 354 to the shim component 346, the cut guide attachment 1300 can include the alignment pins 1308 which can be configured to fit into the handling alignment voids 477 on the anterior side 467 of the shim component 346. The cut guide attachment 1300 can thus be attachable to an anterior end of the prosthesis system 340. In another example, the cut guide attachment 1300 can be attached to one of the other components of the prosthesis system 340, as an alternative to attachment to the shim component 346.

In an example, the cut guide attachment 1300 can include a release means and an engageable tooth, both of which can be similar to those same features as described above for the shim handling instrument 354. Such release means and tooth on the cut guide attachment 1300 can be used for releasably locking the cut guide attachment 1300 to the shim component 346.

As described above, the prosthesis system 340, including shim component 346, can provide insight to the surgeon regarding whether additional cuts need to be made to the femur and or the tibia such that the proper knee joint kinematics are achieved when the permanent tibial prosthesis system is implanted. As described above in reference to method 500 of FIG. 13, one or more sizing procedures can be performed at 516 to determine whether an angled bone cut is needed or beneficial prior to implanting the permanent tibial prosthesis system. Such angled bone cut can counterbalance a knee joint deficiency—such as a varus or valgus knee joint, or a sloped knee joint in an anterior-posterior direction. The cut guide attachment 1300 can be used to create one or more angled bone cuts as described above at 517 in reference to method 500. The cut guide attachment 1300 can thus be used with any of the shim components described herein, including shims having a generally uniform height and shims having a variable height in a medial-lateral direction and/or an anterior-posterior direction.

Figure 21:
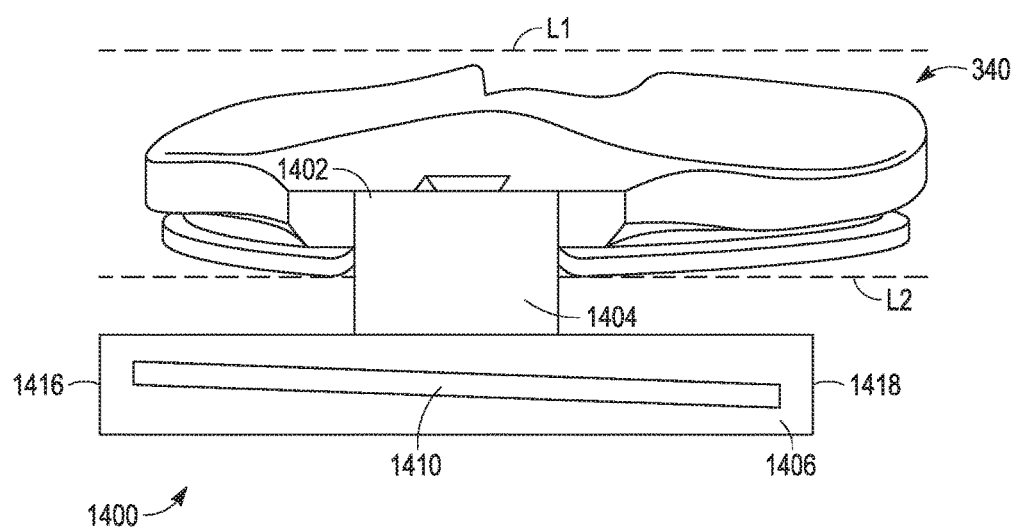
FIG. 21 is an anterior view of an example of a cut guide attachment and a tibial prosthesis system, as constructed in accordance with at least one embodiment.

FIG. 21 shows an anterior view of an example of a cut guide attachment 1400 and the provisional tibial prosthesis system 340. The cut guide attachment 1400 can be similar to the cut guide attachment 1300 of FIGS. 19 and 20, but the attachment 1400 can be configured to create a resection having a slope in a medial-lateral direction, as compared to an anterior-posterior direction described in reference to the cut guide attachment 1300. FIG. 21 also includes lines L1 and L2, which represent resected surfaces of the femur and the tibia, respectively. The tibial baseplate 350 shown in FIG. 20 is not included in FIG. 21. The provisional tibial prosthesis system 340 can include or exclude the tibial baseplate 350 when the system 340 is positioned on the resected surface 1404 of the tibia.

Similar to the cut guide attachment 1300, the cut guide attachment 1400 can include a first body portion 1402, a second body portion 1404, and a slotted portion 1406. The first body portion 1402 can include one or more pins, or another attachment feature, for releasably fixing the cut guide attachment 1400 to the tibial prosthesis system 340. The slotted portion 1406 can include an elongated groove or slot 1410 which can extend from a first end 1416, or near the first end 1416, to a second end 1418, or near the second end 1418, of the slotted portion 1406. As described above in reference to the attachment 1300, the slot 1410 can be of varying lengths. The slot 1410 can extend through a first side to a second side of the slotted portion 1406, as similarly described above in reference to the cut guide attachment 1300, and can be configured to receive a cutting tool.

As shown in FIG. 21, the elongated slot 1410 can be configured to create a slope in a medial/lateral direction, relative to the resection surface 1504 of the tibia. Thus the elongated slot 1410 can be used to create an additional resection surface having an angle in a medial/lateral direction. The cut guide attachment 1400 can be used, for example, to correct for a varus or valgus condition of a tibia. To accommodate either a varus or valgus condition, the angle can have an upward slope from left to right (medial to lateral, or lateral to medial, depending on which leg the system 340 is positioned on) or a downward slope from left to right. As similarly described above in reference to the cut guide attachment 1300 having an anterior/posterior slope, in an example, the slope of the slot 1410 can be between +2 degrees and −2 degrees, inclusive.

In order to create the slope of the slot 1410 as shown in FIG. 21, relative to the original resection line 1504, the slot 1410 as it is configured within the slotted portion 1306 can be angled from the first end 1416 to the second end 1418. In another design, the slot 1410 can be angled by orientating the cut guide attachment 1400 at an angle relative to the resection line 1504.

Because the cut guide attachment 1400 can be removably attachable to the prosthesis system 340 and because the cut guide attachment 1400 can be configured to have a sloped slot 1410, the cut guide attachment 1400 can be used to create one or more additional resections on the tibia which are at an angle relative to the original resection line 1404. As described further below, multiple cut guide attachments 1400 can be available to the surgeon having varying slopes and the surgeon can select a particular cut guide attachment 1400 based in part on a particular knee joint deficiency of the patient. In an example, the cut guide attachment 1400 and/or the slotted portion 1406 can be rotated 180 degrees to reverse the slope of the slot 1410.

In the example of the cut guide attachment 1300 of FIGS. 19 and 20, the slot 1310 of the cut guide attachment 1300 can have a slope in an anterior/posterior direction. As such, when the cut guide attachment 1300 is attached to the provisional tibial prosthesis system 340, the slot 1310 is configured to create a resection having a downward slope or an upward slope in an anterior/posterior direction. Such configuration can be used to counteract an anterior/posterior sloped knee joint. In the example of the cut guide attachment 1400 of FIG. 21, the slot 1410 of the cut guide attachment 1400 can have a slope in a medial/lateral direction. As such, the cut guide attachment can create a resection having a downward slope or an upward slope in a medial/lateral direction. Such configuration can be used to counteract a varus or valgus knee joint. In another example, the elongated slot of the cut guide attachment can be configured to create a resection having an angle in both an anterior/posterior and a medial/lateral direction.

The cut guide attachments 1300 and 1400 can include designs having a different shape than what is shown in FIGS. 19 and 21. The cut guide attachment can include alternative or additional features to the alignment pins 1308 for mating with the provisional tibial prosthesis system 340.

The cut guide attachments 1300 and 1400 can be provided in multiple sizes and can have multiple configurations such that the surgeon can select a particular attachment to use based on the particular needs of the patient. In another example, the cut guide attachments 1300 and 1400 can be a one-piece design. In an example, the cut guide attachments 1300 and 1400 can have a modular design such that one or more parts of the cut guide attachments 1300 and 1400 can be substituted with a similar part having a different size and/or configuration.

A modular design is described in reference to the cut guide attachment 1300. It is recognized that any or all of the modular features can be used in the cut guide attachment 1400. In an example, the cut guide attachment 1300 can be designed such that the slotted portion 1306 can be removably attached to the second body portion 1304 and the slotted portion 1306 can be substituted with another slotted portion 1306 having a differently angled slot 1310. In an example, the slotted portion 1306 can be attached to the second body portion 1304 from the first side 1312 or the second side 1314 such that the slotted portion 1306 can be rotated 180 degrees to easily reverse a slope of the slot 1310 (for example, from an anterior-to-posterior slope to a posterior-to-anterior slope).

The cut guide attachments 1300 and 1400 can be designed such that a distance of a second resection from the original resection (in a proximal-distal direction) can be used to determine the particular portions selected for the cut guide attachments 1300 and 1400. In an example, the first 1302 and/or second 1304 body portions of the cut guide attachment 1300 can have varying heights in order to adjust the proximal-distal distance of the slot 1310 from the original resection. The second body portion 1304 can be removably attached to the first body portion 1302 such that the second body portion 1304 and the slotted portion 1306 can be easily removed and substituted with other portions 1304 and 1306 after the cut guide attachment 1300 is attached to the provisional tibial prosthesis system 340. The cut guide attachment 1300 can include a measurement marker on a component of the attachment 1300, for example, the second part 1304, such that the user would be able to measure and/or monitor relative distances in determining one or more additional resection surfaces on the tibia.

Figure 22A:
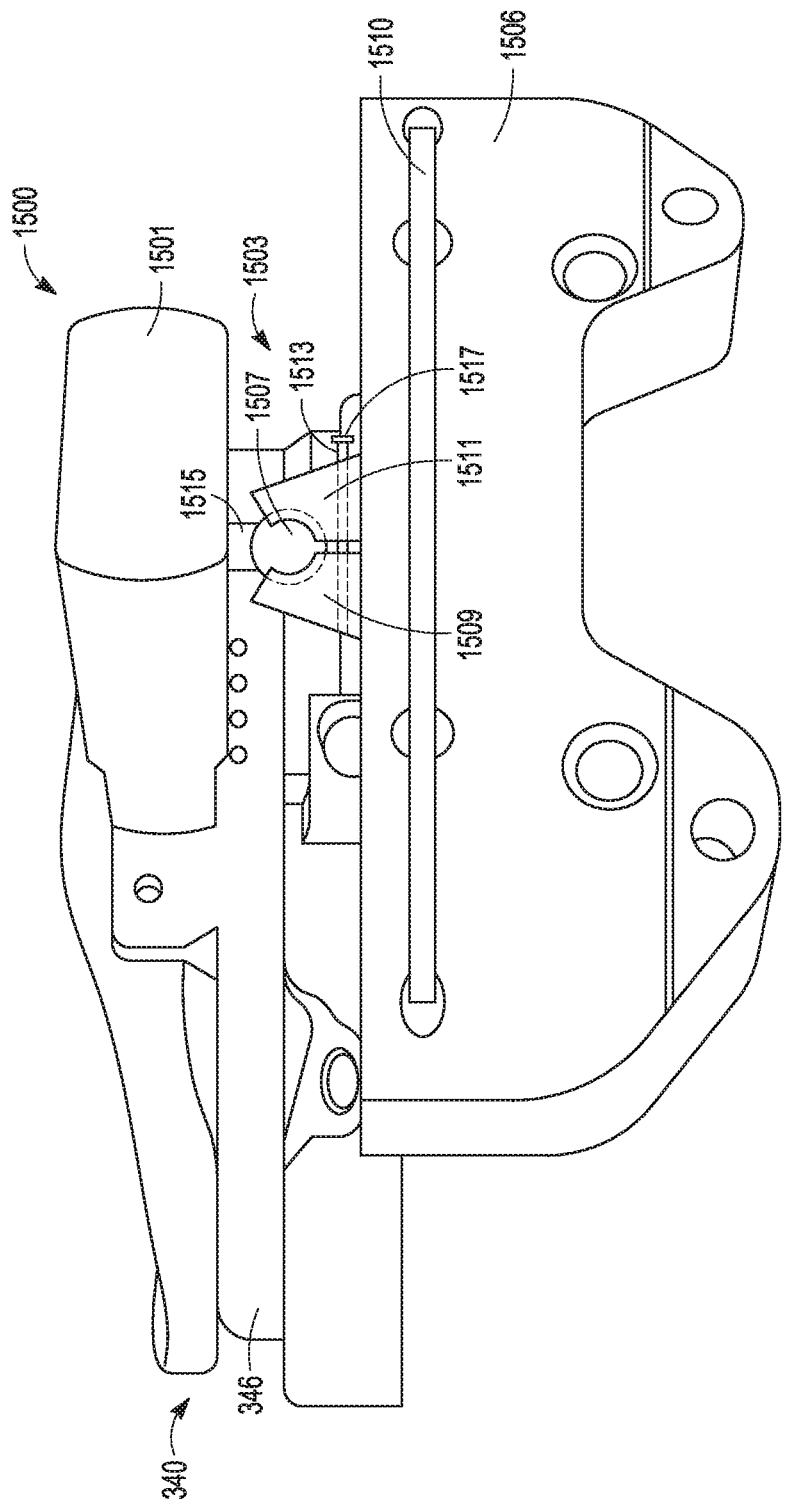
FIGS. 22A-22B are perspective views of an example of a cut guide attachment and a tibial prosthesis system, as constructed in accordance with at least one embodiment.
Figure 22B:
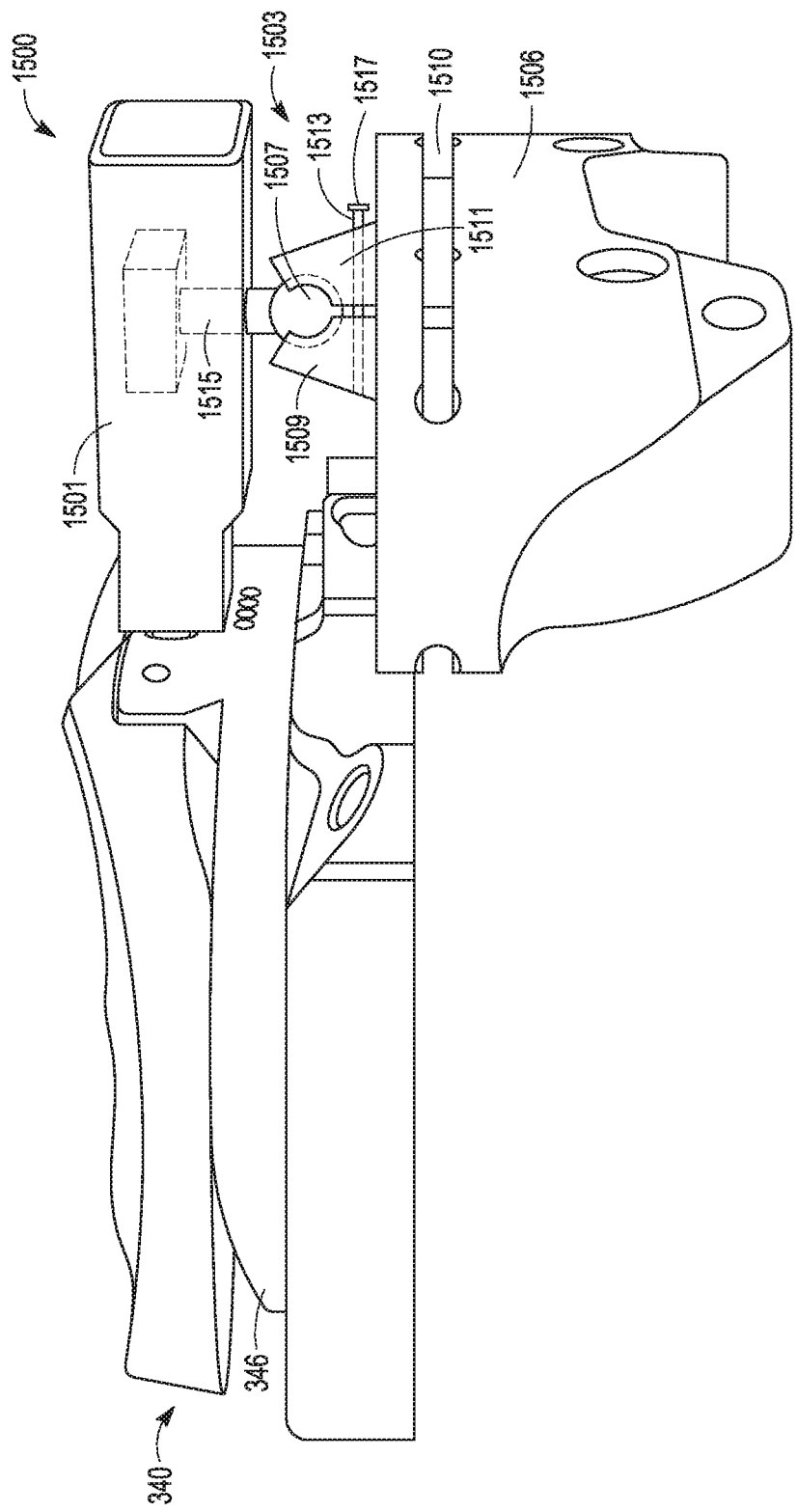

FIGS. 22A and 22B show an example of a cut guide attachment 1500 and the provisional tibial prosthesis system 340, which was also shown in FIG. 20. In an example, the cut guide attachment 1500 can be attached to the shim component 346, as similarly described above in reference to FIG. 20. As such, the cut guide attachment 1500 can include alignment pins or a similar feature for removably attaching the cut guide attachment 1500 to the provisional tibial prosthesis system 340.

The cut guide attachment 1500 can include a top portion 1501, a middle portion 1503, and a slotted portion 1506. The slotted portion 1506 can include a slot 1510 configured to receive a cutting tool, as similarly described above. The cut guide attachment 1500 can be configured to adjust a slope of the slot 1510 in a medial/lateral direction and an anterior/posterior direction simultaneously based on a design of the top portion 1501 and the middle portion 1503, which can create an adjustment mechanism having multiple degrees of freedom. Such a design can allow for infinite adjustments to be made to an orientation of the slot 1510 relative to a resected surface of the tibia. As such, the angle of the slot 1510 can be adjusted depending on the anatomy or needs of a particular patient.

In an example, the adjustment mechanism of the cut guide attachment 1500 can be part of the middle portion 1503 and can include a ball 1507, a first clamp 1509, a second clamp 1511 and an adjuster 1513. The ball 1507 can sit at least partially inside the first 1509 and second 1511 clamps; the first and second 1511 clamps can be adjustable, as described below, and can create friction on the ball 1507. The ball 1507 can be attached to the top portion 1501 using, for example, a shaft 1515 extending from the top portion 1501.

Because the slotted portion 1506 is fixed relative to the first 1509 and second 1511 clamps, a position of the first 1509 and second 1511 clamps relative to the ball 1507 can control an angle of the slot 1510 relative to the tibial prosthesis system 340. The first 1509 and second 1511 clamps can be moved toward and away from each other depending on a position of the adjuster 1513. The adjuster 1513 can be loosened using a knob 1517 in order to adjust the first 1509 and second clamps 1511 and then locked into place when a desired position is achieved.

Because the cut guide attachment 1500 is infinitely adjustable, the orientation of the slot 1510 can be adjusted throughout the surgery and the cut guide attachment 1500 can be sterilized and reused in subsequent surgeries. It is recognized that other types of adjustment mechanisms can be used that allow for an angle of the slot 1510 to be infinitely adjustable.

Figure 22C:
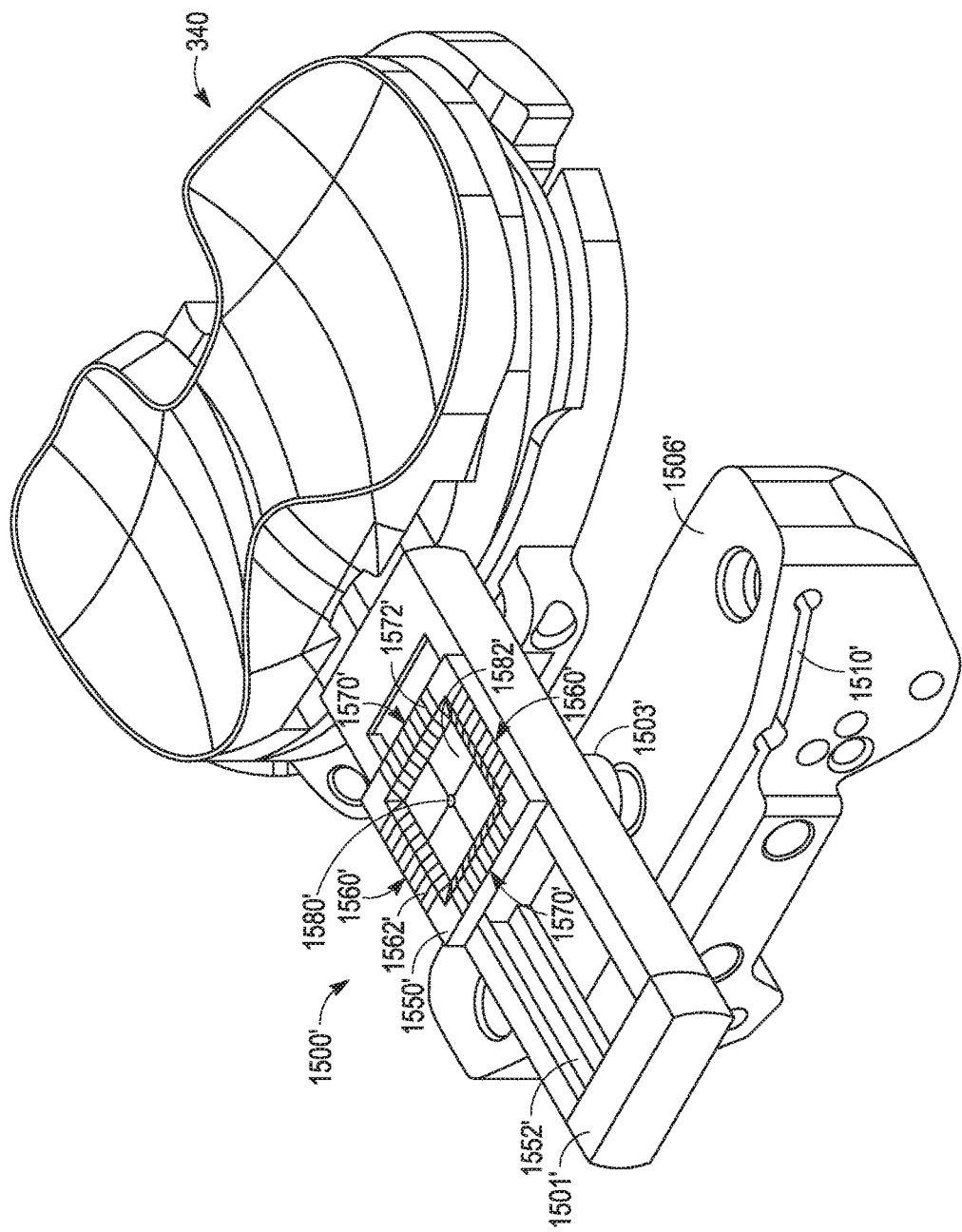
FIGS. 22C-22D are perspective views of an example of a cut guide attachment and a tibial prosthesis system, as constructed in accordance with at least one embodiment.
Figure 22D:
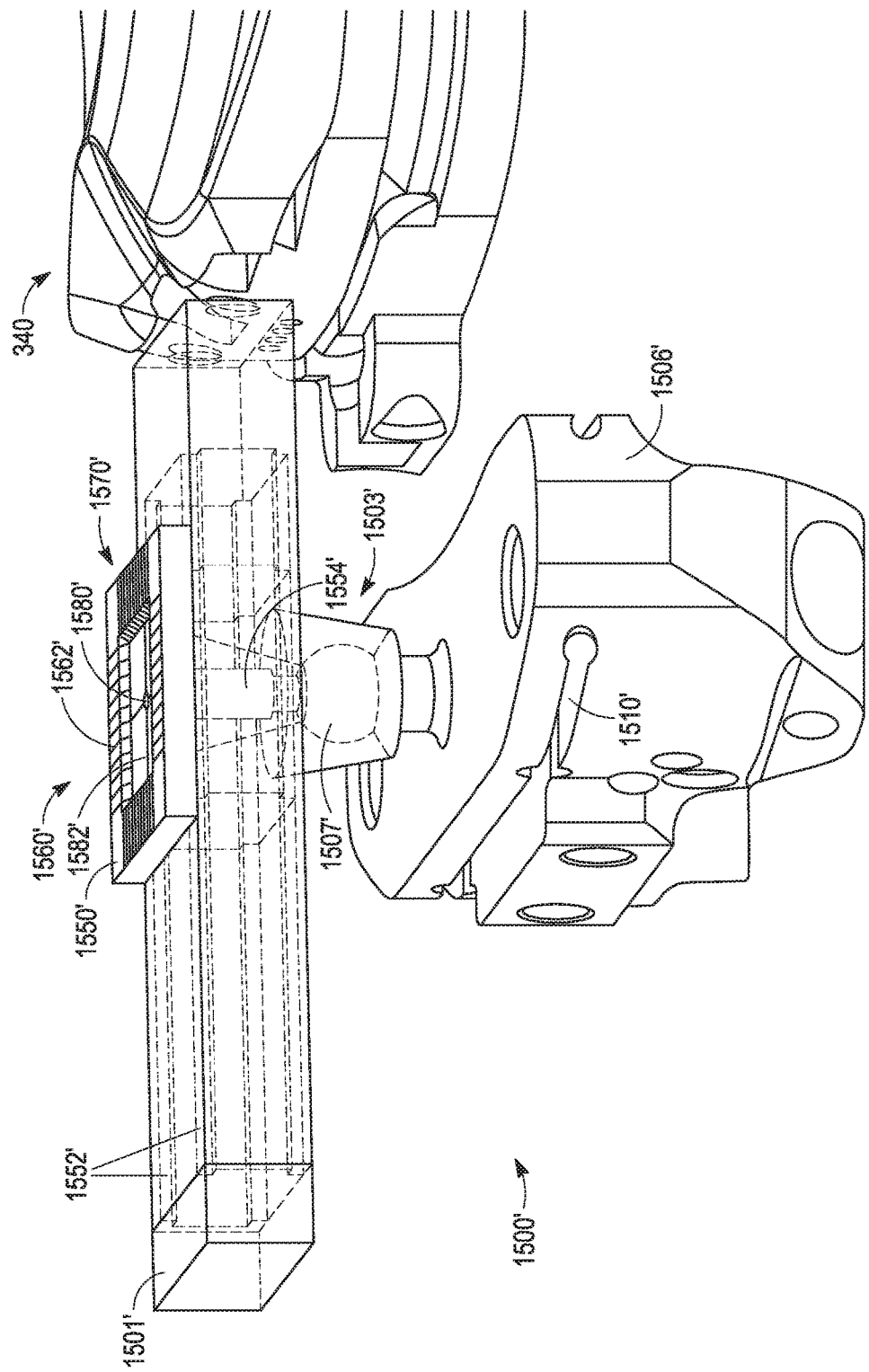

FIGS. 22C and 22D show an example of a cut guide attachment 1500' and the provisional tibial prosthesis system 340. The cut guide attachment 1500' can be similar to the cut guide attachment 1500 of FIGS. 22A and 22B, but can also include a readout feature 1550' which can be part of a top portion 1501' of the cut guide attachment 1500'. The readout feature 1550' can include multiple reference markers, described further below, for indicating a slope angle of the slot 1510' at a given position. The readout feature 1550', along with a slotted portion 1506', can be movable through the inclusion of rails 1552' formed in the top portion 1501'. The rails 1552' can allow for adjustment of the slotted portion 1506' in an anterior/posterior direction during alignment of the slotted portion 1506' with the femur.

As similarly described above in reference to FIGS. 22A and 22B, a middle portion 1503' of the cut guide attachment 1500' can include an adjustment mechanism having multiple degrees of freedom. The adjustment mechanism can include a ball 1507', which can be connected to the slotted portion 1506' of the cut guide attachment 1500' such that as the ball 1507' changes position, an angle of the slot 1510' correspondingly changes. As similarly described above in regard to the cut guide attachment 1500 of FIGS. 22A and 22B, the ball 1507' can provide for infinite adjustments to an angle of the slot 1510'. Although not shown in FIGS. 22C and 22D, the cut guide attachment 1500' can include a locking mechanism to immobilize the ball 1507' once a desired position is achieved, and then the locking mechanism can be disengaged to later adjust a position of the ball 1507'.

A pin or shaft 1554' can be connected to the ball 1507' and extend to an underside of the readout feature 1550'. Thus a position of the pin 1554' can change as the position of the ball 1507' changes. The pin 1554' can be directly coupled to the readout feature 1550' and the readout feature 1550' can change based on a change in position of the pin 1554'.

The readout feature 1550' can include four quadrants that can represent a medial/lateral position and an anterior/posterior position of the slot 1510'. A grouping of markers 1560' can represent, for example, a medial/lateral slope angle of the slot 1510', and a grouping of markers 1570' can represent, for example, an anterior/posterior slope angle of the slot 1510'. In an example, a marker 1562' in the grouping 1560' can correspond to a medial/lateral slope angle equal to zero, and a marker 1572' in the grouping 1570' can correspond to an anterior/posterior slope angle equal to zero. Thus the other markers in each of groupings 1560' and 1570' can represent positive and negative slope angles in a medial/lateral direction and an anterior/posterior direction.

A dart 1580' on the directional readout feature 1550' can be connected to the pin 1554' such that the dart 1580' can move on a surface 1582' of the readout 1550' as the pin 1554' moves. The dart 1580' can thus represent the particular slope angle in the medial/lateral and anterior/posterior directions based on a position of the dart 1580' relative to the markers 1560' and 1570'. The position of the dart 1580' shown in FIG. 22C represents a slope angle of zero degrees in an anterior/posterior direction and zero degrees in a medial/lateral direction.

FIGS. 22C and 22D provide one example of a system that includes a readout indicating a position of the slot 1510', and such system can be used with an adjustment mechanism providing multiple degrees of freedom for adjusting a position of a slot similar to slots 1510 and 1510'. It is recognized that other types of readouts or marking systems can be used to provide the user with an indication of a changing position of the slot 1510'.

Figure 23:
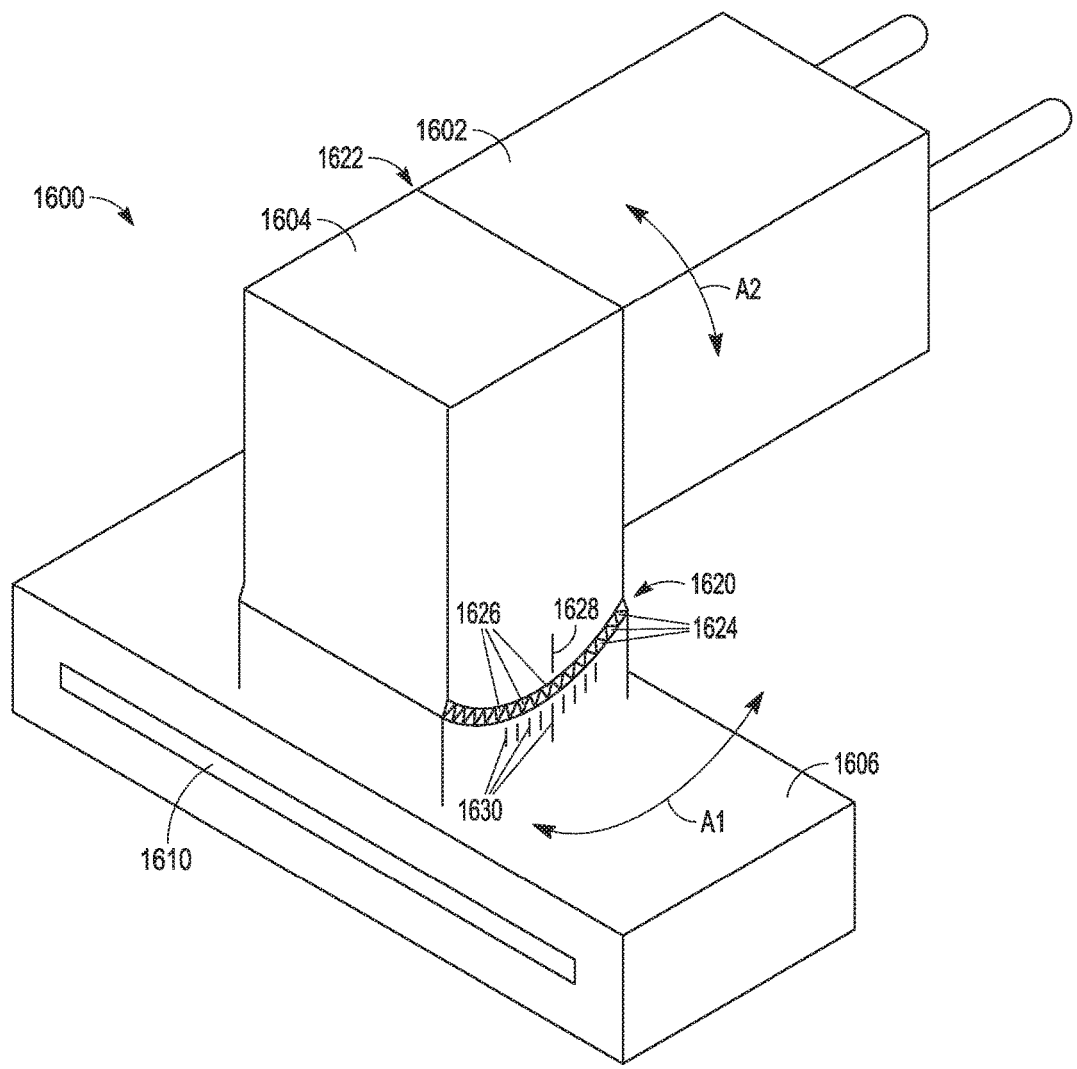
FIG. 23 is a perspective view of an example of a cut guide attachment, as constructed in accordance with at least one embodiment.

FIG. 23 shows an example of a cut guide attachment 1600. An overall shape of the cut guide attachment 1600 can be similar to the cut guide attachment 1300 of FIGS. 19 and 20 and can include a first body portion 1602 or a connector portion, a second body portion 1604 or a main body portion, and a slotted portion 1606 having a slot 1610.

The cut guide attachment 1600 can include a first adjustment mechanism 1620 between the second body portion 1604 and the slotted portion 1606, and a second adjustment mechanism 1622 between the first body portion 1602 and the second body portion 1604. The first adjustment mechanism 1620 can be configured to adjust a slope of the slot 1610 in an anterior/posterior direction, as described further below, by configuring the slotted portion 1606 to be movable, relative to the second body portion 1604, in first and second directions indicated by an arrow A1. The second adjustment mechanism 1622, as described further below in reference to FIGS. 25 and 26, can be configured to adjust a slope of the slot 1610 in a medial/lateral direction by configuring the second body portion 1604 to be movable, relative to the first body portion 1602, in third and fourth directions indicated by an arrow A2.

The slotted portion 1606 can include teeth 1624 configured to engage with corresponding teeth 1626 on the second body portion 1604. The teeth 1624 of the slotted portion 1606 can be incrementally adjusted, relative to the teeth 1626, in the directions indicated by the arrow A1 such that the teeth 1624 can mate with the teeth 1626 at a particular location on the second body portion 1604, depending on a desired angle of the slot 1610. The teeth 1624 and 1626 can releasably mate with one another at various positions, and as described below in FIG. 24, a locking mechanism can be used to releasably secure the teeth 1624 and 1626 at a particular position and allow for adjustments to be made.

As shown in FIG. 23, the second body portion 1604 can include a reference marker 1628 and the slotted portion 1606 can include multiple markers 1630 that indicate the slope angle of the slot 1610 at a particular alignment of the teeth 1624 and 1626 on the slotted portion 1606 and the second body portion 1604, respectively. As shown in FIG. 23, the markers 1628 and 1630 are aligned such that the slope angle of the slot 1610 in an anterior/posterior direction is zero.

As shown in FIG. 23, the teeth 1624 and 1626 are located across substantially an entirety of a top surface of the slotted portion 1606 and an entirety of a bottom surface of the second body portion 1604, respectively. A number and spacing of the teeth 1624 and 1626 can depend, in part, on a desired slope range in an anterior/posterior direction. In an example, the teeth 1624 or 1626 can be located on less than an entirety of the top and bottom surfaces of the slotted portion 1606 and the second body portion 1604, respectively.

Figure 24:
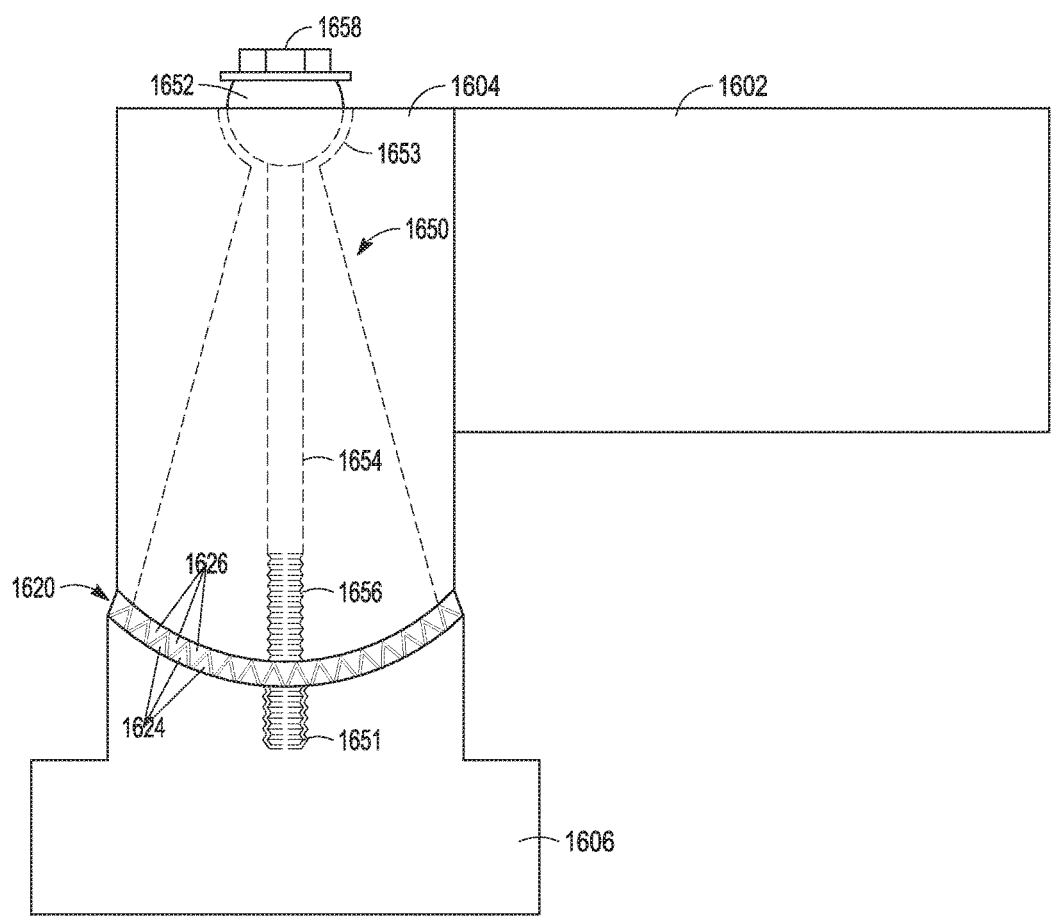
FIG. 24 is a side view of the cut guide attachment of FIG. 23, as constructed in accordance with at least one embodiment.

FIG. 24 is a side view of the cut guide attachment 1600 of FIG. 23 and shows an interior of the second body portion 1604 and the slotted portion 1606 in broken lines to further illustrate the first adjustment mechanism 1620. As described above, the teeth 1624 on the slotted portion 1606 can be adjusted relative to the teeth 1626 on the second body portion 1604 such that the slope angle of the slot 1610 can be adjusted in a positive or negative direction that correlates to an anterior/posterior slope angle. A locking mechanism 1650 can be used to facilitate the adjustment of the teeth 1626 relative to the teeth 1624. In an example, the locking mechanism 1650 can include a head portion 1652 and a shaft 1654 having an engagement portion 1656. The head portion 1652 can extend through a top of the second body portion 1604 (this is shown in FIG. 24, but not shown in FIG. 23) such that a user can grip the head portion 1652, using a knob 1658 or similar feature on the head portion 1652, to lock or tighten, as well as loosen, the locking mechanism 1650 as described below.

The head portion 1652 can be spherical and can be sized and shaped to engage a spherical engagement surface 1653 within the second body portion 1604. When the knob 1658 is tightened, the head portion 1652 can engage with the spherical engagement surface 1653 and the engagement portion 1656 of the shaft 1654 can engage with a threaded aperture 1651 in the slotted portion 106, thus moving the locking mechanism 1650 to a locked position. When the locking mechanism 1650 is in the locked position, the teeth 1624 and 1626 are mated together at a particular position, which as described above correlates to an anterior/posterior slope angle.

To adjust the locking mechanism 1650 from the locked position to an unlocked position, the user loosens the locking mechanism 1650 by turning the head portion 1652 using the knob 1658. This loosening results in the engagement portion 1656 of the shaft 1654 at least partially unthreading from the threaded aperture 1651 in the slotted portion 1606, thereby allowing the head portion 1652 to disengage from the spherical engagement surface 1653.

Once the locking mechanism 1650 is loosened, the user can adjust the position of the slotted portion 1606 relative to the second body portion 1604 until the teeth 1626 and 1624 are aligned in a desired position. At that point, the locking mechanism 1650 can be tightened such that the engagement portion 1656 returns to a threaded engagement with the aperture 1651 in the slotted portion 1606 and the head portion 1652 engages with the spherical engagement surface 1653. In this locked or tightened position, the slotted portion 1606 is once again immobile relative to the second body portion 1604. Because the head portion 1652 and the spherical engagement surface 1653 are spherical, they can mate at any desired angle, within a certain range of angles, by loosening and tightening the locking mechanism 1650. Adjustments can be made until a desired slope angle is achieved.

It is recognized that other types of locking mechanisms can be used to allow for controlled movement of the slotted portion 1606 relative to the second body portion 1604.

Figure 25:
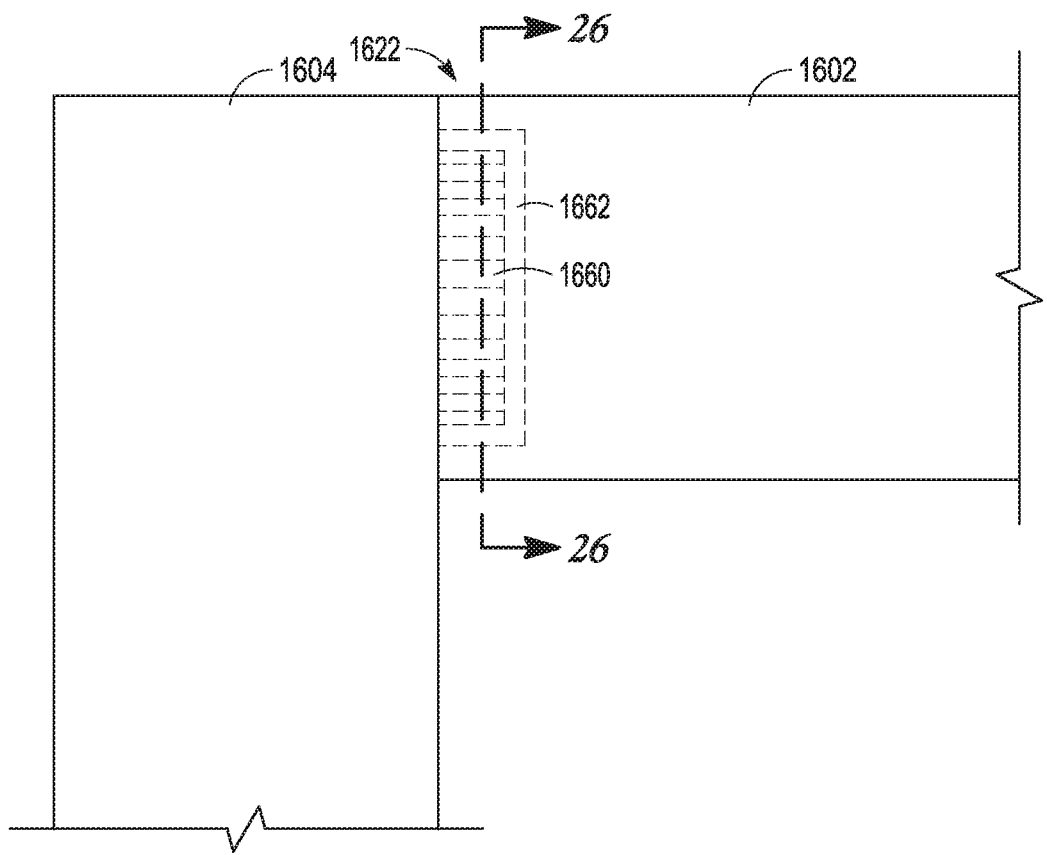
FIG. 25 is a partial side view of the cut guide attachment of FIG. 23, as constructed in accordance with at least one embodiment.

FIG. 25 is a partial side view of the first body portion 1602 and the second body portion 1604 of the cut guide attachment 1600, and shows part of the interior of the first body portion 1602 in broken lines to illustrate the second adjustment mechanism 1622, which can include a recess 1662 and a shaft 1660. The shaft 1660 can be part of the second body portion 1604 and can be configured to extend into the recess 1662 formed in the first body portion 1602. As further illustrated in FIG. 26, a diameter of the shaft 1660 can be less than a diameter of the recess 1662. The shaft 1660 can include multiple features formed on an exterior surface of the shaft 1660 to facilitate incremental adjustment of the shaft 1660 relative to the recess 1662, as described further below in reference to FIG. 26.

Figure 26:
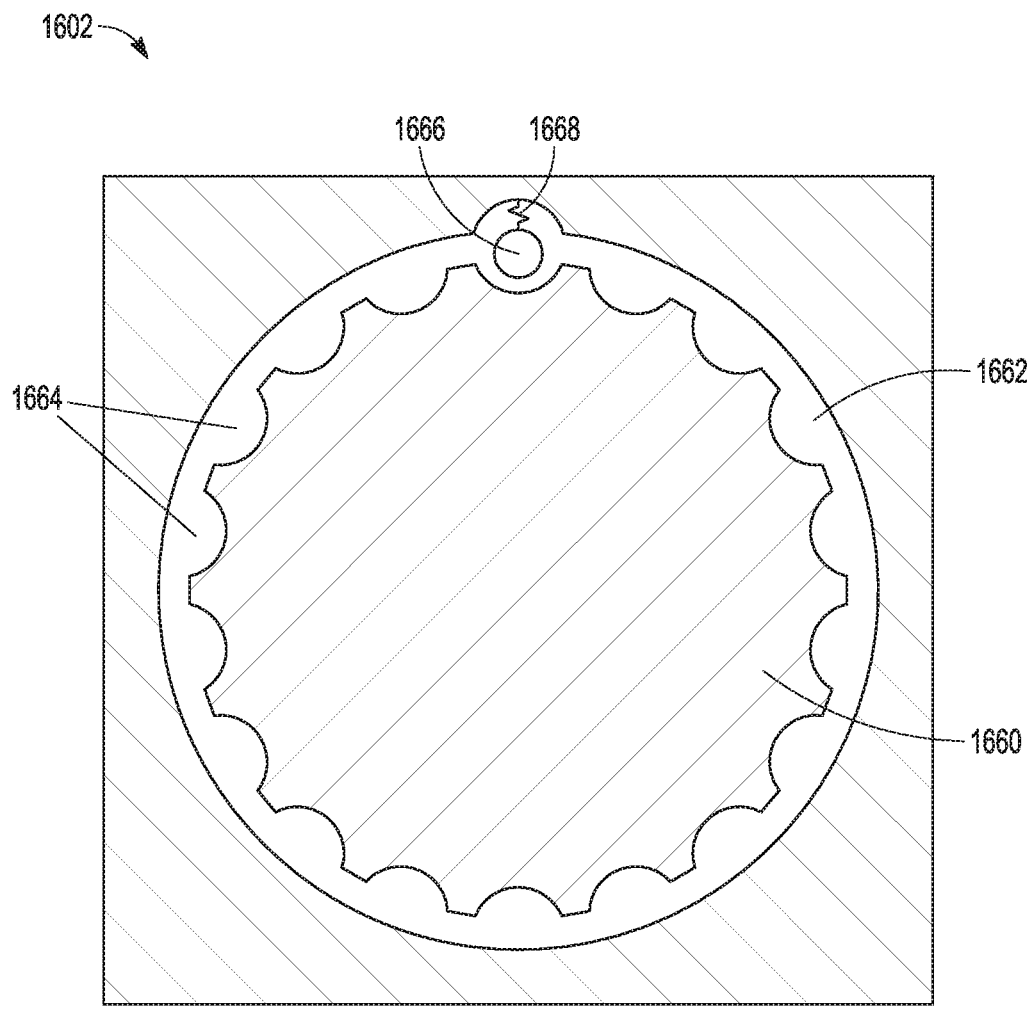
FIG. 26 is a cross-sectional view of a portion of the cut guide attachment of FIGS. 23-25, as constructed in accordance with at least one embodiment.

FIG. 26 is a cross-sectional view of the first body portion 1602 to further illustrate the recess 1662 of the first body portion 1602 and the shaft 1660 of the second body portion 1604. As described above in reference to the first adjustment mechanism 1620, the second adjustment mechanism 1622 can include a releasable locking mechanism so that the user can move the second body portion 1604 relative to the first body portion 1602 to adjust the slope of the slot 1610. In an example, the locking mechanism can include recesses 1664 formed on at least a portion of an exterior surface of the shaft 1660. The recesses 1664 can be equally spaced around the shaft 1660 and can correspond to an incremental change in slope of the slot 1610 in a medial/lateral direction. The recesses 1664 can be configured to engage with a ball bearing 1666 connected to the recess 1662 via a spring 1668.

When the ball bearing 1666 is engaged with a particular recess 1664, as shown in FIG. 26, the second body portion 1604 is locked relative to the first body portion 1602. The user can move the second body portion 1604 in either direction indicated by the arrow A2 (see FIG. 23) by exerting enough force to overcome a spring force between the ball bearing 1666 and the recess 1664. Once the user stops moving the second body portion 1604, the ball bearing 1666 can engage with the closest aligned recess 1664. Although not shown in FIG. 23, the cut guide attachment 1600 can include markers on an external surface of the first 1602 and second 1604 body portions, similar to the markers 1628 and 1630 described above, to represent an angle of the slot 1610 at a particular alignment of the second body portion 1604 relative to the first body portion 1602. If the user has a specific target slope angle, the markers can be used to indicate when the target slope angle is achieved.

As shown in FIG. 26, the recesses 1664 are located across substantially an entirety of the circumference of the shaft 1660. A number and spacing of the recesses 1664 can depend, in part, on a desired slope range in the medial/lateral direction. In an example, the recesses 1664 can be located on a portion of the circumference of the shaft 1660.

The shaft 1660 and the recess 1662 can be generally cylindrical, as shown in FIG. 26. Other shapes and designs of the shaft 1660 and the recess 1662 can be used for releasable locking of the second body portion 1604 relative to the first body portion 1602.

It is recognized that other types of adjustment mechanisms can be used in addition to or as an alternative to the second adjustment mechanism 1622 to adjust a slope of the slot 1610 in a medial/lateral direction.

The cut guide attachment 1600 as shown in FIGS. 23-26 is configured to adjust an angle of the slot 1610 in both a medial/lateral direction and an anterior/posterior direction using two separate adjustment mechanisms, as described above. In other examples, a cut guide attachment can be configured similar to the cut guide attachment 1600, but rather than including the two separate adjustment mechanisms, the cut guide attachment can include one of the mechanisms 1620 and 1622 such that the cut guide attachment is adjustable in only a medial/lateral direction or in only an anterior/posterior direction.

As similarly described above in reference to the cut guide attachment 1500, the attachment 1600 can be adjusted during the surgery as needed or desired. The cut guide attachment 1500 can be sterilized and reused in subsequent surgeries.

The cut guide attachments described herein can provide flexibility and numerous options to the surgeon for creating one or more angled bone cuts on the tibia after an initial resection is made on the tibia. In an example, a plurality of cut guide attachments and/or a plurality of differently-sized and differently-configured components of the cut guide attachment can be provided to a user as a system, which can be packaged together or separately. Such cut guide attachments can be provided to a user along with the provisional tibial prosthesis system described herein or such cut guide attachments can be provided separately.

The cut guide attachments described herein can be used in combination with the provisional or trial prosthesis systems described in pending application U.S. Ser. No. 13/836,665 titled "TIBIAL PROSTHESIS SYSTEMS, KITS, AND METHODS" and filed on Mar. 15, 2013. Such prosthesis system can be used in a knee surgery to provide full- or substantially full-surface sensing and used in combination with a user interface for displaying sensing date. The cut guide attachments described herein can be included a kit or system that includes all or some of the components for the prosthesis system in the application referenced above in this paragraph.

The above Detailed Description includes references to the accompanying drawings, which form a part of the Detailed Description. The drawings show, by way of illustration, specific embodiments in which the present tibial prosthesis systems, kits, and methods can be practiced. These embodiments are also referred to herein as "examples." While certain examples are shown and described with respect to a left knee or a right knee, it is to be appreciated that the present disclosure is equally applicable to both the left and right knees. All examples can also be used in partial or total knee replacement procedures.

The above Detailed Description is intended to be illustrative, and not restrictive. For example, the above-described examples (or one or more elements thereof) can be used in combination with each other. Other embodiments can be used, such as by one of ordinary skill in the art upon reviewing the above description. Also, various features or elements can be grouped together to streamline the disclosure. This should not be interpreted as intending that an unclaimed disclosed feature is essential to any claim. Rather, inventive subject matter can lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

In the event of inconsistent usages between this document and any document so incorporated by reference, the usage in this document controls.

In this document, the terms "a" or "an" are used to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, "anterior" refers to a direction generally toward the front of a patient, "posterior" refers to a direction generally toward the back of the patient, "medial" refers to a direction generally toward the middle of the patient, and "lateral" refers to a direction generally toward the side of the patient. In this document, the phrase "anterior/posterior direction" is used to include an anterior to posterior direction or a posterior to anterior direction.

In the appended claims, the terms "including" and "in which" are used as the plain-English equivalents of the respective terms "comprising" and "wherein." The terms "including" and "comprising" are open-ended, that is, a system, kit, or method that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The Abstract is provided to allow the reader to quickly ascertain the nature of the technical disclosure. It is submitted with the understanding that it will not be used to interpret or limit the scope or meaning of the claims.

What is claimed is:

1. A system for performing a surgical procedure on a portion of a knee joint, the system comprising:

a provisional tibial prosthesis system implantable on a first resected surface of a proximal tibia and comprising at least a tibial base plate and a tibial bearing component attachable to the tibial base plate and at least one shim that includes a first shim having a first shim height, wherein the tibial bearing component and the tibial base plate are separated by a first distance equal to the first shim height; and a cut guide removably attachable to the tibial prosthesis system configured to facilitate further resection of the proximal tibia.

2. The system of claim 1, wherein the cut guide is configured to create the second resected surface of the proximal tibia that is at an angle relative to the first resected surface.

3. The system of claim 2, wherein the second resected surface includes one or both of a slope in an anterior-posterior direction or a slope in a medial-lateral direction, relative to the first resected surface.

4. The system of claim 1, wherein the cut guide includes at least one adjustment mechanism for adjusting an angle of the elongated slot in at least one direction, relative to the first resected surface.

5. The system of claim 4, wherein the at least one adjustment mechanism includes a ball and at least one clamp, the at least one clamp adjustable and configured to releasably engage the ball, and adjustment of the at least one clamp relative to the ball adjusts an angle of the elongated slot, in at least one direction, relative to the first resected surface.

6. The system of claim 4, wherein the cut guide includes a slotted portion and a main body portion, the elongated slot formed in the slotted portion.

7. The system of claim 6, wherein the at least one adjustment mechanism includes first teeth formed on an end of the slotted portion and second teeth formed on an end of the main body portion, the first and second teeth configured to releasably mate with one another at different positions corresponding to different angles of the elongated slot relative to the first resected surface.

8. The system of claim 6, wherein the cut guide includes a connector portion having at least one feature for releasable attachment of the cut guide to the at least one shim, and the least one adjustment mechanism includes a shaft extending from the main body portion and a recess formed in the connector portion, the shaft and recess configured to releasably engage with one another at different positions corresponding to different angles of the elongated slot relative to the first resected surface.

9. The system of claim 1, wherein the at least one shim includes a second shim having a second shim height, and the second shim replaces the first shim for placement between the tibial base plate and the tibial bearing component or the second shim is used in combination with the first shim.

10. A system for performing a surgical procedure on a portion of a knee joint, the system comprising:

a provisional tibial prosthesis system implantable on a first resected surface of a proximal tibia and comprising at least a tibial base plate, a tibial bearing component attachable to the tibial base plate and at least one shim slidably receivable between the tibial base plate and the tibial bearing component; and a cut guide removably attachable to the tibial prosthesis system and configured to facilitate further resection of the proximal tibia.

11. The system of claim 10, wherein the cut guide is removably attachable to the at least one shim.

12. The system of claim 11, wherein the at least one shim includes one or more alignment voids on an end of the at least one shim, and the cut guide includes one or more alignment pins configured to fit into the one or more alignment voids on the at least one shim.

13. A system for performing a surgical procedure on a portion of a knee joint, the system comprising:
a provisional tibial prosthesis system implantable on a first resected surface of a proximal tibia and comprising at least a tibial base plate, a tibial bearing component attachable to the tibial base plate and at least one shim slidably receivable between the tibial base plate and the tibial bearing component; and
a plurality of cut guides, each cut guide removably attachable to the tibial prosthesis system and having an elongated slot configured to receive a cutting tool for further resecting the proximal tibia to form a second resected surface at an angle relative to the first resected surface.

14. The system of claim 13, wherein each cut guide of the plurality of cut guides has the elongated slot configured relative to others of the plurality of cut guides such that each cut guide is configured to create the second resected surface, relative to the first resected surface, that is different from the second resected surface created by the others of the plurality of cut guides.

15. The system of claim 14, wherein the second resected surface includes one or both of a slope in an anterior-posterior direction or a slope in a medial-lateral direction, relative to the first resected surface.

16. The system of claim 15, wherein the slope in the anterior-posterior direction is between +3 degrees and −3 degrees, inclusive, relative to the first resected surface, and the slope in the medial-lateral direction is between +2 degrees and −2 degrees, inclusive, relative to the first resected surface.

17. A method of performing a surgical procedure on a portion of a knee joint, the method comprising:
resecting a proximal tibia to form a first resected proximal tibia surface;
implanting a provisional tibial prosthesis system on the resected proximal tibia surface, the prosthesis system comprising at least a tibial base plate, a tibial bearing component attachable to the tibial base plate and at least a first shim receivable between the tibial base plate and the tibial bearing component;
testing a force balance on at least a portion of the knee joint;
performing a second resection of the proximal tibia to form a second resected proximal tibia surface, wherein the second resected proximal tibia surface is at an angle relative to the first resected proximal tibia surface, and the second resection is performed using a cut guide removably attachable to the tibial prosthesis system.

18. The method of claim 17, wherein the cut guide used in performing the second resection is removably attachable to the first shim.

19. The method of claim 17, wherein the cut guide used in performing the second resection is selected from a plurality of cut guides configured to create different resection angles relative to one another.

* * * * *